United States Patent
Beckmann et al.

(10) Patent No.: US 6,846,623 B1
(45) Date of Patent: Jan. 25, 2005

(54) LGMD GENE CODING FOR A CALCIUM DEPENDENT PROTEASE

(75) Inventors: Jacques Beckmann, Charenton-le-Pong (FR); Isabelle Richard, Evry (FR)

(73) Assignee: Association Francaise Contre les Myopathies, Paris (FR)

( * ) Notice: Subject to any disclaimer, the term of this patent is extended or adjusted under 35 U.S.C. 154(b) by 0 days.

(21) Appl. No.: 08/836,734

(22) PCT Filed: Nov. 21, 1995

(86) PCT No.: PCT/EP95/04575

§ 371 (c)(1),
(2), (4) Date: Jul. 2, 1997

(87) PCT Pub. No.: WO96/16175

PCT Pub. Date: May 30, 1996

(30) Foreign Application Priority Data

Nov. 22, 1994 (EP) ............................................ 94402668

(51) Int. Cl.⁷ ........................... C12Q 1/68; C12P 19/34; C07H 21/02
(52) U.S. Cl. ......................... 435/6; 435/91.2; 536/23.1; 536/24.3; 536/24.31; 536/24.33
(58) Field of Search .......................... 435/691.2, 320.1, 435/325, 455; 536/23.1; 530/350

(56) References Cited

PUBLICATIONS

Thomas et al, "Progress and problems with the use of viral vectors for gene therapy", Nature Rev. Gen. 4:346–358 (2003).*
Marshall, E. "Gene Therapy's growing pains", Science (1995) 269: 1050–1055.*
Harris et al, "Strategies for targeted gene therapy", Trends Genetics (1996) 12(10):400–405.*
Richard et al. (1995) "Mutations in the proteolytic enzyme calpain 3 cause limb–girdle muscular dystrophy type 2A" Cell 81(1) pp. 27–40.
Sorimachi et al. (1989) "Molecular cloning of a novel mammalian calcium–dependent protease distinct from both m– and mu–types" J Biol Chem 264(33) pp. 20106–20111.
Sorimachi et al. (1993) "A novel tissue–specific calpain species expressed predominantly in the stomach comprises two alternative splicing products with and without Ca2+–binding domain" J Biol Chem 268(26) pp. 19476–19482.
Imajoh et al. (1988) "Molecular cloning of the cDNA for the large subunit of the high–Ca2+–requiring form of human Ca2+–activated neutral protease" Biochemistry 27(21) pp. 8122–8128.
Fougerousse et al. (1994) "Mapping of a chromosome 15 region involved in limb girdle muscular dystrophy" Hum Mol Genet 3(2) pp. 285–293.
Passos–Bueno et al. (1993) "Evidence of genetic heterogeneity in the autosomal recessive adult forms of limb–girdle muscular dystrophy following linkage analysis with 15q probes in Brazilian families" J Med Genet 30(5) pp. 385–287.
Richard et al. (1994) "Regional localization of human chromosome 15 loci" Genomics 23(3) pp. 619–627.
Johnson et al. (1990) "Calpains (intracellular calcium–activated cysteine proteinases): structure–activity relationships and involvement in normal and abnormal cellular metabolism" Intl J Biochem 22(8) pp. 811–822.
Saido et al. (1994) "Calpain: new perspectives in molecular diversity and physiological–pathological involvement" FASEB J 8(11) pp. 814–822.

* cited by examiner

*Primary Examiner*—Jeffrey Fredman
(74) *Attorney, Agent, or Firm*—Nixon & Vanderhye P.C.

(57) ABSTRACT

A nucleic acid sequence comprising: 1) the sequence represented in FIG. 8; or 2) the sequence represented in FIG. 2; or 3) a part of the sequence of FIG. 2 with the proviso that it is able to code for a protein having a calcium dependant protease activity involved in a LGMD2; or 4) a sequence derived from a sequence defined in 1), 2) or 3) by substitution, deletion or addition of one or more nucleotides with the proviso that said sequences still codes for said protease.

11 Claims, 33 Drawing Sheets

A) Genomic structure of the nCL1 gene
B) EcoRI restriction map 10-16kb
C) Cosmid map

```
      1330        *****        1350                              1370          *         1390                              1410                              1430
GCTTGCTCTGCCGGAGGCTGCCCGACTTCCCAGATACTTTCTGACCCTCAGTACCGTCAGTGAGCTCTGAGGAGGACGATGACTCGATGACTGAGTCGATTGAGTTC
 G  C  S  A  G  G  C  R  N  F  P  D  T  F  W  T  N  P  Q  Y  R  L  K  L  L  E  D  D  D  D  S  E  V  I  C  S  F

1450          .          1470                              1490                             1510           ▼         1530                              1550
CTGTGGCCCCTGATGCAGAATGACAAGACCCGGAAGCTTAGGGCCAGTCTCTTCACCATTGGCTTCTCCAAAGATGTCACGGGAACAAGACGACCTG
 L  V  A  L  M  Q  K  N  R  K  D  R  K  L  G  A  S  L  F  T  I  G  F  A  I  Y  E  V  P  K  E  M  H  G  N  K  Q  H  L 1570                              1590          .          1610                              1630                              1650                              1670
CAGAAGGACTTCTTCTTGTACAACGCCTCAAGGCACAGAGAACCTACAACCTACAAAACCAAGAGAAGCAAACTCTTCCCACCGGTGTCATCGTGCCCTCCACC
 Q  K  D  F  F  L  Y  N  A  S  K  A  R  S  K  T  Y  I  N  M  R  E  V  S  Q  R  F  L  P  P  S  E  Y  I  V  P  S  T 1690                              1710                              1730                             1750           ▼         1770                              1790         ▼
TACGACCCCCACCAGGAGGGGGAATTCATCCTCCGGGTCTTCTCTGAAAGAGAACCTCTCTGAAGTTGAAATACCATTCTGTGATGGCCAGTGAAAAGAAAACCAAG
 Y  E  P  H  Q  E  G  E  F  I  L  R  V  F  S  E  K  R  N  L  S  E  E  V  E  N  T  I  S  V  D  R  P  V  K  K  K  T  K 1810                              1830                              1850                              1870                              1890                              1910
CCCATCATCTTCGTTCGGACAGAGCAACAGAGCAAATGGGCCCTGATAGCAAACAGCCTGAAAAGCAGTCCCCACAGCCAG
 P  I  I  F  V  S  D  R  A  N  S  N  K  E  L  G  V  D  Q  E  S  E  E  G  K  G  K  T  S  P  D  K  Q  S  P  Q  P  Q 1930                              1950                              1970                              1990                              2010                              2030
CCTGCCAGTCTGATCAGGAGGAAAGTCAGGAGGACAGCAGGACAACAATTCCGAACATTTCAAGCAGATAGCAGGAGATGACATGGAGATCTGTGCAGATGAGCTCAAGAAGGTCCTTAACAGTC
 P  G  S  S  D  Q  E  S  E  E  Q  Q  Q  F  R  N  I  F  K  Q  I  A  G  D  D  M  E  I  C  A  D  E  L  K  K  V  L  N  T  V

2050         ▼         2070                              2090                              2110           ▼         2130                              2150*
GTGAACAAACACAAGGACCTCAAGACACACGGGTTCACACTGGAGTCTGCCCGTAGCATGATTGCCCGATCAGATGACTGACGACTGACGAGTCGAAAGTCAACCGAGGAGTTCCACCTC
 V  N  K  H  K  D  L  K  T  H  G  F  T  L  E  S  C  R  S  H  I  A  L  M  D  T  D  G  S  G  K  L  N  L  Q  E  F  H  H  L 2170                             2190           ▼         2210                              2230                              2250                              2270           ▼
TGGAACAAGATTAAGGCCTGGCAAAATTTTCAAACACTATGACACAGACAGACCAGTCCGGCACCAGTCAACCAGATCAACACTCAAGAATCCACCTCAACAAC
 W  N  K  I  K  A  W  Q  K  I  F  K  H  Y  D  T  D  Q  S  G  T  I  N  S  Y  E  H  R  N  A  V  N  D  A  G  F  H  L  N  N 2290                              2310                              2330                              2350                              2370                          ▼    2390
CAGCTCTATGACATCATTACCATGCGGTACGCCAGAGACAAACATGAACATCGACTTTGACAGTTTCATCTGCTGTTTCGTGAGGCATGTTCAGAGCTTTCATGCATTGAC
 Q  L  Y  D  I  I  T  M  R  Y  A  D  K  H  N  I  D  F  D  S  F  I  C  C  F  V  R  L  E  G  H  F  R  A  F  H  A  F  D 2410                              2430                              2450
AAGGATGGAGATGGTATCATCAAGCTTAACGTTCTCGAGATGCTGCAGCTCACCATGTATGCCTGA
 K  D  G  D  G  I  I  K  L  N  V  L  E  M  L  Q  L  T  M  Y  A
```

A) EXON 2

B) EXON 8

C) EXON 13

D) EXON 22

LISTE DE SEQUENCES (1) INFORMATION GENERALE:

(i) DEPOSANT:
        (A) NOM: AFM
        (B) RUE: 13, place de Rungis
        (C) VILLE: PARIS
        (E) PAYS: FRANCE
        (F) CODE POSTAL: 75013
        (G) TELEPHONE: (1) 45 65 13 00

(ii) TITRE DE L' INVENTION: LGMD GENE (iii) NOMBRE DE SEQUENCES: 4

(iv) FORME LISIBLE PAR ORDINATEUR:
        (A) TYPE DE SUPPORT: Floppy disk
        (B) ORDINATEUR: IBM PC compatible
        (C) SYSTEME D' EXPLOITATION: PC-DOS/MS-DOS
        (D) LOGICIEL: PatentIn Release #1.0, Version #1.25 (OEB)

(2) INFORMATION POUR LA SEQ ID NO: 1:

(i) CARACTERISTIQUES DE LA SEQUENCE:
        (A) LONGUEUR: 3018 paires de bases
        (B) TYPE: acide nucléique
        (C) NOMBRE DE BRINS: double
        (D) CONFIGURATION: linéaire (ii) TYPE DE MOLECULE: ADN (génomique)

(xi) DESCRIPTION DE LA SEQUENCE: SEQ ID NO: 1:

```
TGATAGGTGC TTGTAAACTG TGCTTAACGA AAACATACCG TGTCCTGTAG GGACTTAACT      60

CTTGTTTATA TCAGTTAGCC TGGTTTCGCT AACAGTACAT CATTTTGCTT AAAGTCACAG     120

CTTACGAGAA CCTATCGATG ATGTTAAGTG AGGATTTTCT CTGCTCAGGT GCACTTTTTT     180

TTTTTTTTAA GACGGAGTCT CTTTCTGTCA CCTGGGCTGG AGTGCAGTGG CGTGATCTGG     240

GTTCACAACA ACCTCTGCCT CCTGGGTTCA AGCAATTCTT CTGTCTCAGC CTCCCAAGTA     300

GCTGGGATTA CAGGCACCCG CCGCCACACC CGGCTTATTT TTGTATTTTT AGTAGAGACA     360

GGGTTTCACT ATTGTTGACC ATGCTGGTCT CGAACTCGTG ACCTCATGTG ATCCACCCGC     420

CTCGGCCTCC CAAAGTGCAG AGATTAGAGA CGTGAGCCAC ATGGCCCAGC AGGACCACTT     480
```

FIG 8A/1

```
TTTAGCAGAT TCAGTCCCAG TGTTCATTTT GTGGATGGGG AGAGACAAGA GGTGCAAGGT    540
CAAGTGTGCA GGTAGAGACA GGGATTTTCT CAAATGAGGA CTCTGCTGAG TAGCATTTTC    600
CATGCAGACA TTTCCAATGA GCGCTGACCC AAGAACATTC TAAAAAGATA CCAAATCTAA    660
CATTGAATAA TGTTCTGATA TCCTAAAATT TTAGGACTAA AAATCATGTT CTCTAAAATT    720
CACAGAATAT TTTTGTAGAA TTCAGTACCT CCCGTTCACC CTAACTAGCT TTTTTGCAAT    780
ATTGTTTTCC ATTCATTTGA TGGGCAGTAG TTGGGTGGTC TGTATAACTG CCTACTCAAT    840
AACATGTCAG CAGTTCTCAG CTTCTTTCCA GTGTTCACCT TACTCAGATA CTCCCTTTTC    900
ATTTTCTGTC AACACCAGCA CTTCATGTCA ACAGAAATGT CCCTAGCCAG GTTCTCTCTC    960
TACCATGCAG TCTCTCTTGC TCTCATACTC ACAGTGTTTC TTCACATCTA TTTTTAGTTT   1020
TCCTGGCTCA AGCATCTTCA GGCCACTGAA ACACAACCCT CACTCTCTTT CTCTCTCCCT   1080
CTGGCATGCA TGCTGCTGGT AGGAGACCCC CAAGTCAACA TTGCTTCAGA AATCCTTTAG   1140
CACTCATTTC TCAGGAGAAC TTATGGCTTC AGAATCACAG CTCGGTTTTT AAGATGGACA   1200
TAACCTGTCC GACCTTCTGA TGGGCTTTCA ACTTTGAACT GGATGTGGAC ACTTTTCTCT   1260
CAGATGACAG AATTACTCCA ACTTCCCCTT TGCAGTTGCT TCCTTTCCTT GAAGGTAGCT   1320
GTATCTTATT TTCTTTAAAA AGCTTTTTCT TCCAAAGCCA CTTGCCATGC CGACCGTCAT   1380
TAGCGCATCT GTGGCTCCAA GGACAGCGGC TGAGCCCCGG TCCCCAGGGC CAGTTCCTCA   1440
CCCGGCCCAG AGCAAGGCCA CTGAGGCTGG GGGTGGAAAC CCAAGTGGCA TCTATTCAGC   1500
CATCATCAGC CGCAATTTTC CTATTATCGG AGTGAAAGAG AAGACATTCG AGCAACTTCA   1560
CAAGAAATGT CTAGAAAAGA AAGTTCTTTA TGTGGACCCT GAGTTCCCAC CGGATGAGAC   1620
CTCTCTCTTT TATAGCCAGA AGTTCCCCAT CCAGTTCGTC TGCAAGAGAC TCCGGTGAGT   1680
AGCTTCCTGC TTGCTGGCTG GGTTTCCCCC CCACGGAGGA GTCCTCTCAC TCAGCACCTC   1740
CGGCAGCTCA GCTGTGCACA TGGGCACTGG GGAAGGATC CTGGCAGCAG CTCTGCTGGG   1800
CTCTGTCTTT AAGTGTGAAC CAGGGAGGAG AGGAACAGGT CTCAGATATT TCACCAAATC   1860
TCAGCAAAAT CCAGACGGAG AGCGCAGGAG GTGGGGTGAT TCTTATGCTC TGGCTCTTTC   1920
TCTCTGAAAA AAAAAAAAAA ATCTTGCTTT TTATAAAAGT GGGTGGAACT CAGTTTAATT   1980
CATCCTGTAA AAATAAATAT TCCTTTCTCA GAACAAATTC CAGACAGCCC AGATGTACCT   2040
GTTCGTTTTA ATATTATTCA TCTTGGTAAG ATTATTTCAG TTTCTCTGGC TAAAATCATG   2100
```

FIG 8A/2

```
ATGTTATTCT TCTTTAATTT ACCAATGGCC ATTCTTTCTG AAACACAGAA ACCCTAGAAA    2160
GAGAAGAGTC ATAGGCAAGG AATTTTTTTC ATGCATAAAA TGTTGGGGTT AAAGAGAGAG    2220
AGACCTAGCA ATCGCTTTGG TCCACCTACC TCACCTCATA AGTGAGGAGT CAAGGCACAC    2280
TAGAGTGAAA TATATCTAGT GGGCACATGA CAGAGCCCGG ATTAAAACTT TGTTTTAGGA    2340
AACTCTCCCA GCCTCTGGGT TTCATTTACA GTGATCGCCA GGAGGGAAAT CACATTCCCC    2400
TGGCTCACCT CTCTGATCAT CCCTCCAGTG TGACTCTTGT TCTTAATTCG AGAAATATTT    2460
ATTGAGCATC TACTAGTGCC AGCACTGGGC AAGCAACTGG GGGACAGCA GTGAGTAAGA     2520
AAGACCAAAA TTCCAGCTGT CTTGGAACCT AGGGTCCTGA AGGGAAGATG GGCATTGAAC    2580
AAGAGTGACA TTGTCAGGAG ACGATGTTCT GGGTGCCACA GGATCATGTG GCAAGGAGAG    2640
CTAACCTGGT CCAGGGAGAC AAACCCTCTC TGAGGAAATG ATGACAAGCT GAGACCCAAT    2700
ACTATTGATT AGCCATGGTT TTCTTTAACC TAAGGTGGGC CAGGCATGGT GGCTCATGCC    2760
TATAAACCCA GCATTTTGGA AGCCCAGGC TGGAGGATTG CTTGAGCCCA AGAGTTAGAG     2820
ACCAGCCTGG GCAACAGGGT GAAAACCTAT CTCTTTTGTA CTAAAAATTC AAAAAATTAT    2880
CCAGGCATGG TGGCACATGC CTGTGGTCCT AGCTACTCAG AGGCTGAGGT GGGAAGATCA    2940
CTTGAACTCG GGAGTTTGA GGCAGCAGTG AGCCGAGATC ATGCCACTGC ACTCCAGGCT     3000
GGGTGACAGG AGTGAGAC
                                                                    3018
```

(2) INFORMATION POUR LA SEQ ID NO: 2:

(i) CARACTERISTIQUES DE LA SEQUENCE:
       (A) LONGUEUR: 11451 paires de bases
       (B) TYPE: acide nucléique
       (C) NOMBRE DE BRINS: double
       (D) CONFIGURATION: linéaire (ii) TYPE DE MOLECULE: ADN (génomique)

(xi) DESCRIPTION DE LA SEQUENCE: SEQ ID NO: 2:

| | | | | | |
|---|---|---|---|---|---|
| GATCCACCCG | CCTTGGCCTC | CCAAAGTGCT | GAGATTACAG | GTGTGAGCCA | CCACGCCCAG | 60 |
| CCGACACTGC | CCTAACTCTC | AAGTTGCATC | CTTACTCGAA | TAGTATGACA | GTGTGGGAAG | 120 |
| CAGCATGGGA | CAATGTAAAA | AGGAGGCATG | TTTCTGGCTT | CTGCTACTTA | CTAGCTGTGT | 180 |
| GTCTTTGCAC | GAGTTTCTTA | ACCTCTCTGG | GCCTCAGTTT | CCTTATCTGA | AAAATAACAA | 240 |
| TGATACTATT | CCCTTCACAG | GGCCAAATGG | AATACTATCA | GGAACACTAC | ATAATCGAAC | 300 |
| TCAATAAATA | ATAGCTACTG | CGGCCGGGCG | CGGTGGCTCA | CATCTGTAAT | CCCAGCACTT | 360 |
| TGGGAGGCCG | AGGCGGGTGG | ATCACAAGGT | CAAGAGATGG | AGACCATCCT | GGCCAACATG | 420 |
| GTGAAACCGT | ATCTCTACTA | AAGATACAAA | AATTAGCTGG | GCATGGTGGC | GCATGCCTAT | 480 |
| AGTCCCAGCT | ACTCGAGAGG | CTGAGGCAGG | AGAATCACTT | GAACCCCGGA | GGCAGAGGTT | 540 |
| TCAGTGAGCC | AAGATTGCAC | CAGTGCACTG | CAGCCTGGCG | ACAGAGTGAG | ACTCCGTCTC | 600 |
| AAAAAAATAC | CTATCTATCT | ATCTGTCTAT | CTACTGTTAT | TCTTACCTGG | TCATTTCCTT | 660 |
| TTTGTTTCAC | AGGAAATTTG | CGAGAATCCC | CGATTTATCA | TTGATGGAGC | CAACAGAACT | 720 |
| GACATCTGTC | AAGGAGAGCT | AGGTAGGAAA | GTGCCTCAGG | TCAGATCCTG | CCAGATGATC | 780 |
| AAGGGGTGAT | TACAAGGTGT | GATCCCCTTC | CAGGAGGTAA | AGGGACAATC | TGTGCTTGCT | 840 |
| TCCAGTAACT | TTTTGGAAGA | TTTTTTATAA | CAGTTGCTTT | ATGGTCGTTT | ATCTACATGC | 900 |
| TGGCGATTGC | TTCATTTCCT | CCTACATGCC | TCTTTAGCAC | TCTGCCATGC | ATCACAGGGG | 960 |
| GTATCTGCAT | CCTGTGGCCT | CCTCTCCAGT | ATCTCAAGGA | CACTTACATA | CCCCACTCAG | 1020 |
| CATGACAAAA | GCCCTGCTTT | TCACTGTATC | GTCTTTCTTG | GAAGACAGCT | CTGTGACTGT | 1080 |
| GCACCAAGCA | TGCCCCTTGG | GCATGGAGAT | TCTAGATACA | CACACAAAAG | GCATCGCCAA | 1140 |
| GGAAAGCACT | TGTAACTGGA | ACCCTTGGTT | TAAATTGGCC | CAGCATAGCT | CCATCTTTAA | 1200 |

FIG. 8/B1

```
AAGAGTCTTT CCACAAAGAT GGCATCCGCC ATGTGGATGA GCATCCAATT TTCTCTTTGA    1260
TTGGTTAGCT TGACTGCTCC ATCTGATCTT CCTCTCTCTC GACCTCTTGT TCAGAAAGTA    1320
TTGTCTTTGG TGTGGACTAT AAGCAAGCTC TGTGAAGTAA AATTGGAGAG AACACCAACA    1380
GAAACAATTT AAATTTGAGG AAAAGGGGGC ACCTAAGACC AAAGGAATTT GGCTTATTTC    1440
ATTCCAGAAG GGGAGGCTGA GAATAAATCA GATGAATATC TGGGTTCCTG CACCTGAGGG    1500
AAGGCTTCCT GCAGAGCCCT GGGCATAATA ATCTGGGACC TTCAAACCAA TAACCTCTTT    1560
TCCAAGGAAA GACTGGCTGC TTCCAAGGAG GGTAGGGAG AGTCGGGCTG CAGGCAGCTC    1620
TCAAGTCTCC CCTTGCACAC TCTCAGGTTG GCATTTTCAC TTTAACCCAT CCTCCCTTAA    1680
GAAGGCAGTT CTTTGTGACC AGGGTACACC CCCTATTATA TATATATATA CACACACAGA    1740
GAGAGAGAGA GAGAGAGAGA GAGAGAAAGA GAGCAAAGTG TTACCTCCAA CTACATACAG    1800
TACTCTGTCA GAAAGAGGT TCAGAGAATA AGAAAACGTC CCGAGCTCAT TCCGTTGCCA    1860
GCAATGTCTT ACTGCCCCCT ATAGACGGGT TCCAGGGCAG CTGCCTACCT GGCCTTCCTT    1920
CCAATACAAA TCATCTTGGT GGATGGTTCT CTGAGGCTCA GTCTTCGCTG AAGTCAGAAC    1980
AGGAATTGGA CTCACATTGC AAAGGCACAG GGCAGGGCAG ATTTCCTACA GGTGTTAGGA    2040
AGAACAACCC AGTTATGATC ACCTACTGCT CTGTCTCCAT TGAGGCCTAA AAAGGAAGTG    2100
AGTTTATACT GCAGTTGGAG GAACTGCCTG CAGCCTTGAG GAAAATGTCT AGTCACAAGG    2160
GAGTAAGTTA CCTGTTGATC ATATTGTCAA GGAATTCCTG TCCAATTCTC CTTCCCTGGG    2220
TTGACACCTC TGTAAGGTCA GATCTGGAAG TAGGAGACTG GGCACCAAGG GAGTCCCCGT    2280
TCAGGGAAGT GGAGTGGCTG GCTGGGATTG GGGCTTTTTC TTCCCAGGAG GAGCAGGAGT    2340
GCTCACGATC TGTGCCCTGT GTCTGCCTGC AGGGACTGC TGGTTTCTCG CAGCCATTGC    2400
CTGCCTGACC CTGAACCAGC ACCTTCTTTT CCGAGTCATA CCCCATGATC AAAGTTTCAT    2460
CGAAAACTAC GCAGGGATCT TCCACTTCCA GGTGAGGTAA TGAGAGTGTA GTTAAGAGGG    2520
CCAGCGGCAG GCCACCCACC GCTGGTCTCC TGGCCTTGAC TTCCCAGAAG CTGGAGGAAA    2580
CTTCCCACCC ATCTACCCGC AGCGGCAACA GTCGGCATGG ACCCCTTAA GGCTTCAAGC    2640
CTGGGAGGAA GCAGTTGCTT ATCTCTGGCT CCCTAATCCC TCCCCCACCA CCTTCCACTA    2700
TGTCCCAGAA AGACAGGAAG ACATCCTGTT TACTGTGGGT CTATTTTTGT CTTTCCAGCT    2760
GTCTGGCTGC TTTTATTGCC TGCAGCCCTT CTCAAGTAGG TCCCTAAGAT ATTAGCACTG    2820
```

FIG. 8B/2

```
TGACACCACA GGACCCTTCA GGTTGTACAG GAACCCCTGT CCAGGGCTCC TGTATACTTC    2880
TTCCTCTCTA AGGCATGGCG GTACCAAGGC TATCACTCCT CTCTTCCAAG CCCTGGAAGA    2940
AGAGTCTGCT TAACCTGGGG ATCAGGCTTC TTGTTTGCCC TAGAACTGAA TCTGATGGTT    3000
CTAGAATCCA TCCAGCTACT GGAAATTTTC TGGGTCCCAG TCACCTTGGC ATAGAGCTGG    3060
TGCTAGAGCA GAACCAAACT GAATTCTACC TGTGAGGGTC TCGTAGCTTC CGGGATGCTG    3120
GGGAGTCAGC CTGTCTCCAG CTTCAAAGGC TCCCTCATGT CCCAGGATGA CCCACATTAT    3180
CAGTTCTTGC TCCCCGGGTC TTGCACCTCA GCACGGAAGG CCTCAGAAAA GGTCTGTCTC    3240
CAGGCTCAGA CTCCCCCTCC TGCCGCCTTG GAACATGGC ATATTTAAAG GGTCTCAGAT     3300
CTAAAGGGCC TTACATACAA ATATCAGATA GATTTCTGTT CTCATTTCAA TGAGGGAGAA    3360
AGTGCCATTG AAAAGGAGAC TAAACCACAT TTGGCCCTTT TCAGTTCAAA CTGATTCATT    3420
CAAAAAGAG CGACATCCAA ACTTGAAATG ATTGAACAAT GTTCCTGCTA CAGCTAGAAT     3480
AGATTCTGGG TCACTTTGTT CCTCCGTTTC AATCCTTGTT CTTCAGTTTG GCATCAAGAA    3540
ATACCTAAAT CAGCACAGTG CCTTCACTGC ATAGTTCCCA ATCCTGGCCA CATTGAATCA    3600
GCTGGGGGCA CCTGAGAGTG CTGACACCCA GGCCCTGCCC CAGACCTGCT GAGCAGGACA    3660
ATGAAAATCT TACATCCTAA GACACTCATG GAGCACCTAC TCTACCCATT ACTGGGCTGG    3720
ACTCTGTGGA AGACATGAAG TATATGTAAC TCACTTCCAG CTCTCAAAAA GCACCCACTC    3780
CAGTTAGAGA CAGATTTACA CACCCCAAAC ACAAAATAGG ATGAACAGGC ACCCAGATGC    3840
AGAGTCCAGG AAATGATGCT GCTTTGGGAT TCAAGAACCC CCTGAGGAAT GTGGACGAAG    3900
GACACATTTC CTAACAGTAA TTTGAGTATG TGACTCTGTG CGTGACGCTT CTGTGCAGTT    3960
CTGGCGCTAT GGAGAGTGGG TGGACGTGGT TATAGATGAC TGCCTGCCAA CGTACAACAA    4020
TCAACTGGTT TTCACCAAGT CCAACCACCG CAATGAGTTC TGGAGTGCTC TGCTGGAGAA    4080
GGCTTATGCT AAGTAAGCAA CACTTTAGAA TGTGAGGTGC GGCTAGAGGT GAGAAAGTGG    4140
GTTGCAAAAT CCAGCCGAGA CCTCACTCAC AGGAAGAGGC ATGTGCCTCT ATACGTGCAT    4200
ATGTGTGGGC ATCCAACTCC AACTGTGACC CAAAGTTAGA GATCAGTTCC AGGCAACAAC    4260
ACCTCTAACT AAAAACATTA AATTTAAGAG TAGAAATGAA GATTTGCATA GAAGACCTTT    4320
AGCTTTAGCT CACCATAGCG AGTTCTTTCA TTGCACCTCC ATGGTGGCAT TGCAAGTCTT    4380
GGGATCAGAG CATTGTCCCA GGCTCTCGAT TGGCTCAACC TCATGTGCTT ATAGAAGATT    4440
```

FIG. 8B/3

```
TATAAAGACA TGTTGTCTCT CAACTTAAAA GCTCCACCCC AGATGATAAT AATGGATTTT    4500
CAAATTTTGG AACAAGGTCA CTCTGTAATG CAGGCTGGAG TGCAGTGGTG CAGTCACGGA    4560
TCACTGTAGA TTGACCTCCT GGGTTCAAGG TGCTCCTCCC ACCTCAGCCT CCCAAGTAGC    4620
TGGGACTACA TGCGGGCATC ACCATGGCCC TTTTATTTTT GTATTTTTTT GTAGAGCGGG    4680
GTTTTCCCAT GTTGACCCAG ACTGTTCTCG AACTCTTGGG CTCATACAAT CCACCAGCCT    4740
TGCCCTCCCG AAGCGCTGGG ATTGCCGGTG TGAGCCACCA CACCGGCAGC TGCTAATGCC    4800
TTTAATGCAG CCCTTCCTCA ACGTTCAGGA TGTAGTGGAA AGAGCTCTCA GGAAGTGGGG    4860
ATAGCTGGGT TTCAATCCCA GTGCTTCTGG CTCTCTGTGG TCTTGGGTGG GTCACTTAGC    4920
CTCTTGAGCT CAGTTTCTTC ATTATGAAGA AAGGAATCA TTGTTTCCAT CCCATGAGCT    4980
CATAGGGTTA ATGTGGAATT GATGAAAGAA CATCACAGCA TCCAAGAGGT AAAGTTCTGG    5040
TGGCAGTGGT ACCTGGGTTT TGTTCCCTGG AACTCTGTGA CCCCAAATTG GTCTTCATCC    5100
TCTCTCTAAG GCTCCATGGT TCCTACGAAG CTCTGAAACG TCGGAACACC ACAGAGGCCA    5160
TGGAGGACTT CACAGGAGGG GTGGCAGAGT TTTTTGAGAT CAGGGATGCT CCTAGTGACA    5220
TGTACAAGAT CATGAAGAAA GCCATCGAGA GAGGCTCCCT CATGGGCTGC TCCATTGATG    5280
TAAGTCTGGG GTGTGGGGCA CAGGCTGGGG AGCTCCAAGT GTCAGGAAGC CTTTTACCCA    5340
ATGAAGGGCA GCATAGAGCT TTTGTGTGGG ACAGAGCGAA TGTTTTGTTT GAGGAAGCAG    5400
GAACTGGCTC TCAACTTTGA GGACTGGGAA TTTCTCAAGG GAGAACAGTT CTTCCGGATT    5460
TTCAATAAAG ACACTGGTCA AGGACATTTC AAGCCCTGGA ATGTCAGTGG AAATCAGTCC    5520
AGAGGCCTGT GTCAGTGGAG GCCTCCCTTG CTGGTGCTCC TCAGTCTCAG CACGCTCCCA    5580
TTAAGCTGGC CACGTACTTG GCTGTGGACC TGAGCCCACC ATTTCCCTAA GAAAGCCTCC    5640
CAGTCACTGG GCTTTCACCA CACCTCCCCG CTTGAGACGT GGGCTTTGTG TTGTTACCTG    5700
GGAGAAGCTA AGCCTGCAGC ACCTTTCAGT GCAAAGAAAT GCTGTGAACT GAGACAGGAG    5760
CCAAGGGTAG GGAGATGGCC GCCCATGGCC AGGCCTCCTT CAGGGGGCAT GCCTTCCCTG    5820
AGGGCTGCTC AGTATATTGA TATGATAATC TTAGTGGTTT CCATTGGGGA GGATGGGGCT    5880
GAAGCTGAAT TCCTGCCCCT TCTTCTCCCA ACACGCCCAA TGGACAGCTT GGAAGGTCAG    5940
TTAGCACACA ACACCATGGA TGAACTTTTT TTCTGTATCA CTTTTCTCCG TCTTTCCTCC    6000
ATTCGTGCTC TGTTGATCTC TCCTCTCTCC CTTTGTCTGT CCCATCTCTT TCTCCTCTCT    6060
```

FIG. 8B/4

```
CCTTCCCTTT CCACCCTTCT GTGTTTGTTC TCTCCCTCCC CTGTGTTGTT CCCTACATTC    6120
TCCATCGGGC CTCAGGATGG CACGAACATG ACCTATGGAA CCTCTCCTTC TGGTCTGAAC    6180
ATGGGGAGT  TGATTGCACG GATGGTAAGG AATATGGATA ACTCACTGCT CCAGGACTCA    6240
GACCTCGACC CCAGAGGCTC AGATGAAAGA CCGACCCGGG TGTGTACACC TCCGATTATC    6300
AGAACTGACC ATCCCTCCAA CCCACATGAC CCCGCCCTAT TAGTGTCAGA CTCCCCTCAG    6360
CAGCCAGGGC CTTACCCACA CACCCCCACC TGGCACCTCC CAAGGGTCTG GGTTGAAATA    6420
ACTTGCTCAG CCAAGGCTCC TGAAGAGGGT GCAAGAACCA GGATTTTGGA GGGAATCTCT    6480
GCTGGAGTTT CTGCATATTC CATGGTCCAG GCAGTTCCTC TCATAACGAA CTATCAGACA    6540
GAAATACTTG TAAAGATACT TCATTTATTT TGAAATATTT TTCCTCTTCT AATGTATTCA    6600
TTTATTCATT CAACACTTAT TTTTGAGCTC CTACTATGTT CCAGGCACTC CTCTAGCAAA    6660
CAAAGCAAAT TCTCTCCTCT TTTTCAATAT TTGTGGAAAA AGCAAGGTCT CCCTCTTGTA    6720
GAGTTTATAT TCTAGTATTT TCATAAGTTA TACCTGCTCA CTGGAGAATA CTCAGCCATA    6780
CAGAAAAACA CAGAGGAAAA TTTCACTTAT ATTTTTCCCC ATGTAAAGAT AACCACTCTT    6840
AACATCTAGT ATATGTTCTT CCAGGATTTT TCTATGCACA CACTGAATCT GTATTTTTAT    6900
TTTTAAAATG TTATCATATT GTATGTACCT CTTTGCAGCC TGCTTTTTTC AGTTAGTTTT    6960
TTTGGTTTTT TGGTTTTTTT TTTTTTTTGG AAACCAAGTC TTGCTCTATT CCCTAGGCTG    7020
GAGCACAGTT GTTGCCATCT CGGCTCACTG CAACCTCTGC CTCCAAAGTT AAACTAATTC    7080
TCCTGCCTCA GCCTCCCGAC ATAGCTGGGA TTACAGGCAC ACACCACCAC ACATGCCTAA    7140
TTTTTGTATT TTTTAGTAGA GACGGGGTTT CACCATGTTG GCTGGAATGG TCTTGAACTC    7200
CTGACCTCAA GTGATCCACC TGCCTCAGCC TCCCAAAGTG CTGGGATTAC AAGTGTAAGC    7260
CACCACACCC GGCCTAGTTT GATATTCTTA ATGTGCCCAA AGTATTCTCC TGTAACATTT    7320
TTTAATAGCT ACACAATATT CAAACACACA GATATGTTAT AATTTATTTA CCCAATACCC    7380
TATTATTGGA AAGTTGAGTT CTTTTTTTTC TTTGTTTTGT TTGTTTTGC  TACTATTCTA    7440
AAATGCTATA ACGAACATCC CAATAGATAC ATCTTTGTAT ACATCCATGG TGACTTCCAT    7500
AGGACAGATT CCCAGCAGTA GAATTGCTGG GTTGAATGAT ATGCTTAGGG TAATGACAGA    7560
AGAGTCATTT CAAGCAGCTT CCTAGGGTCT TAGAACTTAA GGATTAATGA GTCTTCCCGC    7620
CCCCTCCCAG TCTATTCAGC ATGATCTGGA TCATGAGGAC TGAGATCTGG AAGAGACTGA    7680
```

```
GATCTGGGAG AGGCTGAGAT ACCAAAAGCC CTGGCTCCAC CCATACCCCT CGCCCTGAAA    7740
ACAGCTCTAG GAATTCCGCG GCCTAGCAAG GCTCCGGGAA GCTCCTTTTA AAGCTGTGAC    7800
GTTAGTAGGC ACATGGACCA TAGAGACCTA TCCAGGGCTC ATGGGACTTT AGTGATCCTG    7860
CCCTTCTCCC AAGGATCCCC CATGGCTGCA ACTTGGAAAT TTCTGCAAAT GGAAGAGCTA    7920
CTCCTTAGGC ACGGTCATGT CTGAGCAGGG ATCTCCTCGG GCTTTCTTAG AATTCTCTCC    7980
CTGGGCACTC GGACTCTTGA TTTCTTGAAT ATTATGTTCC AGGTGGGTGT GGAGGAGGTG    8040
AGGGGATGTA AAGAAGGCTA GACTTGGCCA GGCGCAGTGG CTCATGCCTG TAATCCCAGC    8100
ACTTTGGGAG GCTGAGGCGG GTGGATCACC TGAGGTCAGG AGTTCGAGAC CAGCCTGGCT    8160
AACATGGTGA AACCCCGTTT CTACTAAAAA TACAAAAAAT TAGCTGAGCA TGGTGGCACG    8220
TGCCTGTAAT CCCAGCTACT CGGGAGGCTG AGGCAGGAGT ATCGCTGGAA CACGGGAGGC    8280
AGAGATTGCA GTGACCCGAG ATCGCGCCAC TGCACTCCAG CCTGGGCGAC ACAGCAAGAC    8340
TCTGTCTCAA AAAACAAAAA AGAAAGAAAA AAAGGAAAAG CTAAGACTTA CATGTGTCAC    8400
TTAACCCCTT TTCTCAAACC TCTTTCTCTT CCAGGAATAG TCAACCCCTG GATGGCTTCA    8460
GGGGAAGGGG GATCCTGAAG CCCAGGGCAG CCTCCAACTC TACCCCTTCC TCCTTTGAAG    8520
GATACTAAGG GGTCCAGAAA GGAGGGGCAG GACACTGTTA CCCACCCCAC ATCCCAGCAT    8580
CCACATTGCT CTCTGATGGT CAGGACAGAG CCTTCTCAGG GAGACCAGCC TGTCTGGAGC    8640
TGTGTCTCTT GGCACTCTTA AAGGGCCACT GAAGGTCCGT TCGTGGTCGT GAGGCACACT    8700
TTCAGGGAGC AGAGTGGTCT GTGTCTTCAC AGAGCCCGGA AAATGAACTA GTATGAACTT    8760
TGCCTCCAAG CAGCAGAACT TCTGTTCCCC CGCCCCTAAT GGGTTCTCTG GTTACTGCTC    8820
TACAGACAAT CATTCCGGTT CAGTATGAGA CAAGAATGGC CTGCGGGCTG GTCAGAGGTC    8880
ACGCCTACTC TGTCACGGGG CTGGATGAGG TAAGCCTGGT GGGGCTTGGT GGGGCAAGGG    8940
CACCCTCCTG GGTTAACCTC ATGAAGTCAG GACTTAGCTG TTGGGGCCCC TGCCCTGTCT    9000
GCAGAGCTTG CCTCCAATCA GGACATTCAG TTCAAGGTCC AAGCCACGCC TGGGAGCAGA    9060
GGGGCCTGTG AAACTGGTAG AGGTGGATCC TGCCACAGTT GGTGCACAGT TTATCTTTGC    9120
TTTTCGTGCT AAAGATGGCA ATTTTTCCAA CATTTCCAAT GAACAAATTG AAATATCACT    9180
TAACTTTGCT TTTACAAAGT TGGTTTCATG TGTTCTTGAG CTTCCTGTTC TCTCGTGTTC    9240
AGATAGCTAC AGTTGTCTCT GGGTAGCCAC GGGGACTGGT TCCAGAAGCC CCAACAGTAA    9300
```

FIG. 8B/6

```
CAAAATCTGC AGATGCTCAA GTCCCTTCTG TAAAATGGAG TAGTATTTGC ATATAACCTA    9360
TGCACATCCT CCCATATACT TTAAGTCATC TCTGGATTAC TTACGATACC TAACACAATG    9420
GAAATGCTAT GTAAATAGTT ATTGCACTGC ATTGGGTTTT TTTGGTATTA TTTTCTGTTG    9480
TTGTATTATT ATTTTTTCTT TTTTTGAATA TTTTTGATCC ACAATTGGTT ATATGCCAAA    9540
GCCATGGATA CGAGAGGCTG ACTGTTCTGT TTTGCTCCTT CTGGGACTTC TGGGTTTTCC    9600
TGGACCATGT CTGAGACAGG AACGTTGTAA GACCTGTTGC ACACAGTTGG GCAGGTTGTG    9660
CCCTGTACAG AGGGATGGGC TGAGAGGGGC AGTTGCCTGC ATCACCCATT GCAGCAGACT    9720
GGAGGGAGTC TGCTTGTTTG TAGTTCCTCA GTCAGCAGGG GCCTTTTGTC TTTCCTTCCT    9780
TTCCTTTTTT TTTTTTTTTG AGACGGAGTC TCACTCTGTT GCCCAGGCTG GAGTGTAGTG    9840
GCACAGTCTC GGCTCACTGC AATGTCCGCC TCCTGGATTC AAGCGATTTT CCTGCCTCAG    9900
CCTCCTGAGT AGCTGGGATT ACAGGCGCGT GTCACCATGC CCAGCTAATT TTTGTATTTT    9960
TAGTAGAGAT GGGGGTTTCT CCATGTTGAT CAGGCTGGTC TCGAACTCCT GACCTCGTGA   10020
TCCGCCCACC TCGGCCTCTC AAAGTGCTGG GATTACAGGC GTGAGCCACC ACGCCTGGCC   10080
AGCAGGGGCC TTTTTTCTAA TTTATATGAA GACACCTAAT TTATATGTGT TAGCAAAGCC   10140
CTCCTGTTTA TGCCTCACCT CCTCCCCCGA AGCTCATACG GCAGGATGTT CCTGAGAAAA   10200
TTGCCTCTTA GAAGATAGAG AGGAGATGCC AAGCCTAAGT TAGGCAGACT CAGGAGGATA   10260
GGTCTGACCC ACCCCCTGCC ATTCCCCAGC ACACTTGTGA TTAATCTCCT TGGCCAGAGC   10320
CAGGCAGAAC ACCCTCGCGT AAGAGATTTG CCCCCCAGCC CCGTCCCAGC CCTCAGCTAG   10380
ACAGAAGATT CCCTTTCCAG AGAGGCTGCA GAGCATGAGA GCTCTTTCTG TGTGCTTAAG   10440
GTCCCGTTCA AAGGTGAGAA AGTGAAGCTG GTGCGGCTGC GGAATCCGTG GGGCCAGGTG   10500
GAGTGGAACG GTTCTTGGAG TGATAGGTAG GTGAGGGGAC CCCACGGGAT TGGCGGTGGC   10560
GGGGAACAGG GTCCGGGACA AGGCTGTGTT GGGAACTGAG CCATGAGAGT ATTGAAGATG   10620
CTTGGTATAA AATCACCCTC AAAACCAATG ATCCGCAGAG AAGAGGGCA CAGGTGTTCC    10680
CTCCAGGGAA GGGCCAGGAC TGGAAGCGGG GTGCTGGGGA CCCAGAGAGG TTGCTGACAA   10740
CCATTGGCTG GAAAGGAAGG ATTCCAGAAA GCGTGGGGAA GGTCCAGGCA GGAAAAGCGT   10800
ATGAATGCAG GGTTCTGGGC TAGAGAAGTG ACTTCCCTTC TTGGGGTCTT GTCTTGCCTT   10860
TCCTGTGAAA TGGGAACAGT ATTATTAGCA CTTACCTTGT GGGCTGATAT TGAGGAGTAA   10920
```

```
CTGGGACTTG TTTTTGGGCA AGTGCTGAGC CATTGCTAAG ATTCCCCTTA CCCGTGCTTG    10980
TCCCTTGTAT TAAGGCACAA GGGCCCTTTG AAAAGAATTT TACCTGCTTT ATCAATTGAA    11040
AGGGATTAAG ACCTTGGGGG CCAACCCAAA ATAAACATGC GAACTTATTA TTTATAGGCT    11100
CCATGCACAC TTCGTAAAAC CTCCATGGTC CTACTGGTTC CTGATTACCT CCACTCAATG    11160
AGAGGCAATT CATTACTGAA TGAGCCATAA GCGCCTCTTA TTTCGAGAGG GGATGGCAG    11220
GACTCAGTCG AGGAGAAGGA CCGCACCCAG GCAGCCTGGG CCCCTCGGCT CCTGTACTTA    11280
TTTACTGCTG GGTACTTCCT AGCCCAGCAT GTAATTACTG GTTCGTTCAG TCATTCGTTT    11340
AGTAAATGTT TCTTGGGCAC CTACTACATA GGAGGCACAG GTCAAGGCAC TGGGGATATT    11400
CTTTCTACCC ACCCCCTCCC TCCCTACACT GTGATTAGGG ACTGACCGAT C             11451
```

FIG. 8B/8

(2) INFORMATION POUR LA SEQ ID NO: 3:

(i) CARACTERISTIQUES DE LA SEQUENCE:
       (A) LONGUEUR: 1834 paires de bases
       (B) TYPE: acide nucléique
       (C) NOMBRE DE BRINS: double
       (D) CONFIGURATION: linéaire (ii) TYPE DE MOLECULE: ADN (génomique)

(xi) DESCRIPTION DE LA SEQUENCE: SEQ ID NO: 3:

| | | | | | |
|---|---|---|---|---|---|
| ATTTTTTTTT | TTTTTTTTGA | GACGGAGTCT | CACTCTGCCA | CCCAGGCTGC | AGTGCAATGG | 60 |
| CGCGATCTTG | GCTCACTGCA | ACCTCCGCCT | CCCGGGTTCA | AGTGATTCTT | CTGCCTTAGC | 120 |
| CTCCTGAGTA | GCTGAGACTA | TAGGTGCCCG | CCACCACGCC | CAGCTAATTT | TTGTATTTTT | 180 |
| ATTAGGACGG | GGTTTCACCA | TATTGGCCAG | GCTGGTCTCG | AAATCCTGAC | CTTGTGATCC | 240 |
| GCCCACCTCG | GCCTCCCAAA | GTGCTGGGAT | TACAGGTGTG | AGCCATTGCG | AGCAGCCCAG | 300 |
| AACTCAATTC | TTAACCTTTA | AAGTATGATG | AGAAGAAGGA | TCAAGCCCTC | ACCAGCCCAT | 360 |
| TTAAGGAGTT | TAGGCTCACT | CTTGAGGATG | TGAGAAGTCA | TTGCTATTGG | GTTTCACACT | 420 |
| GAGGTTAACA | GGTGAAGTCA | GCATTTTGGT | AGTTCACAGC | AGCTGCAACT | CTTTGTATTT | 480 |
| CTCTGATACC | TCCTGTCCCA | ACCTACATCA | GGCCTTCCCT | TCTTCCTGCT | TCCTTAATTC | 540 |
| CTCCATTTTC | CCACCAGATG | GAAGGACTGG | AGCTTTGTGG | ACAAAGATGA | GAAGGCCCGT | 600 |
| CTGCAGCACC | AGGTCACTGA | GGATGGAGAG | TTCTGGTGAG | TCCAGAACCC | AGGAAGACCC | 660 |
| AGAAGGGTAA | GGGTGGGGAA | GAGAGGGGAA | ATCTCAGACC | TCAGTCCCCA | GCTAAGGTTA | 720 |
| TCAGATTCCA | GCCCTTGGGA | GATCTTGGCT | GTGTTCTCCT | CCAGCCCAAG | GCCCAGCAAG | 780 |
| GATGAGGTTC | TGAGAGGAGC | CTTCCAGGCC | ACAGGGACAA | TGAGCCCAGG | ACCAGGCCAA | 840 |
| CATGACATGG | CTCTTGCCTC | CTGTGTGCCC | CTCCGCCACA | CACTCTATTC | CAGCCACAGG | 900 |
| CACCCTGGCC | TTAGCACAAT | TCTTTTCTGA | GCCTAGGAAG | CTCCACTTAC | CCTGATCTTC | 960 |
| CAACGTCAAC | CTCACCCTCT | CTCAGCTTGT | TTCTATTCAG | GCTTCAACTC | TCAGCTTAAG | 1020 |
| GAGAATTTTC | AAGTCTCAGC | TTAAGGAGAG | CCCCCTAAGT | TCCCCGAGGA | CTGGGATTAA | 1080 |
| TTTATGATGC | TCATCACCCT | TAAAATTGTT | TGCTTAAGCC | GGGCGCGGTG | GCTCACGCCT | 1140 |
| GTAATCCCAG | CACTTTGGGA | GGCCGAGGTG | AACGGATCAC | GAGGTCAGGA | GATCGAGAAC | 1200 |

FIG. 8C/1

```
ATCTTGGCTA ACACGGTGAA ACCCTGTCTG TACTAAAAAT ACACAAAAAA AGTAGCCGGG    1260
CGTGGCAGCG TGCGCCTGTA GTCCTAGCTG CTGGGAGGC TGAGGCAGGA GAATCACTTG     1320
AACCTGGGAG GCAGAGGTTA CAGTGAGCCC AGATTGCGCC ACTGCACTCC AGCCTGGGCG    1380
ACAAGAGAGA CTCTGTCTTG GAAAAAAAAA AAAAAATGTG GTCTTAGTTT AATGTCAAGG    1440
GAAAGGTTTT GGGTGTTTTT ATTACTTTAT TTTTTATTTA AAAACTATAA TAGAGACGGG    1500
CCTCGCTATA TTTCTCGGGC TGGTCTCAAA CTCCTGGGCT CAAGCGGTCC TCCCACCTTG    1560
GCCTCCCAAA ATGCTGGCAT GTGGGCCTGG TCAACATATG GGACCCCAAC TCTACAAAAA    1620
ATTTTAAAAT TAGCCAGATG TGGTGGCGTG TGCCTGTAGT CCCAGCTACT TGGGAGGCTG    1680
AAGCAGGGGG TCACTTGAGC CCAGGAGGTT GAGGCTGCAG TGAACTATGA TTGTCGTTCA    1740
CTTTTCTTCT GAACGTGAGA TTAAGTGTAG TCAGCAATTT GGCTTAGGAT TATTTATTCA    1800
GAATTTTTAA CCGTCACGTT GCGGCAAACC AGGT                                1834
```

FIG. 8C/2

(2) INFORMATION POUR LA SEQ ID NO: 4:

(i) CARACTERISTIQUES DE LA SEQUENCE:
        (A) LONGUEUR: 14664 paires de bases
        (B) TYPE: acide nucléique
        (C) NOMBRE DE BRINS: double
        (D) CONFIGURATION: linéaire (ii) TYPE DE MOLECULE: ADN (génomique)

(xi) DESCRIPTION DE LA SEQUENCE: SEQ ID NO: 4:

```
AGGAGGTGGA GGTTGCAGTG AGCCAAGATC ATGCCACTGC ACTCTAGCCT GGGCAACAGA      60
GCGAGACTCT CTCTCAAAAA ATACACACAC ACACACACAC ACACACACAC ACACACACAC     120
ACACACATAT ATATACACAC ATATATATAC ACACACATAT ACACACACAC ACGTCTGTAT     180
ATATATGTGT GTGTGTATAT ATACACACAC ACACTATTCT ATATATTCTT GTAGAGCTAT     240
GTGTGTCTCC TGTGCTATTG AGCATGAGCC CTTTTTTTTT TTTTTTTTTT TTGAGACAGA     300
GTCTCACTTT GTCGCCCAGG CTGGCATACA ATGGCGCAAT ATCGGCTCAC TGCAACCTCC     360
GCCTCCTGGG TTCAAGTGAT TCTCCTGCCT CAGCCTCCCA AGTAACTAGG ATTACAAGTG     420
CCCGCCATAA TGCTCAGCTA ATTTTTGTAT TTTCAGTAGA GATGGGCTTT CACCATGTTG     480
GCCAAGCTGG TCTCAAACTC CTAGCCTCAG GTGATCCACC TGCCTCAGCC TCCCAAAGTG     540
CTGGGATTAC AGGCATGAGC CACAGCACCC TGGTGAGCAC TAGAGCTTAT TTCTTCTATC     600
TAACTGTATT TTTGTATCCA TTAGCCACCC TCTTTTCATC CTCCCCTCTC CTTCCCTTCC     660
CAGCCTCTGG TAACCACTGT CTGCTCTCTA CTTCCATGAC ATATGCTTTG TTTTAGCTCT     720
CACATATGAG TGAGAGCATG CGACATTTAT CTTTCTGGCC CTGCACATT TTTGAATCAT      780
TGTTAGAAAA GATGATGGTT TGGAGTAGAT ACATCAGAAG TGACAGCGTT TGCCCTAAAA     840
AGGAAAGACA GGCTCCTCTG GGACCCTGAC CAAGTTCCTG TGAACTATTT TATTATTGTG     900
CTGTGTTAGT CCTGGGGTCT TCCGTTCCCA GCCCTCCTCA CCTGCTCCCA TATGGCTCTC     960
TCTCTTCTTC CAACCTCTCA GGATGTCCTA TGAGGATTTC ATCTACCATT TCACAAAGTT    1020
GGAGATCTGC AACCTCACGG CCGATGCTCT GCAGTCTGAC AAGCTTCAGA CCTGGACAGT    1080
GTCTGTGAAC GACGGCCGCT GGGTACGGGG TTGCTCTGCC GGAGGCTGCC GCAACTTCCC    1140
AGGTGGGAGA TGCTCTTGAT GGGGGAGGG TCTAAGCCGA AAAAGTTCCA GGCAGAAGAA     1200
```

FIG. 8D/1

```
GCCTAACTAG TGCTTATTAA GTCTCTCTGT TCCAGACGTC CACTATCTTA TTAAACCTTC    1260
CCTGTTTTAC TGAGAAGGAA ACCACCATGC TGAGAAGTTT GCAATAGGGA GCTGGGTAGC    1320
AACTTTGGAA GCAGGAACTT GTGGGAACAA TGCAGATGCT GCTTGGACTT ACGATGAGGT    1380
TATGTCCAGA TAAGCCCATC CATCTTTTGA AAATACCCTA AGTGAAAAGT GCATCCAATA    1440
TGCCTAACCC CCCAAACCTC ATAGCTTACC CTGGCCTACC CTCAAACATT GCTCGGAACC    1500
CTTGACCTTA AGCCTAAAGT TGGGCCAAAT CATCTAACTC CAAAGCCTAT TTTACAAAGA    1560
AAGTTGTTGT AATATCTCCA TGTAACTTAC TTAATACTTG TACCTAAAAA GTGAAAAACA    1620
AGAATGGTTG TACGGGTACT CGAAATCCAG TTTCTACTGA ATGTGCATCT CTTTCACATT    1680
GTAAAGTTAA AAAATTGTAG CCGAACCATC CTAAGTCAGG GACTGTGAGT ACTGTGTCAG    1740
TAACAGTAAG GGCACTATTG GAGAACCAAG TTAGCAGCTG CTGCAATAGT TCAAGTCAGA    1800
GATGATGAAA ACCTAGACCA AGTCAGTAGC AGCAGAGATG GAGGGAGAC AGCAGATTTA    1860
GGGAGAGCAT ATTGGGTGAT GTAGGGAAGG AAGAAGAATG ATGTCAAGAT TCCCAGTTGG    1920
GGACCTGACA ACATTGCAAC ATAAGACACA CAAGAAGATC GGGTGGGTGG CTCATGCCTA    1980
TAATCCCAGC ACTTTGGGAG GCAGAGCCAG GAGGATCACT TGAGCCCAGG AGTTCAAGAC    2040
CAGCACAGGC AACATAGTGA CACCTCATCG TTACCCAAAA TAAAAAAAAA AATGAGGTGG    2100
GAGGATTGCT TGAGCTCGGG AGGTTGAGGC TACAATAAAC TGTGATCATG CCACTGCACT    2160
CCTCCCTGGG TGACAGAGTG AGACCCTGCC TCAAAAAAAA AAGACACACA AGAGAAAAAT    2220
ATCAGCGTGT TGTTTGTTTT TGGTGGAGTT AATTGTGGGG TTCTAGGGAA AGGAATTTAG    2280
CTTGGGACAT GGAAAGTTTG AGGTTCCTGT AGAGTGTCCC AGTGAAGATT TGTAATAGAG    2340
CATCGGATGC GCATATTAGA TGGCACTTGG TGATATGATA AGAACTCAAA AAATATTTGA    2400
GGAATAAAGG AAAGAAGAGG CCAGACGTGG TGGCTTATGC CTGTAATCCC AGCACTTTGG    2460
GAGGCTGAGG CAGGCGGATC ACTTGTGGTC AGGAGTTCGA GACCAGCTTG GCTAACATGG    2520
TGAAAACCCA TCTCTACTAA AGATACAAAA ATTAACCGGG GATGATGGTG GGTGCCTGTA    2580
ATCCCAGCTA CTTGGGAGGC TCAGTCAGAA GAATCGCTTG AACCCAGGAG GCGGAGGCTG    2640
CAGTGAGCCG AGATCGCGCC ACTGCACTCT AGCCTGGGCA ACAGAGCCAG ACTCCGTCTC    2700
AAAAAAAAAA AAGTGAGAGA GATTGAGGCT GGGATATATG GCTCAGGCAT CATGCGCGTG    2760
TAGGGGGCAG TTAAAAAGCA GAAGTAAGAA AGATTGCCTA GGGAGGCAGG AAGGGTGAGG    2820
```

FIG. 8D/2

```
TGAGAGGAGA AGAGGCCCAG GACCAGATTC TAGTCACCAA CAGCGTTTAA GGGGCAGGTA    2880
AGGAAAACAA AACCATCAGC AAAGACTGAG AATGAAAGCC CAGAGAGGAA GGAAAAGCCA    2940
CACATACAAT CAGTACAGCT CCATCTGAAT AAAGGTAGCG CCCCCCCCCC CCCAAATCAT    3000
TAGAGAAATG CCTGATTCGG TTTTCTGTGG ATTTTTCCTA AGAACCTAGA TGTGGGGAAT    3060
AGAAATAAAT GGTTCCCTCT GTCTCATCCC CTCCCTGCCC TCTGAGAGGA AGCTGTGATT    3120
GCGTGCTCCC TTTCTGGGGG TGCAGATACT TTCTGGACCA ACCCTCAGTA CCGTCCGAAG    3180
CTCCTGGAGG AGGACGATGA CCCTGATGAC TCGGAGGTGA TTTGCAGCTT CCTGGTGGCC    3240
CTGATGCAGA AGAACCGGCG GAAGGACCGG AAGCTAGGGG CCAGTCTCTT CACCATTGCC    3300
TTCGCCATCT ACGAGGTGTG TAGTCCTGAT TGGCTCCAGC CCAGGAAACA TACTTTCCCA    3360
GAGAGGACGC TTCCAGGGGC TTCTAGAGGG GCCCTCTGCT TCCTCAATAC CAGTGACCCA    3420
CAGAGCTCCT GGTATCAGGA CCACTTGTGT TTGTAACAAG CAAAAAATAC CAGGGGGGGC    3480
ATTAGAGAGG CAGTGGAGCG GGCCTGGCAG AACAGGTGCC TGGGGGTCAG GCTTCCGCAT    3540
GCGGGCTGCA GTTGCTGGCA TTGCCTTCCG CAGGCTCCTC ATCCTCATTC ACATCTGAAG    3600
CATCTTCCTT TCTGTTTCTT CTCAAGGTTC CCAAAGACCT ATAGCAGCAG CAGCGGCCAG    3660
CAGTTGTGTG CAGCACTACC CAGGGGGGCC CGAGTCTGTC TGTGGCTCGT CGAGAAGCTT    3720
CCTGGTCGGG TTTGTGGGCA GGACTTGTGA TAGGAGAGGG CCTTGCCTGT TGTTATTTCC    3780
CACTTGCAGA GCAGGTTGCC TCAGGGCATT GCATGACCCA TGACTACCAC CCCCAGGATG    3840
TGCACTTTCT CCCTCGCACC AGACACTGCA CGTCACACAC ATGCCTTTGC ACACTCACCC    3900
TCCTCCACGC TTACAGCCAC ACACACAGTC ACACAGACGC GTTCTGAGGG TGCCTGCCCG    3960
CTTGGGATGG AGGAATCACT TCCCTCAGAA CCCAGCCAAG TCCTCTAGGC CTCCTTGGGG    4020
GTCCTTCCAG CCTGAGGGGC TTCGGAGCTG AGGACAGCTG TTCTGGTAAG TGTCCCTGAC    4080
TGTGGGGATG ACACATTTCC ATTCACTCTG AATCACAACA GAAAGCGGAA GAGGAATTGA    4140
GGTAGGGAGC CTATTTAACC CTTGGGAGTC GGGAAGTAGG GAGGTTGAAA CTGTGACATG    4200
GGTGACCAGG GAGTTGGGAA GGGACCCTTG GAGGTGGCTG TGGCAGGACA GGACGTTCCT    4260
CCCGAGGGGC TCATGTGCCC TGGGCTCTCC CCATCTCTCA GATGCACGGG AACAAGCAGC    4320
ACCTGCAGAA GGACTTCTTC CTGTACAACG CCTCCAAGGC CAGGAGCAAA ACCTACATCA    4380
ACATGCGGGA GGTGTCCCAG CGCTTCCGCC TGCCTCCCAG CCAGTACGTC ATCGTGCCCT    4440
```

FIG. 8D/3

```
CCACCTACGA GCCCCACCAG GAGGGGGAAT TCATCCTCCG GGTCTTCTCT GAAAAGAGGA    4500
ACCTCTCTGA GTGAGTGCTG GCCCAGCTTT CCCACGTGTT TCTAAAAGCT CACATGGCCC    4560
ACTCCAGAGG TTGAAGGCAT GAGGCAGCTA GACACGTCTC CTCCAGGGTC CTTCTGCTGC    4620
TCCTGAGCCA CTGGCCACAT TACCCCCATT CATTCATTCA TCCATTCTGT GATATTTATT    4680
GAGCACCTAC TATGTTCCAG GCACTGTCCT AGGCACTAAG GATAGAGTAG TGAAGTAAAC    4740
AGAAAGAAAT CCCTGCCTTC ATGGAGCTTA ATATTCTAAC ATGAGACAAT AATGGATAGG    4800
AAAAACATAT GTAGCATGTT AGATTTGGAG AGGTGATATG GAGCAAAAAT AAAGTAGGGA    4860
AGAGGGATAG GAGGTGTTGG GGATGCTTGA AATTTTAGGT TAGCATGGCC AGGAAAGCCA    4920
CATCCTGTCC CTGGCCACCA CAGATGAGCT CATAGCCCCT GCCACTCTGA TCTCTGTCCT    4980
TGGAAGATGC ACCAGGTCCA TGGGTAGGTG GCTGGGTCAT GCCTTTGGGG GGCTCTGAGC    5040
AATACTAACA AGAACCTGCG TGCCTGGGCT TGCCTGTCGG GGATGGTGCT GACATGGGGC    5100
TGGTTCCTGG GGTTGGGGTG TTCCAGGGGT TCTCTAGAGG CTGGTTCTGG CTTGGCTGCC    5160
AGGAAGCCGT GCACCAGAGC AAACCGTCCA CGGGCCTCCT GCTTGCTTCT GGTGACACTG    5220
AGACCCCACA TGTCTGTATT CCTCACAGGG AAGTTGAAAA TACCATCTCC GTGGATCGGC    5280
CAGTGGTGAG TGGTTTAGAT CTTCTGTGCG AAAAGTCCAG AGGGTCCCCT TCCTGACCA    5340
TGCAGGGGAC AGATGGTGCA GGGGAGAATG GCCACTGGCA GAGGGAATGG GAGTCTGGGC    5400
TGTGCTGAGC AGTCCCTCCT TGGCACTGCA AATCCTACTT TGGCATGGCC AGAAGTAATC    5460
GGCCTTAAGC ACCGGGGGCC ATTGAGGCAG TTCAGGGGCT GGGAAATATG GAAGAGGGTC    5520
CTGGAAAGGA GAAGCAATTT GAACAATCGG AGGGAACAAG GCCACAGGAA GGGATGACAA    5580
GAGCCGCAGC GAACACTGGA TTCTGAGACT GGATAACATT GGATTTCACA CATAGAGAAA    5640
AGAAAGTAAG CTGGTGCCGG ACCTGGTGTT GACACTTGGA TCCTCCACTT ACCAGCGGGG    5700
TGACCTGGAC AATTTCTGTA ATCCCTCTCA CTCAGTTTCC TACTCAGTAA AACGGGGATG    5760
ATAATGTGCC TTGCAAGGCT TTTGTGAGGC TTCATCAATG ACGTGATGTA TGTGAAGTGT    5820
CTGGCACAGC ATGGGCACTC AAACAGAGGT GCTTTTTCAC ACTTTACACC TTACAAGGTA    5880
CTTTTCACAT GTCTCATCGC GATACTTGCA AGGTTGCTGA GAGGTAGATC GGGTTATAAT    5940
CCCTGGTGTT CAAGAAAGGA AGCAGAGGCT CAATGGGGTT GAATGACTTC TCTGAGTTCA    6000
CAGAGCTCAG TAAGTGGCAG GGTTTGGAAC TCACATTCAG ACTCTCTGAC TCCAGACTTA    6060
```

FIG. 8D/4

```
GGTTTTTCCG CACCTCCACG CTGAGGCCAG CCCCAGGCAG TGAGAAGCCC AAAGTCCGAA    6120

GCACAGAGTG CTGTGTGTTG GGCTCTGTGT GTTGAGGAGT CTTGTGACTG CCTTGGGGCT    6180

TTGGGCTGTA GTCAGCTGAC AGTCCTTTGT GCTCTGTGGG GATGACGTAG GCCAATGGGA    6240

GGACAAATGC CCCTCTGAAC TGTCTTCTGG GCAGTGACAG TCATGGTCAT AATCCTGACC    6300

CTGAGCCAGT GCCAGGTCTC CAAGTGCCTT CTGAATGACC ACAGGCGATT GGTTTTAGTC    6360

GTAGGTGCGT GGGGATCTGT TCTGGTCATC TGGATGCTGG TCATCGGGTG CAGTATTGAT    6420

CAGGACCTGC AAACCCAAAA GCTTATGGGA GCTGGCACGT CACGTGAGTA GAGCAGGCAG    6480

GTGCAGCGTT TTTGATGTCC CTGCACTGAC ACAGTTGTCT GCAGTTCTCC AATTTGACAT    6540

TTGGGCTCCA GTGTCGAGGG TCAAACAAGG AATTTTGGGG CGTGGGCCAA ATCTGGGAAG    6600

ACACAGGGAG CAGGGCCCTT TGGCTCAAGC TGATAGTTGC CGCAGGGATT ACCAGGCCCA    6660

GGGCAGCCTG CCACAAGCTG GGGCTTTTAC CAAAGAAAAT CTCCCTATGT TAAATGCTTG    6720

CTCAAAAATT TTTAAAAAAT ATTCTGTAAG TCAAAATCCA TTGTTAGGTC AGTTTGAGAG    6780

AGCCATGTTT TTGGTGTTTT AGTAACCAAT TTCATTTTTT TATTATTTAT TTATTTGTTT    6840

ATTTTTGAGA CGGAGTTTCA CTCTTGTCAC CCAGGCTGGA GTGCAATGGC ATGATCTCAG    6900

CTCACTGCAA CCTCCGCCTC CCGGGTTCAA GCAATTCTCC TGCCTCAGCC TCCTGAGTAG    6960

CTGAGATTAC AGGTGCCCAC CATCACGCCT GGATAATTTT TGTATTTTTT AGTCGAGATG    7020

GGGTTTCACC ATGTTGGCCA GGATAGTCCT GAACTACTGA CCTCAGATAA TCCGCCCACC    7080

TCAGCCTCCC AAAGTGCTGG GATTACAGGC ATGAGCCAGC ACGCCCGGCC ACCAATTTCA    7140

TTTTTTAAAA AAGGAAGAAA GAAAACCTTA GCCAGAAGAT CTTTTTCCTT GCCATATGCA    7200

GTAAGAGTAG ATTATAAAAA CAAAGTCAGA GCAGTCACTG GTGTCTGGGC ATGGAGGAGA    7260

AAGAAGAATT CTCTTCTCCC TTCACCCTCC ATCCCCTTT TTGGCTCCAT GTGATTCAGA    7320

TTTCTGGACC CTGGAGCCCC ACCCAAGCT AAAGACCAGG ATACAGGGAA GCCACAACCA    7380

CTGGCGGTTC TGAGAACTTA CTTTTCACTT ATTCTGCATT TACTGTTTCC TTTTCTTATG    7440

CAGAAAAAGA AAAAAACCAA GGTAGGTGTG TGGGTAGAGA GCATGAAGTG TGTGTACTCA    7500

TGCATATGTA TGTGCATGCA TGTGAAGTGT GCATGTGTGA GCTCATATGC ATCCATGCAC    7560

CAGACTTGCC TCTTCCTCCC CCTCCTTCCT GAGCTTCTGC TGCGGCCGAG CGTGCAGTAA    7620

TGACAACTAC GATTTGCTGG GGGAAGGCTA CGTGCCAAGC ACTCTTTTAG GTGCTTTCCA    7680
```

FIG. 8D/5

```
TGATTAATTC CTTCCTCACA ACAGCCCTAT GAGATTAGTA CTATAACTAT CCCCATTTTC    7740

AGAGGGAGAA AACGTACAGA CTTGACTAAC TTGCCCAAGG CCACACAGCC AGAGAGGGGC    7800

AGAGCCACTA CTTAGAGCCA GGCAGTCTGG GTCCAGAGTC CGTGTCCTGA ACCACAAGAG    7860

GCCATCATAC GCCATCAGAT TTGGTGCTAG CATTTCTGGT GGTGCCTGGT GGTGATGGAT    7920

CCATCACAGG GGTCCTCCAG GTACTGGTGC TGGCCCAGAC CAGAGCTGAC ACTCCTCAGG    7980

CACTACCACA TTCCAGGCAC TGTGCTTGGG GTCAGTCCCT CTCTTTTTTT TCCCCCCCAA    8040

TTATAACAGT ATCTACAAAG TAGGTGCTGT TATTTTTCCC CTTTCACAGG TGAGATAGAC    8100

TCAAAGAAGT GAACTTGCCC AAGGAACAGA ACTAATGAGT GGGGAAAATG GAACTGGAAA    8160

CCATGTCTGT TTACTCCAAA ACCTGTGTTT CTTGCCCTCT TTCTCTGATG CCAGCCCCCT    8220

ACACTTCAAG GCCTGTGTTG TCCAGACCCA CACTCGGGCC TGCCAGTGTG TGCCTGGCAG    8280

GGATGCTCCA TGGCCACACC ATATCCATCC TACACATCCC CCTCAGACT GTGACCTCCA     8340

TTTGCTCTGG GATCCCCACA AGCTTCAGCT GCTTGAGCAA GACACTGCTT AGAAGGCAGA    8400

GCAAGCCAAG GCCTCTGGGG CCTGCTGGGA GCCAAAGCTG GGAGCCGTT TCCACGGGTC     8460

TATCTGCTTG ACCTGTCCTA GATGAGCAGC ATGGAAGGCC AGTGGTGCAT GAGTCCAGGC    8520

GGGCTGCTTT TCTGCTCCGA GAGGCTCTGC CTGCCCAGTT GTTCTCTGCA TTGCAGCCTC    8580

AATCCCCACA GCCTTGCCTT CCCCCGGCTT TCCCTACAGG TGCACCGCAT CCACAGTGTT    8640

GGCACCATGC ACCAGCCGCT CTCCGTCCTT TTCATATCCT TGTCACTTGC ACGAGCATGT    8700

CTTGAAAATA TCCCTTGTTT GTGTAGCATC TTAAATGTTT TTGCAGTATG ATTTTGCATT    8760

CAGTATCTCA TTTGATCCCC ACAAGAGCCC TATGAGGAGG GAAAGCAGAT TTTACCATTA    8820

AAGGATGAGT AAACTGAGGC CAGAGAGGAT ATTTTTGGTT TTTTTTGAGA CAGTCTCACT    8880

CTGTCACCCA GCCTGGAGTG CAGTGGCTTG ATCTTGGCTC ACTGCAAGCT CCACCTCCCA    8940

TGTTCACACC ATTTTCCTGC CTCAGCCTCC CAAGTAGCTG GGACTACAGG CACCCACCAC    9000

CACACCCAGC TAATTTTTTT GTATCTTTAG TAGAGATGGG GTTTCACCCA GTTAGCCAGG    9060

ATGGTCTTGA TCTCCTGACC TTGTGATCTG CCTGCTTCGG CCTCCTAAAG TGCTGGGATT    9120

ACAGGCGTGA ACCCCCTGC CCGGCCAGAG AGGATATTTC TTAATGACGG GCAGGGCTGG     9180

GATTCCAGCC CAGTGTTCTG ATGGCTCACC CACTGACCAT TCCACTAATC CGTGTCCTTT    9240

TTCAATCTAA ACTTTCAGGG TTGTAGAGGT TCCTTTGAGG TGCCTCAGTA CTTCCATGGT    9300
```

FIG. 8D/6

```
GATGTGGGGT CTGAGCGCCA AGAGCTCTGT TCTCATTAAT CAGAGAAGCT TGTGTTTTTA   9360
AAAACACCAT GTTTACTGCA GGAAATTTAA TTGGACAGTG TTTCCATCTG GAAAAAAAAA   9420
AGTCTACAAA ATACTTGACA ATCACTGCAC TAGATCATGC TGCTTTTAGC ATTCTTAGCA   9480
TTTCACGTGC TGAGCTCTCA ATACTCTACC ATGAGGAGGG ATGGAGTGGG TATGAAAAGA   9540
TAAAGAACTG AAGTCACACG GCTTGTCAGT GGCAGAGATA GAGCTTGAAC CGAGGTTGAA   9600
GAGCTCCCGC CTATTCCTTT CCTCTTCTCA CTGGATAAAG CTGCTCCAAG AGAGGTGCTG   9660
CCTCAGTGTG CCTGTTCAGA CTGTAATCCT CCCTTCCTTC CTGCCTCCTC CCTCCTCTCT   9720
CCAGCCCATC ATCTTCGTTT CGGACAGAGC AAACAGCAAC AAGGAGCTGG GTGTGGACCA   9780
GGAGTCAGAG GAGGGCAAAG GCAAAACAAG CCCTGATAAG CAAAAGCAGT CCCCACAGGT   9840
GTCTGGGCAT GTGGCATGGG TGGGGTGGCC AGCACGCTAC AGGGGCTTCC TATGCGCTTG   9900
GGATACACAG GGGCTGGAGG CTTCCCAGGA GTTTGTCTTG AACATCTGGA GGTTTGAATT   9960
TGTCCCACTG ACCTTTTCTT TCAGCAAGTT CCCCTGAAAT TGGGCTGCT GCTTGGGTGA    10020
ATATCCCAGG ATGGGGGTTC CATTCTAGGA GTGGACTGGC AGGCTGAGCC TCCCATGGAG   10080
CTGATCCAGC CAGGATACAG AGAAGGGGAG GCAAAGGCTG AGACAGAACC AGCTTGAGAG   10140
CGGAGGCGCA ACTCTTGTCT CCTGGTGGCC TTGAGCATTT CACAATAGGG GGATAAAGGA   10200
TAGGAGCAGA AAAGTGGGGC TGACTTCAGA AATGGGGTCC TCTAGAGCTC ACGGGAGGGT   10260
GTTAGATTGG AGTGGGAGCT TAGTGGAGGT GAGCCTTAGA GGCAAAAGTC TCCAGACCAA   10320
TCCAGCCCCC CTCTTCTATC CGGGGGCCCC TCTTCTATCC AGGGCCCCTC TTCTGTCTGG   10380
GAGCCCCTCT TCTATCTGGG GCCTCATGCA GTGGGGCCTA GGGGAGGTTC TCTGAGGACT   10440
TGGCCTTGAT GACAGGGTGG CTGGAGGAAT CAGAACGGTC AGACCTTCTT TGACCTGCGG   10500
GCACCTTTAG TTCGAATGCT CAGGCCTGGG ATGGTGGAGG GGCTCTTCC AGGTCGGGAC    10560
TGGGGTGGCG GGAGGACGC TGTATGGCCG CCATATCTCC TTTGGCTGGG GGCGTCAGGG    10620
CTGGAGAGGT GTGAAGAGTC CCTGACGCCT CGATGCATCT CACTCCAGCT CACCAGGTCT   10680
GCATTTGCCC GTCCCCAGCT CCTGCTGCCA CCCCCGGCCG TTTTAGGCAC TTGGCTCCCT   10740
TGGCCCAGAC GAGCTTGCCT CACAGGCCTG TGCACCTCTG ACCCCTGTCA ACCAGTTTTC   10800
CTTTGTGCCT CCACAGCCAC AGCCTGGCAA CTCTGATCAC GAAAGTGAGG AACAGCAACA   10860
ATTCCGGAAC ATTTTCAAGC AGATAGCAGG AGATGTGAGT ACCTCCAAGC CCAGGACGCC   10920
```

FIG. 8D/7

```
CACAGGTGCT TCCTTCTCTC CTGGATTAAC TGCTCAGATT ACCAATTATT TCATTATTGT   10980
TTGCTAGAGG TCACTTTGGA CTTCGGTGGA GCCAGGGGAT GTGTGCGTAG CACACAAATC   11040
CACAAGCCCT TGAGTTTTGG ACTGCCACGT CTGCTGGGGG GCTCAGAGGC CTTTTTGCTC   11100
TGAGCTGCCC ACGGTGGTCC TGATAGCTGA GGTGCAGTAT CTGGCCCCCT GTCTTCCTCA   11160
GAAAAGCCCC AGCTTCCCAT GACATAATAG CACCGACAGG GATTTTACAA ACACAGCCAG   11220
GTGGAATTTG TTTTGCAAAG TGTCCGCGCC AGGAGCTGCT GTACTCCTGA ACCATGACCC   11280
TCCTCTCCCT TCCTCCTCAG GACATGGAGA TCTGTGCAGA TGAGCTCAAG AAGGTCCTTA   11340
ACACAGTCGT GAACAAACGT GAGTTGCTCA AACCAAATGG GGGTGGGGTG GGTGGGGAGT   11400
CCCGTTGTCT CAAAGCAGCT CCTCACTCTT CTCCATCCCC CCAGACAAGG ACCTGAAGAC   11460
ACACGGGTTC ACACTGGAGT CCTGCCGTAG CATGATTGCG CTCATGGATG TATCCTTCCT   11520
GCCGCCCCTT CCCGACCCTC TGTCATCAGC CCACGGGGC CAAGGCAACA TACAGGGTGC    11580
CCAGTCAGGC AAACGGCCCT AATTTGTGCC CAGGGAAACT TAAGGAGACC CTGATTCAGA   11640
ACATCTTGGA TACTCGTCTG AAAGGGGTTG TTAGAGGCGG AACGGGAGGA TGTTCGGTTC   11700
TAACTGCCCT AACCCCTGTG CTTCTCTCAG GCCTGGGATC CTGCCCAAGC AAAAGTGGTC   11760
CTTAGGAGAG CGGCTCCTGG GTTACAGAGT AGGCGCAATC TCTGACTGGT GGTGGAGTGC   11820
AGGGGAGGGT TAAATAGTAC AACAGGGCAG TGGGTAGGAC AGCCCGGAGT CTCCTAGACC   11880
CTCCCTCCAA ATCCAGGCCG ATTTTGCTGT GTGCTGTGTA GCCCTGACCT CCCTCCTCCA   11940
GACAGATGGC TCTGGAAAGC TCAACCTGCA GGAGTTCCAC CACCTCTGGA ACAAGATTAA   12000
GGCCTGGCAG GTGGGAAGAG AAAATGAAGC GTGGGAGTCA AGAATGGGGT TGATTTGGAC   12060
ATTCAGTGTG TGACCTCCAT CCTCAAATTT TCTATTGCCA GAAAATTTTC AAACACTATG   12120
ACACAGACCA GTCCGGCACC ATCAACAGCT ACGAGATGCG AAATGCAGTC AACGACGCAG   12180
GTGCTGAGAA GGAAGGGGTG TCAGGGATGT GGACCCGAGA CGGTGGGAGC AGGAATGGGA   12240
GGGGACTAGC TACTAGGGCC CCACTAGAGA AGGAGAGGGA AACGGCTTCT CACTTTCCCT   12300
TCCCAGGTCA CAGAGTGTCC GAGAGGCAGG GAAAATAGAA GACAGGCCCA AGGCCTCCAG   12360
CTCCACGTCC ACCTCTAACA TGGTCCCCTC CACAGGATTC CACCTCAACA ACCAGCTCTA   12420
TGACATCATT ACCATGCGGT ACGCAGACAA ACACATGAAC ATCGACTTTG ACAGTTTCAT   12480
CTGCTGCTTC GTTAGGCTGG AGGGCATGTT CAGTAAGTGG GAGAGGGGGG CTGCCCTCTG   12540
```

FIG. 8D/8

```
CTCTCTTGCA GGGGCAGTTG TGGCAACAGG CATCTCACCT GATAATCTCC AGTCTGCTCC   12600
ATCCAGGCTG AACAAGGGCC AATGACCTCT TTAGGCCCAG AATGGGATGG CAAAGGGAGG   12660
GTTACTGGTG ATTCTCTGCC TGCACATCTT TGTGCTGATG AGGGACAGCA CTGGGCACAC   12720
GGTCCTCTGA GGGGAAGTTA CAGTAGTAGA GGCGGAGTGC GCCTGTAACT GGCCTCTGCC   12780
CTGTCCATTC TTTCACAGGA GCTTCTCATG CATTTGACAA GGATGGAGAT GGTATCATCA   12840
AGCTCAACGT TCTGGAGGTA AAGCATAGGC ACAGCACATT CCCCCTACAC ATTAAAACTC   12900
AAGGTGGAGG GGTCAACGGC GCGGACTGGA CCCAGGGTGT GCTCCTCATT TCCACACAGT   12960
GGTGGAGGGA AGGGATAGGA ACAGAACATG GAGGGAGGCT CAGCAGGCTC CCAGGACACA   13020
TGCACTTGAG GCCCAAAAGG ACCTCTGCTC CCCCAGTCAC TTGATGCGGG AAAACATGCA   13080
CCTTCTTAGG GAAGATCTAG GAGAAAGGAA ACAGTAAGCC ACTGCTTCTT GGAAAATCTT   13140
CTGGGGGTCT GACCTGCTGG GACTGTTCCC TTTCCTCTTG CCCCGTAAGA TTCCTAGGGC   13200
GGGGGGGGGG CGGGGTCACT CTTTTCTGAT CTACATTCTG ATCTTGGGAC TTCTTTCAGT   13260
GGCTGCAGCT CACCATGTAT GCCTGAACCA GGCTGCCCTC ATCCAAAGCC ATCCAGGATC   13320
ACTCAGGATT TCAGTTTCAC CCTCTATTTC CAAAGCCATT TACCTCAAAG GACCCAGCAG   13380
CTACACCCCT ACAGGCTTCC AGGCACCTCA TCAGTCATGT TCCTCCTCCA TTTTACCCCC   13440
TACCCATCCT TGATCGGTCA TGCCTAGCCT GACCCTTTAG TAAAGCAATG AGGTAGGAAG   13500
AACAAACCCT TGTCCCTTTG CCATGTGGAG GAAAGTGCCT GCCTCTGGTC CGAGCCGCCT   13560
CGGTTCTGAA GCGAGTGCTC CTGCTTACCT TGCTCTAGGC TGTCTGCAGA AGCACCTGCC   13620
GGTGGCACTC AGCACCTCCT TGTGCTAGAG CCCTCCATCA CCTTCACGCT GTCCCACCAT   13680
GGGCCAGGAA CCAAACCAGC ACTGGGTTCT ACTGCTGTGG GGTAAACTAA CTCAGTGGAA   13740
TAGGGCTGGT TACTTTGGGC TGTCCAACTC ATAAGTTTGG CTGCATTTTG AAAAAAGCTG   13800
ATCTAAATAA AGGCATGTGT ATGGCTGGTC CCCTTGTGTT TTGTTGTCTC ACATTTAGAT   13860
ATCAGCCATG CATGACTGAA TGGCTTCCAA TCATATACTC ACCTATCACC TACAAGAGAA   13920
CAATGAAAAA CACACACAAA AACAAAATCT TGAATTTTGT AATCATGCCT ATTGCTATTT   13980
CTTGAGCATA AGAATGGCTC AGATACTTTC CAAGACATAA AAGGAAGGCA GAGGAATAGT   14040
TGTTGCTGTA AAAGACATCA AGAATAAATG GGGTCATGTA CAACGGGAGG GGCCGGTTAC   14100
CTGAATAATG GAGTGGAGAT TGAGCTATCC TAGCTCCTCT GCTCACTAAC TGACCTGTCG   14160
```

FIG. 8D/9

```
CATGACCGTG GACAAAACCC TGAACGCAGC TGTTTGTTTG CTAAACTTCT CTGGACCATG    14220
GCCTGCGGCA TATCTATAGG CATCCTGTGT TTTCCACCCA GTTTCCTTCT TCCTCGCTAA    14280
GCCAACGTGG AAAGGGCTGG CCGTGAATAT GCAGACAAGG TAACGAAAGT AAACCGTCAA    14340
TTAGTAAAAG TACTTCATTT TCCTCTTGTA TTTGCTTCAT TCTTGCTTCA CAAAGTTACG    14400
AAGTCCACAG CTTTATACCA AAATGTAAGA AGGCTATTTG CTTATAAACA TTTTGAGTCA    14460
GGTGTCATCT GATTTCATTC TTCTAATCCA TATTCAATAT TAAAAAATCA GAAACCAAGG    14520
GTGCTGGAGC AGCTCTAGGG CATATATTTC TCTTAAATAG GAGAAAGATT TTCAACAGCT    14580
TTTCCTCCTT GACCCCCTCC TTTCCCAATT TATTTGGGTC ACTACCTTGA ATTTAGAGTG    14640
AATCTGGGAA ATGTAGTCAC CAGG                                          14664
```

FIG. 8D/10

LGMD GENE CODING FOR A CALCIUM DEPENDENT PROTEASE

The invention relates to the isolated gene coding for a calcium dependent protease belonging to the Calpaïn family which, when it is mutated, is a cause of a disease called Limb-Girdle Muscular Dystrophy (LGMD).

The term limb-girdle muscular dystrophy (LGMD) was first proposed by Walton and Nattrass (1954) as part of a classification of muscular dystrophies. LGMD is characterised by progressive symmetrical atrophy and weakness of the proximal limb muscles and by elevated serum creatine kinase. Muscle biopsies demonstrate dystrophic lesions and electromyograms show myopathic features. The symptoms usually begin during the first two decades of life and the disease gradually worsens, often resulting in loss of walking ability 10 or 20 years after onset (Bushby, 1994). Yet, the precise nosological definition of LGMD still remains unclear. Consequently, various neuromuscular diseases such as facioscapulohumeral, Becker muscular dystrophies and especially spinal muscular atrophies have been occasionally classified under this diagnosis. For example, a recent study (Arikawa et al., 1991) reported that 17% (out of 41) of LGMD patients showed a dystrophinopathy. These issues highlight the difficulty in undertaking an analysis of the molecular and genetic defect(s) involved in this pathology.

Attempts to identify the genetic basis of this disease go back over 35 years. Morton and Chung (1959) estimated that "the frequency of heterozygous carrier . . . is 16 per thousand persons". The same authors also stated that "the segregation analysis gives no evidence on whether these genes in different families are allelic or at different loci". Both autosomal dominant and recessive transmission have been reported, the latter being more common with an estimated prevalence of $10^{-5}$ (Emery, 1991). The localisation of a gene for a recessive form on chromosome 15 (LGMD2A, MIM 253600; Beckmann et al., 1991) provided the definitive proof that LGMD is a specific genetic entity. Subsequent genetic analyses confirmed this chromosome 15 localisation (Young et al., 1992; Passos-Bueno et al., 1993), the latter group demonstrating genetic heterogeneity of this disease. Although a recent study localised a second mutant gene to chromosome 2 (LGMD2B, MIM 253601; Bashir et al., 1994), there is evidence that at least one other locus can be involved.

Genetic analyses of the LGMD2 kindreds revealed unexpected findings. First genetic heterogeneity was demonstrated in the highly inbred Indiana Amish community. Second although the Isle of la Réunion families were thought to represent a genetic isolate, at least 6 different disease haplotypes were observed, providing evidence against the hypothesis of a single founder effect (Beckmann et al., 1991) in this inbred population.

The nonspecific nosological definition, the relatively low prevalence and genetic heterogeneity of this disorder limit the number of families which can be used to restrict the genetic boundaries of the LGMD2A interval. Cytogenetic abnormalities, which could have helped to focus on a particular region, have not been reported. Immunogenetic studies of dystrophin-associated proteins (Matsumura et al., 1993) and cytoskeletal or extracellular matrix proteins such as a merosin (Tomé et al., 1994) failed to demonstrate any deficiency. In addition, there is no known specific physiological feature or animal model that could help to identify a candidate gene. Thus, there is no alternative to a positional cloning strategy.

It is establishes that the LGMD2 chromosomal region is localized on chromosome 15 as 15q15.1–15q21.1 region (Fougerousse et al., 1994).

Construction and analysis of a 10–12 Mb YAC contig (Fougerousse et al., 1994) permitted the mapping of 33 polymorphic markers within this interval and to further narrow the LGMD2A region to between D15S514 and D15S222. Furthermore, extensive analysis of linkage disequilibrium suggested a likely position for the gene in the proximal part of the contig.

The invention results from the construction of a partial cosmid map and the screening by cDNA selection (Lovett et al., 1991; Tagle et al., 1993) for muscle-expressed sequences encoded by this interval led to the identification of a number of potential candidate genes. One of these, previously cloned by Sorimachi et al. (1989), encodes a muscle specific protein, nCL1 (novel Calpain Large subunit 1), which belongs to the calpain family (CANP, calcium-activated neutral protease; EC 3.4.22.17), and appeared to be a functional candidate gene for this disease.

Calpains are non-lysosomal intracellular cysteine proteases which require calcium for their catalytic activities (for a review see Croall D. E. et al. 1991). The mammalian calpains include two ubiquitous proteins CANP1 and CANP2 as well as tissue-specific proteins. In addition to the muscle specific nCL1, stomach specific nCL2 and nCL2' proteins have also been described: these are derived from the same gene by alternative splicing. The ubiquitous enzymes consist of heterodimers with distinct large subunits associated with an common small subunit; the association of tissue-specific large subunits with a small subunit has not yet been demonstrated. The large subunits of calpains can be subdivided into 4 protein domains. Domains I and III, whose functions remain unknown, show no homology with known proteins. Domain I, however, seems important for the regulation of the proteolytic activity. Domain II shows similarity with other cysteine proteases, sharing histidine, cysteine and asparagine residues at its active sites. Domain IV comprises four EF-hand structures which are potential calcium binding sites. In addition, three unique regions with no known homology are present in the muscle-specific nCL1 protein, namely NS, IS1 and IS2, the latter containing a nuclear translocation signal. These regions may be important for the muscle specific function of nCL1.

It is usually accepted that muscular dystrophies are associated with excess or deregulated calpains, and all the known approaches for curing these diseases are the use of antagonists of these proteases; examples are disclosed in EP 359309 or EP 525420.

The invention results from the finding that, on the opposite to all these hypothesis, the LGMD2 disease is strongly correlated to the defect of a calpain which is expressed in healthy people.

The invention relates to the nucleic acid sequence such as represented in FIG. 2 coding for a $C^{++}$ dependent protease, or calpain, which is involved in LGMD2 disease, and more precisely LGMD2A. It also relates to a part of this sequence provided it is able to code for a protein having a calcium-dependent protease activity involved in LGMD2, or a sequence derived from one of the above sequences by substitution, deletion or addition of one or more nucleotides provided that said sequence is still coding for said protein, all the nucleic acids yielding a sequence complementary to a sequence as defined above.

The genomic organisation of the human nCL1 gene has been determined by the inventors, and consists of 24 exons and extends over 40 kb as represented in FIG. 8, and is also a part of the invention. About 35 kb of this gene have been sequenced. A systematic screening of this gene in LGMD2A families led to the identification of 14 different mutations, establishing that a number of independent mutational events in nCL1 are responsible for LGMD2A. Furthermore, this is the first demonstration of a muscular dystrophy resulting from an enzymatic rather than a structural defect.

In the present specification, CANP3 means the protein which is a $Ca^{++}$ dependent protease, or calpaïn, and coded by the nCL1 gene on chromosome 15.

The invention relates also to a protein, called CANP3, consisting in the amino acid sequence such as represented in FIG. 2 and which is involved, when mutated, in the LGMD2 disease.

Is The cDNA of the gene coding for CANP3, which is coding for the protein, is also represented in FIG. 2, and is a part of the invention.

The protein coded by this DNA is CANP3, a calcium-dependent protease belonging to the Calpaïn family.

Are also included in the present invention the nucleic acid sequences derived from the cDNA of FIG. 2 by one or more substitutions, deletions, insertions, or by mutations in 5' or 3' non coding regions or in splice sites, provided that the translated protein has the protease, calcium-dependent activity, and when mutated, induce LGMD2 disease.

The nucleic acid sequence encoding the protein might be DNA or RNA and be complementary to the nucleic and sequence represented in FIG. 2.

The invention also relates to a recombinant vector including a DNA sequence of the invention, under the control of a promoter allowing the expression of the calpaïn in an appropriate host cell.

A procaryotic or eucaryotic host cell transformed by or transfected with a DNA sequence comprising all or part of the sequence of FIG. 2 is a part of the invention.

Such a host cell might be either:
- a cell which is able to secrete the protein and this recombinant protein might be used as a drug to treat the LGMD2, or
- a packaging cell line transfected by a viral or retroviral vector: the cell lines bearing recombinant vector might be used as a drug for gene therapy of LGMD2.

All the systems used today for gene therapy including adenoviruses and retroviruses and others described for example in <<l'ADN médicament>>(John Libbey, Eurotext, 1993), and bearing one of the DNA sequence of the invention are included herein by reference.

The examples hereunder and attached figures indicate how the structure of the gene was established, and how relationship between the gene and the LGMD was established.

Legend of the figures:

BRIEF DESCRIPTIONS OF THE DRAWINGS

FIGS. 1A–1C

A) Genomic organisation of the nCL1 gene

The gene covers a 40 kb region of which 35 were sequenced (Accession number NT_030828 Homo sapiens chromosome 15). Introns and exons are drawn to scale, the latter being indicated by numbered vertical bars. The first intron is the largest one and remains to be fully sequenced. Position of intragenic microsatellites are indicated by asterisks. Arrows indicate the orientation of Alu (closed) and of Mer2 (greyed) repeat sequences.

B) EcoRI restriction map

An EcoRI (E) restriction map of this region was established with the help of cosmids from this region. The location of nCL1 gene is indicated as a black bar. The size of the corresponding fragments are indicated and are underlined when determined by sequence analysis.

C) Cosmid map of the nCL1 gene region.

Cosmids were from a cosmid library constructed by subcloning YAC 774G4 (Richard et al., 1995) and are presented as lines. Dots on lines indicate positive STSs (indicated in boxed rectangles). A minimum of three cosmids cover the entire gene.

FIGS. 2A–2C: Sequence of the human nCL1 cDNA (B), and the flanking 5' (A) and 3' (C) genomic regions.

A) (SEQ ID NO:68) and C) (SEQ ID NO:69) The polyadenylation signal and putative CAAT, TATAA sites are boxed. Putative Sp1 (position –477 to –472), MEF2 binding sites (–364 to –343) and CArG box (–685 to –672) are in bold. The Alu sequence present in the 5' region is underlined.

B) FIG. 2B shows the nucleotide sequence of the human nCL1 cDNA (SEQ ID NO:70). The corresponding amino acids are shown below the sequence. The coding sequence between the ATG initiation codon and the TGA stop codon is 2466 bp (SEQ ID NO:70), encoding for an 821 amino acid protein (SEQ ID NO:6). The adenine in the first methionine codon has been assigned position 1. Locations of introns within the nCL1 gene are indicated by arrowheads. Nucleotides which differ from the previously published ones are indicated by asterisks.

FIG. 3: Alignments of amino acid sequences of the muscle-specific calpains.

The human nCL1 protein is shown on the first line. The 3 muscle-specific In sequences (NS, IS1 and IS2) are underlined. The second line corresponds to the rat sequence (Accession no P)(SEQ ID NO: 7). The third and fourth lines show the deduced amino acid sequences encoded by pig and bovine Expressed Sequences Tagged (GenBank accession no U05678 and no U07858, respectively)(SEQ ID NO: 8 and SEQ ID NO: 9). The amino acids residues which are conserved among all known members of the calpains are in reverse letters. A period indicates that the same amino acid is present in the sequence. Letters refer to the variant amino acid found in the homologous sequence. Position of missense mutations are given as numbers above the mutated amino acid.

FIGS. 4A–4B: Distribution of the mutations along nCL1 protein structure.

A) Positions of the 23 introns are indicated by vertical bars in relation to the corresponding amino acid coordinates.

B) The nCL1 protein is depicted showing the four domains (I, II, III, IV) and the muscle specific sequences (NS, IS1 and IS2). The position of missense mutations within nCL1 domain are indicated by black dots. The effect of nonsense and frameshift mutations are illustrated as truncated lines, representing the extent of protein synthesised. Name of the corresponding families are indicated on the left of the line. The out of frame ORF is given by hatched lines.

FIG. 5: Northern blot hybridisation of a nCL1 clone

A mRNA blot (Clontech) containing 2 µg of poly(A)+ RNA from each of eight human tissues was hybridised with a nCL1 genomic clone spanning exons 20 and 21. The latter detects a 3.6 kb mRNA present only in a line corresponding to the skeletal muscle mRNA.

FIG. 6: Representative mutations identified by heteroduplex analysis.

Examples of mutation screening by heteroduplex analysis. Pedigree B505 shows the segregation of two different mutations in exon 22.

FIGS. 7A–7D: Homozygous mutations in the nCL1 gene

Detection by sequencing of mutations in exons 2 (a), 8 (b), 13 (c) and 22 (d). Sequences from a healthy control are shown above each mutant sequence. Asterisks indicate the position of the mutated nucleotides. The consequences on codon and amino acid residues are indicated on the left of the figure together with the name of the family.

further confirmed by STS (for Sequence Tagged Site) assays. Primers used for the localisation of the nCL1 gene are P94in2, P94in13 and pcr6a3, as shown in FIG. 1 and their characteristics being defined in Table 1.

TABLE 1

PCR primers used for localisation of the nCL1 gene.

| Primer name | Primer sequence (5'-3') | Position within the cDNA | Annealing temp (° C.) | PCR product size on cDNA | PCR product size on genomic DNA |
|---|---|---|---|---|---|
| P94in2 | ATGGAGCCAACA-GAACTGAC (SEQ ID NO:10) | 341–360 | 58 | 108 | 1758 |
|  | GTATGACTCGGAAAA-GAAGGT (SEQ ID NO:11) | 428–448 |  |  |  |
| P94in13 | TAAGCAAAAGCAGTC-CCCAC (SEQ ID NO:12) | 1893–1912 | 58 | 64 | 1043 |
|  | TTGCTGTTCCTCACTTTCCTG (SEQ ID NO:13) | 1936–1956 |  |  |  |
| P94-6a3 | GTTTCATCTGCTGCTTCGTT (SEQ ID NO:14) | 2342–2361 | 56 | 130 | 818 |
|  | CTGGTTCAGGCATACATGGT (SEQ ID NO:15) | 2452–2471 |  |  |  |
| P94exlter | TTCTTTATGTGGACCCT-GAGTT (SEQ ID NO:16) | 218–239 | 55 | 76 | 76 |
|  | ACGAACTGGATGGG-GAACT (SEQ ID NO:17) | 275–293 |  |  |  |

FIGS. 8A–8D: Structure of the nCL1 gene

FIG. 8A represents the 5' part of the gene with exon 1 (SEQ ID NO: 1).

FIG. 8B represents the part of the gene including exon 2 to 8 (SEQ ID NO: 2).

FIG. 8C represents the part of the gene including exon 9 (SEQ ID NO: 3).

FIG. 8D represents the part of the gene including exons 10 to 24 including the 3' non transcribed region (SEQ ID NO: 4).

EXAMPLES

Example 1
Localisation of the nCL1 within the LGMD2A Interval

Detailed genetic and physical maps of the LGMD2A region were constructed (Fougerousse et al., 1994), following the primary linkage assignment to 15q (Beckmann et al., 1991). The disease locus was bracketed between the D15S129 and D15S143 markers, defining the cytogenetic boundaries of the LGMD2A region as 15q15.1–15q21.1 (Fougerousse et al., 1994). Construction and analysis of a 10–12 Mb YAC contig (Fougerousse et al., 1994) permitted us to map 33 polymorphic markers within this interval and to further narrow the LGMD2A region to between D15S514 and D15S5222.

The nCL1 gene had been localised to chromosome 15 by hybridisation with sorted chromosomes and by Southern hybridisation to DNA from human-mouse cell hybrids (Ohno et al., 1989) cDNA capture using YACs from the LGMD2A interval allowed the identification of thirteen positional candidate genes. nCL1 was one of the two transcripts identified that showed muscle-specific expression as evidenced by northen blot analysis. The localisation was These primers are designed from different parts of the published human cDNA sequence (Sorimachi et al., 1989), and were used for an STS content screening on DNA from three chromosome 15 somatic cell hybrids and YACs from the LGMD2A contig. The results positioned the gene in a region previously defined as 15q15.1q21.1 and on 3 YACs (774G4, 926G10, 923G7) localised in this region. The relative positions of STSs along the LGMD2A contig allowed to localise the gene between D15S512 and D15S488, in a candidate region suggested by linkage disequilibrium studies.

Figure 1:
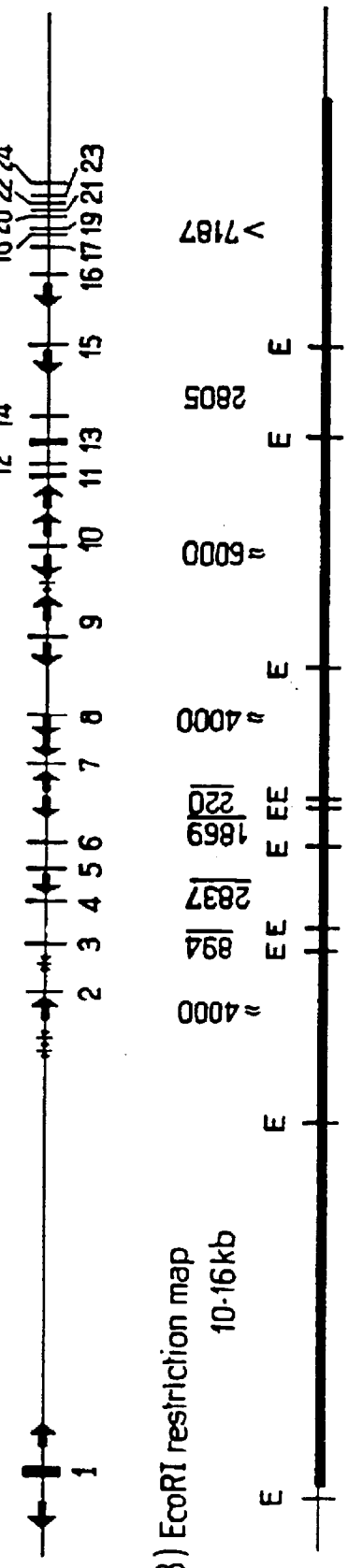
Figure 1:
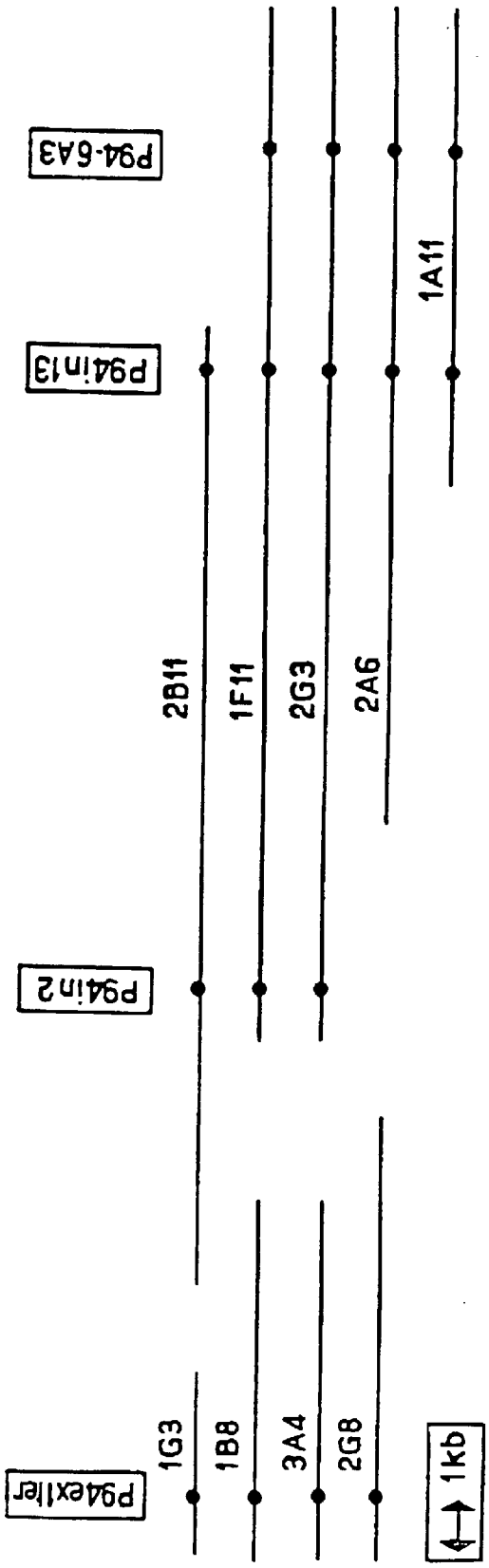

The same primers as above were used to screen a cosmid library from YAC 774G4. A group of 5 cosmids was identified (FIG. 1). Experiments with another nCL1 primer pair (P94ex1ter; Table 1) established that these cosmids cover all nCL1 exons except number 1, and that a second group of 4 cosmids contain this exon (FIG. 1). A minimal set of three overlapping cosmids (2G8-2B11-1F11) covers the entire gene (FIG. 1). DNA from these cosmids was used to construct an EcoRI restriction map of this region (FIG. 1B).

Example 2
Determination of the nCL1 Gene Sequence

Most of the sequences were obtained through shotgun sequencing of partial digests of cosmid 1F11 subcloned in M13 and bluescript vectors, and by walking with internal primers. The sequence assembly was made using the XBAP software of the Staden package (Staden) and was in agreement with the restriction map of the cosmids. Sequences of exon 1 and adjacent regions were obtained by sequencing cosmid DNA or PCR products from human genomic DNA. The first intron is still not fully sequenced, but there is evidence that it may be between 10 to 16 kb in length (based on hybridisation of restriction fragments; data not shown). The entire gene, including its 5' and 3' regions, is more than 40 kb long, and shown in FIG. 8.

a) the cDNA sequence

Figure 2A:
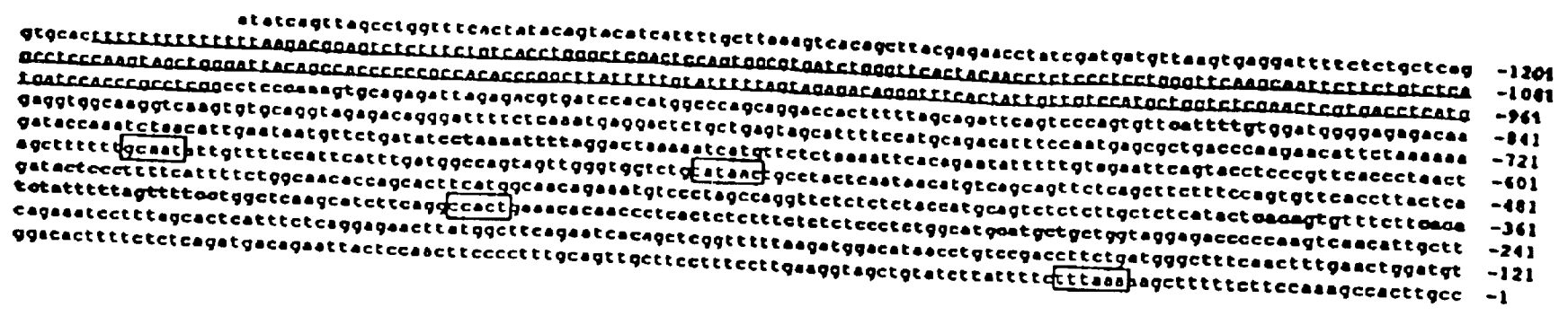
Figure 2B:
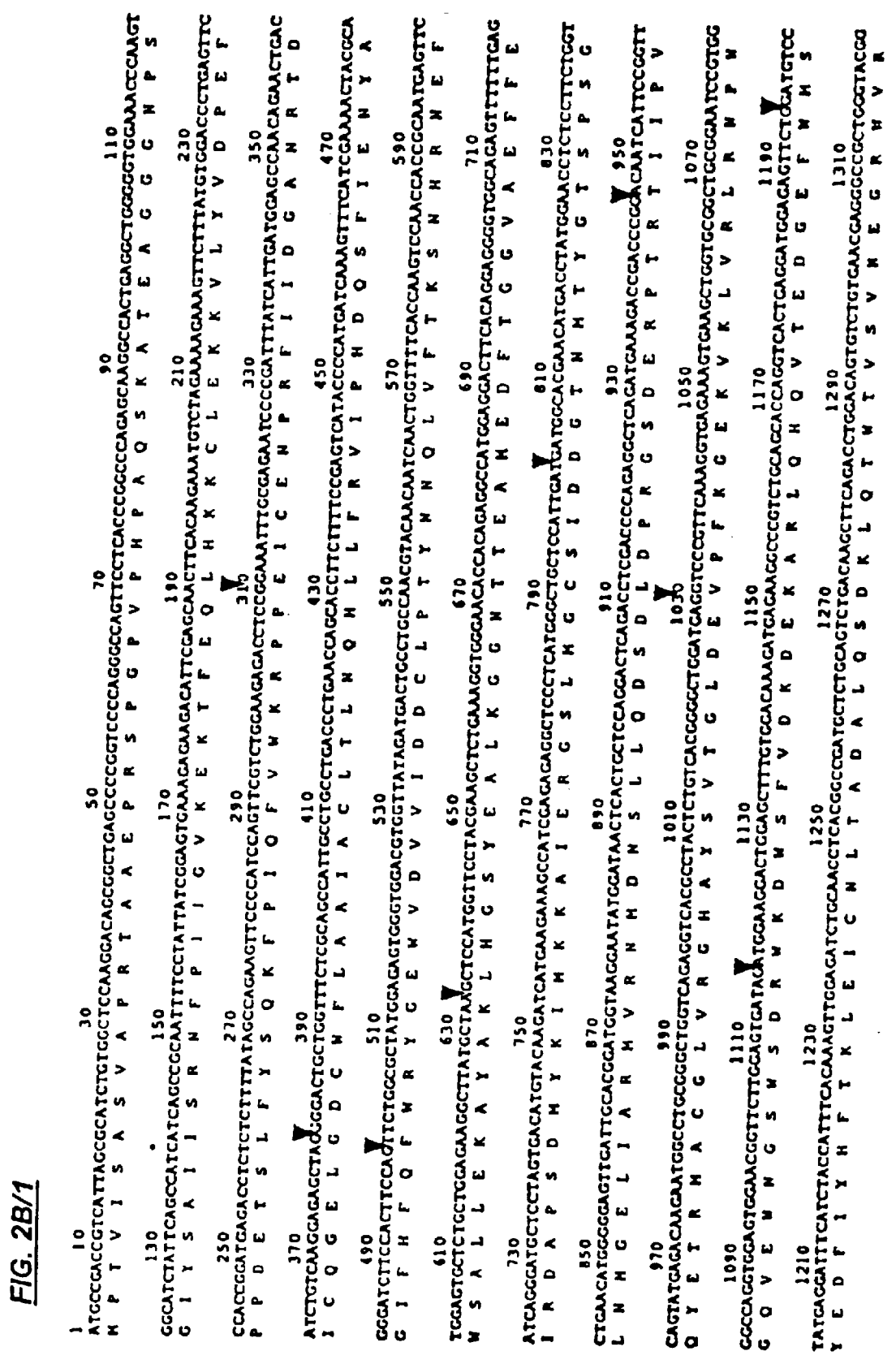
Figure 2C:
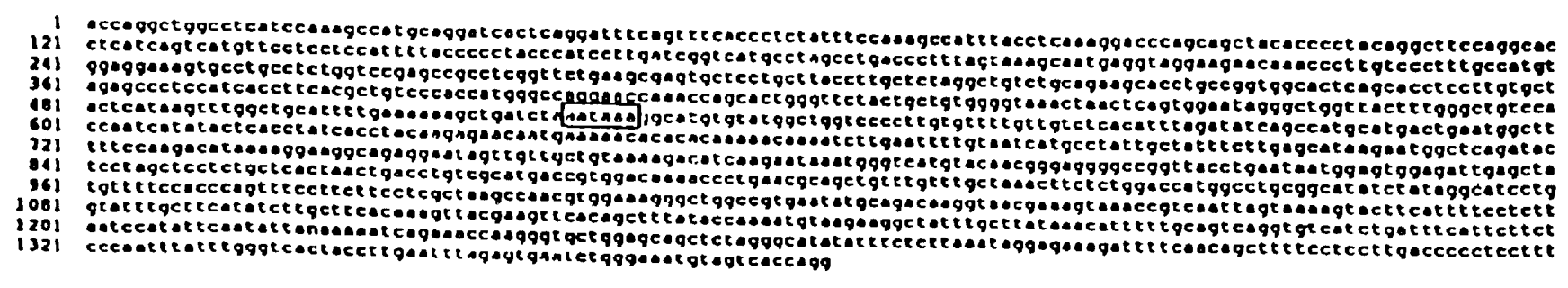

The used technology allows the implementation of the published human cDNA sequence of nCL1 (Sorimachi 1989). It contains the missing 129 bases corresponding to the N-terminal 43 amino acids (FIG. 2). It also differs from it at 12 positions, three of which occur at third base positions of codons and preserve the encoded amino acid sequence. The other 9 differences lead to changes in amino-acid composition (FIG. 2). As these different exons were sequenced repeatedly on at least 10 distinct genomes, we are confident that the sequence of FIG. 2 represents an authentic sequence and does not contain minor polymorphic variants. Furthermore, these modifications increase the local similarity with the rat nCL1 amino acid sequence (Sorimachi), although the overall similarity is still 94%.

The ATG numbered 1 in FIG. 2 is the translation initiation site based on homology with the rat nCL1, and is within a sequence with only 5 nucleotides out of 8 in common with the Kosak consensus sequence (Kosak M, 1984). Putative CCAAT and TATA boxes were observed 590, 324, (CCAAT) and 544 or 33 bp (TATA) upstream of the initiating ATG codon, respectively (Bucher, 1990). A GC-box binding the Sp1 protein (Dynan et al., 1983) was identified at position −477. Consensus sequences corresponding to potential muscle-specific regulatory elements were identified (FIG. 2). These include a myocyte-specific enhancer-binding factor 2 (MEF2) binding site (Cserjesi P. 1991), a CArG box (Minty A. 1986) and 6 E-boxes (binding sites for basic Helix-Loop-Helix proteins frequently found in members of MyoD family; Blackwell et Weintraub, 1990). The functional significance of these putative transcription factor binding sites in the regulation of nCL1 gene expression remains to be established.

Two potential AAUAAA polyadenylation signals, were identified 520 and 777 bp downstream of the TGA stop codon. The sequencing of a partial nCL1 cDNA containing a polyA tail, demonstrated that the first AAUAAA is the polyadenylation signal. The latter is embedded in a region well conserved with the rat nCL1 sequence and is followed after 4 bp by a G/T cluster, present in most genes 3' of the polyadenylation site (Birnstiel et al., 1985). The 3'-untranslated region of the nCL1 mRNA is 565 bp long. The predicted length of the cDNA should therefore be approximately 3550 or 3000 bp.

b) Comparison with calpain

Figure 3:
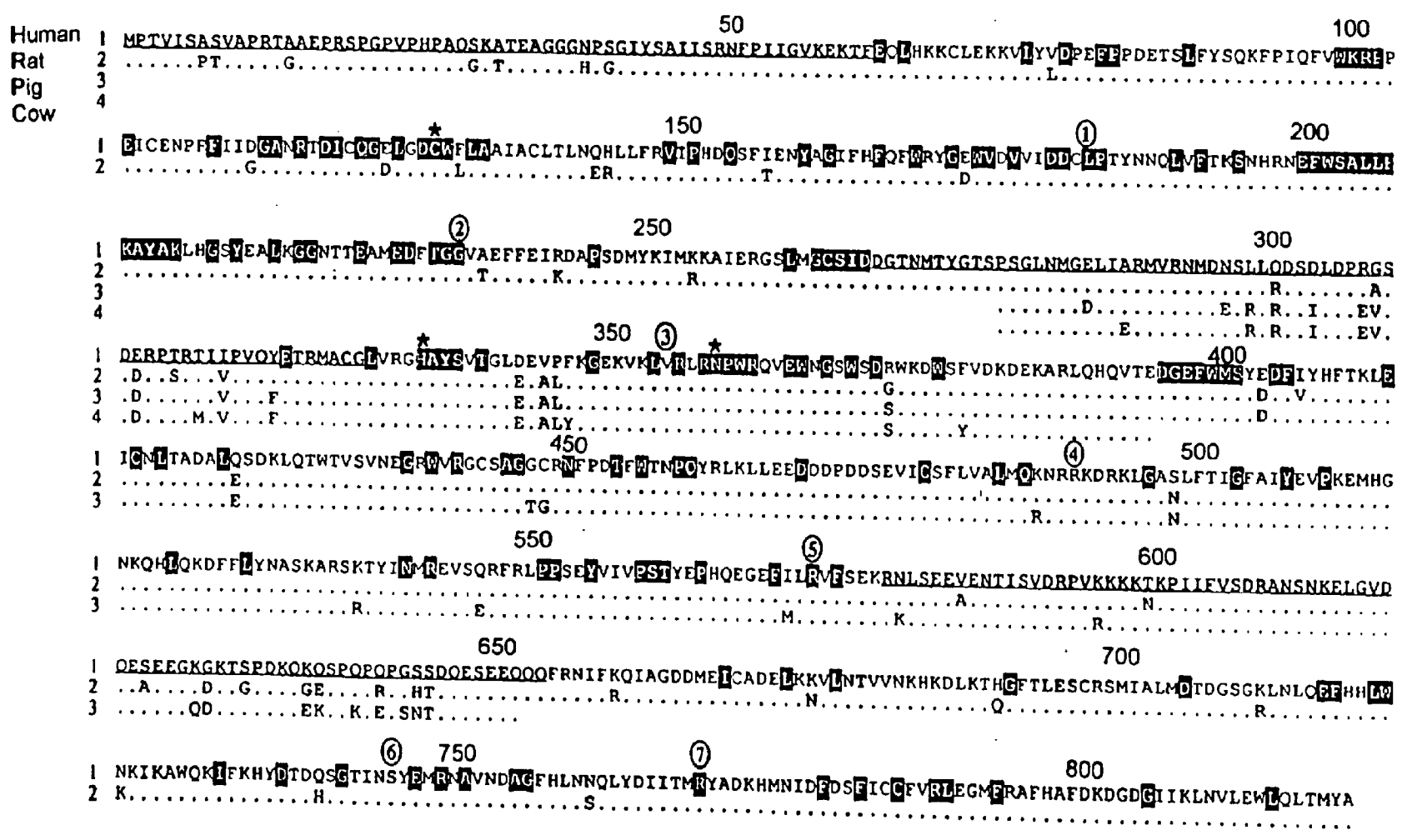

The sequence of the human nCL1 gene was compared to those of other calpains thereof (FIG. 3). The most telling comparisons are with the homologous rat (Accession no J05121), bovine (Accession no U07858) and porcine (Accession no U05678) sequences. The accession numbers refers to those or international genebanks, such as GeneBank (N.I.H.) or EMBL Database (EMBL, Heidelberg). High local similarities between the human and rat DNA sequences are even observed in the 5' (75%) or in different parts of the 3' untranslated regions (over 60%) (data not shown). The high extent of sequence homology manifested by the human and rat nCL1 gene in their untranslated regions is suggestive of evolutionary pressures on common putative regulatory sequences.

c) Genomic organisation of the nCL1 gene

A comparison of the published nCL1 human cDNA (Sorimachi et al., 1989) with the corresponding genomic sequence led to the identification of 24 exons ranging in length from 12 bp (exon 13) to 309 bp (exon 1), with a mean size of 100 bp (FIG. 1). The size of introns ranges from 86 bp to about 10–16 kb for intron 1.

The intron-exon boundaries as shown:in Table 2 exhibit close adherence to 5' and 3' splice site consensus sequences (Shapiro and Senapathy, 1987).

TABLE 2

Sequence at the intron-exon junctions. A score expressing adherence to the was calculated for each site according to Shapiro and Senapathy (1987). Sequences of exons and introns are in upper and lower cases, respectively. Size of exons are given in parenthesis.

| splice donor site | score (%) | Intron | score (%) | splice acceptor site | Exon | |
|---|---|---|---|---|---|---|
| | | | | | Exon 1 | (309 bp) -> |
| ... CTCCGgtgagt ... | 88.5 | <-Intron 1-> | 99.0 | ... tttttgtttcacagGAAAT ... | Exon 2 | (70 bp) -> |
| ... GCTAGgtagga ... | 83.5 | <-Intron 2-> | 90.0 | ... gtgtctgcctgcagGGGAC ... | Exon 3 | (119 bp) -> |
| ... TCCAGgtgagg ... | 92 | <-Intron 3-> | 81.5 | ... acgcttctgtgcagTTCTG ... | Exon 4 | (134 bp) -> |
| ... GCTAAgtaagc ... | 82 | <-Intron 4-> | 81.5 | ... atcctctctctaagGCTCC ... | Exon 5 | (169 bp) -> |
| ... TTGATgtaagt ... | 87 | <-Intron 5-> | 79.5 | ... ccatcgggcctcagGATGG ... | Exon 6 | (144 bp) -> |
| ... CCCGgtgtgt ... | 77.5 | <-Intron 6-> | 91 | ... ttactgctctacagACAAT ... | Exon 7 | (84 bp) -> |
| ... ATGAGgtaagc ... | 94 | <-Intron 7-> | 78.5 | ... tctgtgtgcttaagGTCCC ... | Exon 8 | (86 bp) -> |
| ... GATAGgtaggt ... | 89 | <-Intron 8-> | 91.5 | ... cattttcccaccagATGGA ... | Exon 9 | (78 bp) -> |
| ... TTCTGgtgagt ... | 88 | <-Intron 9-> | 92 | ... ttccaacctctcagGATGT ... | Exon 10 | (161 bp) -> |
| ... CCCAGgtggga ... | 80 | <-Intron 10-> | 68.5 | ... ttctggggtgcagATACT ... | Exon 11 | (170 bp) -> |
| ... ACGAGgtgtgt ... | 85.5 | <-Intron 11-> | 86 | ... tgtttcttctcaagGTTCC ... | Exon 12 | (12 bp) -> |
| ... AAGAGgtatag ... | 70 | <-Intron 12-> | 87 | ... tccccatctctcagATGCA ... | Exon 13 | (209 bp) -> |
| ... TCTGAgtgagt ... | 76.5 | <-Intron 13-> | 97 | ... tgtattcctcacagGGAAG ... | Exon 14 | (37 bp) -> |
| ... CAGTGgtgagt ... | 89 | <-Intron 14-> | 93.5 | ... cttttcttatgcagAAAAA ... | Exon 15 | (18 bp) -> |
| ... CCAAGgtaggt ... | 89 | <-Intron 15-> | 87 | ... cctcctctctccagCCCAT ... | Exon 16 | (114 bp) -> |
| ... CACAGgtgtct ... | 80 | <-Intron 16-> | 88 | ... ttgtgcctccacagCCACA ... | Exon 17 | (78 bp) -> |
| ... GAGATgtgagt ... | 84 | <-Intron 17-> | 92.5 | ... ccttcctcctcagGACAT ... | Exon 18 | (58 bp) -> |
| ... CAAAGgtgagt ... | 83 | <-Intron 18-> | 90 | ... ctccatccccccagACAAG ... | Exon 19 | (65 bp) -> |
| ... TGGATgtatcc ... | 56 | <-Intron 19-> | 88 | ... cctccctcctccagACAGA ... | Exon 20 | (69 bp) -> |
| ... GGCAGgtggga ... | 80 | <-Intron 20-> | 94 | ... tttttctattgccagAAATA ... | Exon 21 | (79 bp) -> |
| ... CGCAGgtgctg ... | 66 | <-Intron 21-> | 91 | ... ggtccctccacagGATTC ... | Exon 22 | (117 bp) -> |
| ... GTTCAgtaagt ... | 79 | <-Intron 22-> | 93.5 | ... gcattctttcacagGAGCT ... | Exon 23 | (59 bp) -> |
| ... TGGAGgtaaag ... | 81 | <-Intron 23-> | 79 | ... gggacttctttcagTGGCT ... | Exon 24 | (27 bp) -> |

When the genomic sequence was submitted to GRAIL analysis (Uberbacher et al., 1991), 11 exons were correctly recognised, 4 were not identified, 6 were inadequately defined and 2 were too small to be recognised (data not shown).

Figure 4:
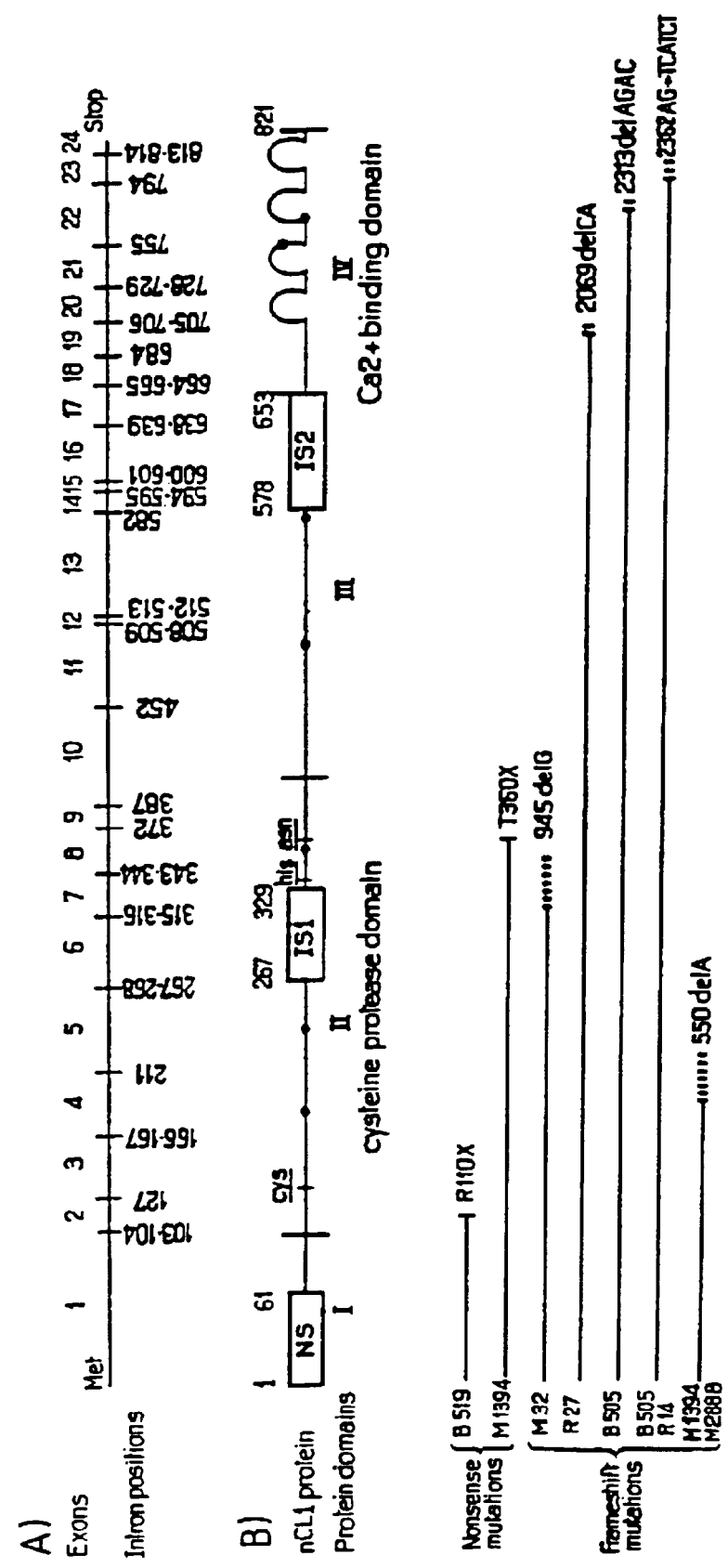

As already noted, the nCL1 gene has three unique sequence blocks, NS (amino acid residues 1 to 61), IS1 (residues 267 to 329) and IS2 (residues 578 to 653). It is interesting to note that each of these sequences, as well as the nuclear translocation signal inside IS2, are essentially flanked by introns (FIG. 4). The exon-intron organisation of the human nCL1 is similar to that reported for the chicken CANP (the only other large subunit calpain gene whose genomic structure is known; (Emori et al., 1986).

Four microsatellite sequences were identified. Two of them are in the distal part of the first intron: an $(AT)_{14}$ and an previously identified mixed-pattern microsatellite, S774G4B8, which was demonstrated to be non polymorphic (Fougerousse et al., 1994). A $(TA)_7(CA)_4(GA)_{13}$ was identified in the second intron and genotyping of 64 CEPH unrelated individuals revealed two alleles (with frequencies of 0.10 and 0.90). The fourth microsatellite is a mixed $(CA)_n(TA)_m$ repeat present in the 9th intron. The latter and the $(AT)_{14}$ repeat have not been investigated for polymorphism. Fourteen repetitive sequences of the Alu family and one Mer2 repeat were identified in the nCL1 gene (FIG. 1C), which has, thus, on the average one Alu element per 2.5 kb.

Southern blot experiments (Ohno et al., 1989) and STS screening (data not shown) suggest that there is but one copy per genome of this member of the calpain family.

Example 3

Expression of the nCL1 Gene

Figure 5:
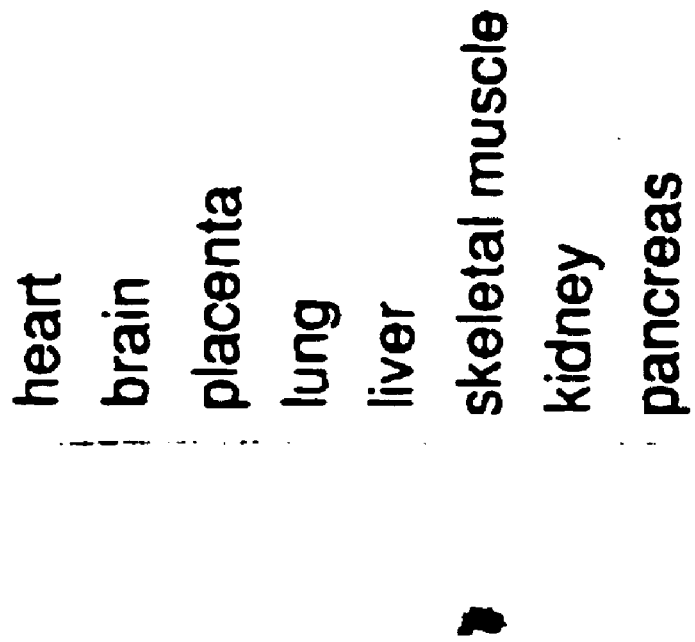

The pattern of tissue-specificity was investigated by northern blot hybridisation with a genomic subclone probe from cosmid 1F11 spanning exons 20 and 21. There is no evidence for the existence of an alternatively spliced form of nCL1, although this cannot be excluded. A transcript of about 3.4–3.6 kb was detected in skeletal muscle mRNA (FIG. 5). This size therefore favours that the position −544 is the functional TATA box.

Transcription studies suggested that it is an active gene rather than a pseudogene and its muscle-specific pattern of expression is consistent with the phenotype of this disorder (Sorimachi et al., 1989 and FIG. 5).

Example 4

Mutation Screening nCL1 fulfils both positional and functional criteria to be a candidate gene for LGMD2A. To evaluate its role in the etiology of this disorder, nCL1 was systematically screened in 38 LGMD2 families for the presence of nucleotide changes using a combination of heteroduplex (Keen et al., 1991) and direct sequence analyses.

PCR primers were designed to specifically amplify the exons and splice junctions and also the regions containing the putative CAT, TATA boxes and the polyadenylation signal of the gene as shown in Table 3.

TABLE 3

PCR primers used for the analysis of the nCL1 gene in LGMD patients.

| amplified region | Primer sequences (5'-3') | Size (bp) | Annealing temp. (° C.) |
|---|---|---|---|
| promotor | TTCAGTACCTCCCGTTCACC (SEQ ID NO: 18) | 296 | 59 |
| | GATGCTTGAGCCAGGAAAAC (SEQ ID NO: 19) | | |
| exon 1 | CTTTCCTTGAAGGTAGCTGTAT (SEQ ID NO: 20) | 438 | 60 |
| | GAGGTGCTGAGTGAGAGGAC (SEQ ID NO: 21) | | |
| exon 2 | ACTCCGTCTCAAAAAAATACCT (SEQ ID NO: 22) | 239 | 57 |
| | ATTGTCCCTTTACCTCCTGG (SEQ ID NO: 23) | | |
| exon 3 | TGGAAGTAGGAGAGTGGGCA (SEQ ID NO: 24) | 354 | 58 |
| | GGGTAGATGGGTGGGAAGTT (SEQ ID NO: 25) | | |
| exon 4 | GAGGAATGTGGAGGAAGGAC (SEQ ID NO: 26) | 292 | 59 |
| | TTCCTGTGAGTGAGGTCTCG (SEQ ID NO: 27) | | |
| exon 5 | GGAACTCTGTGACCCCAAAT (SEQ ID NO: 28) | 325 | 56 |
| | TCCTCAAACAAAACATTCGC (SEQ ID NO: 29) | | |
| exon 6 | GTTCCCTACATTCTCCATCG (SEQ ID NO: 30) | 315 | 57 |
| | GTTATTTCAACCCAGACCCTT (SEQ ID NO: 31) | | |
| exon 7 | AATGGGTTCTCTGGTTACTGC (SEQ ID NO: 32) | 333 | 56 |
| | AGCACGAAAAGCAAAGATAAA (SEQ ID NO: 33) | | |
| exon 8 | GTAAGAGATTTGCCCCCCAG (SEQ ID NO: 34) | 321 | 58 |
| | TCTGCGGATCATTGGTTTTG (SEQ ID NO: 35) | | |
| exon 9 | CCTTCCCTTCTTCCTGCTTC (SEQ ID NO: 36) | 173 | 56 |
| | CTCTCTTCCCCACCCTTACC (SEQ ID NO: 37) | | |
| exon 10 | CCTCCTCACCTGCTCCCATA (SEQ ID NO: 38) | 251 | 56 |
| | TTTTTCGGCTTAGACCCTCC (SEQ ID NO: 39) | | |
| exon 11 | TGTGGGAATAGAAATAAATGG (SEQ ID NO: 40) | 355 | 57 |
| | CCAGGAGCTCTGTGGGTCA (SEQ ID NO: 41) | | |
| exon 12 | GGCTCCTCATCCTCATTCACA (SEQ ID NO: 42) | 312 | 61 |
| | GTGGAGGAGGGTGAGTGTGC (SEQ ID NO: 43) | | |
| exon 13 | TGTGGCAGGACAGGACGTTC (SEQ ID NO: 44) | 337 | 60 |
| | TTCAACCTCTGGAGTGGGCC (SEQ ID NO: 45) | | |
| exon 14 | CACCAGAGCAAACCGTCCAC (SEQ ID NO: 46) | 230 | 61 |
| | ACAGCCCAGACTCCCATTCC (SEQ ID NO: 47) | | |
| exon 15 | TTCTCTTCTCCCTTCACCCT (SEQ ID NO: 48) | 225 | 57 |
| | ACACACTTCATGCTCTCTACCC (SEQ ID NO: 49) | | |
| exon 16 | CCGCCTATTCCTTTCCTCTT (SEQ ID NO: 50) | 331 | 56 |
| | GACAAACTCCTGGGAAGCCT (SEQ ID NO: 51) | | |

TABLE 3-continued

PCR primers used for the analysis of the nCL1 gene in LGMD patients.

| amplified region | Primer sequences (5'-3') | Size (bp) | Annealing temp. (° C.) |
|---|---|---|---|
| exon 17 | ACCTCTGACCCCTGTGAACC (SEQ ID NO: 52) TGTGGATTTGTGTGCTACGC (SEQ ID NO: 53) | 270 | 61 |
| exon 18 | CATAAATAGCACCGACAGGGA (SEQ ID NO: 54) GGGATGGAGAAGAGTGAGGA (SEQ ID NO: 55) | 258 | 59 |
| exon 19 | TCCTCACTCTTCTCCATCCC (SEQ ID NO: 56) ACCCTGTATGTTGCCTTGG (SEQ ID NO: 57) | 159 | 57 |
| exons 20–21 | GGGGATTTTGCTGTGTGCTG (SEQ ID NO: 58) ATTCCTGCTCCCACCGTCTC (SEQ ID NO: 59) | 333 | 61 |
| exon 22 | CACAGAGTGTCCGAGAGGCA (SEQ ID NO: 60) GGAGATTATCAGGTGAGATGCC (SEQ ID NO: 61) | 282 | 57 |
| exons 22–23 | CAGAGTGTCCGAGAGGCAGGG (SEQ ID NO: 62) CGTTGACCCCTCCACCTTGA (SEQ ID NO: 63) | 608 | 61 |
| exon 24 | GGGAAAACATGCACCTTCTT (SEQ ID NO: 64) TAGGGGGTAAAATGGAGGAG (SEQ ID NO: 65) | 375 | 58 |
| polyadenylation signal | ACTAACTCAGTGGAATAGGG (SEQ ID NO: 66) GGAGCTAGGATAGCTCAAT (SEQ ID NO: 67) | 173 | 56 |

PCR products made on DNA from blood of specific LGMD2A patients were then subjected either to heteroduplex analysis or to direct sequencing, depending on whether the mutation, based on haplotype analysis, was expected to be homozygous or heterozygous, respectively. It was occasionally necessary to clone the PCR products to precisely identify the mutations (i.e., for microdeletions or insertions and for some heterozygotes). Disease-associated mutations are summarised in Table 4 hereunder and their position along the protein is shown in FIG. 4 (SEQ ID NO: 5).

of these mutations was seen among 120 control chromosomes from the CEPH reference families.

Example 5
Analysis of Families Genes, Chromosome-15 Ascertained Families

The initial screening for causative mutations was performed on families, each containing a LGMD gene located on chromosome 15. These included families from the Island of La Réunion (Beckmann et al., 1991), from the Old Order

TABLE 4 nCL1 mutation in LGMD2A families.
Codons and amino acid positions are numbered on the basis of the cDNA sequence starting from ATG.

| Exon | Families | Nucleotide position | Nucleotide change | Amino acid position | Amino acid change | Restriction si |
|---|---|---|---|---|---|---|
| 2 | B519" | 328 | CGA->TGA | 110 | Arg->stop | |
| 4 | M42 | 545 | CTG->CAG | 182 | Leu->Gln | |
| 4 | M1394:M2888 | 550 | CAA->CA | 184 | frameshift | |
| 5 | M35:M37 | 701 | GGG->GAG | 234 | Gly->Glu | |
| 6 | M32 | 945 | CGG->CG | 315 | frameshift | -Smal |
| 7 | M2407* | 1061 | GTG->GGG | 354 | Val->Gly | |
| 8 | M1394 | 1079 | TGG->TAG | 360 | Trp->stop | -Bstnl, -Eco |
| 11 | M2888 | 1468 | CGG->TGG | 490 | Arg->Trp | |
| 13 | R12" | 1715 | CGG->CAG | 572 | Arg->Gln | -Mspl |
| 19 | R27 | 2069–2070 | deletion AC | 690 | frameshift | |
| 21 | R14; R17 | 2230 | AGC->GGC | 744 | Ser->Gly | -AluI |
| 22 | A*; B501*; M32 | 2306 | CGG->CAG | 769 | Arg->Gln | |
| 22 | B505 | 2313–2316 | deletion AGAC | 771–772 | frameshift | |
| 22 | R14; B505 | 2362–2363 | AG->TCATCT | 788 | frameshift | |

The first letter of the family code refers to the origin of the population B=Brazil, M=metropolitan France, R=Isle of La Réunion, A=Amish.

Each mutation was confirmed by heteroduplex analysis, by sequencing of both strands in several members of the family or by enzymatic digestion when the mutation resulted in the modification of a restriction site. Segregation analyses of the mutations, performed on DNAs from all available members of the families, confirmed that these sequence variations are on the parental chromosome carrying the LGMD2A mutation. To exclude the possibility that the missense substitutions might be polymorphisms, their presence was systematically tested in a control population: none Amish from northern Indiana (Young et al., 1992,) and 2 Brazilian families (Passos Bueno et al., 1993).

a) Reunion Island families

Genealogical studies and geographic isolation of the families from the Isle of La Réunion were suggestive of a single founder effect. Genetic analyses are, however, inconsistent with this hypothesis as the families present haplotype heterogeneity. At least, six different carrier chromosomes are encountered, (with affected individuals in several families being compound heterozygotes). Distinct mutations corresponding to four of these six haplotypes have been identified thus far.

Figure 6:
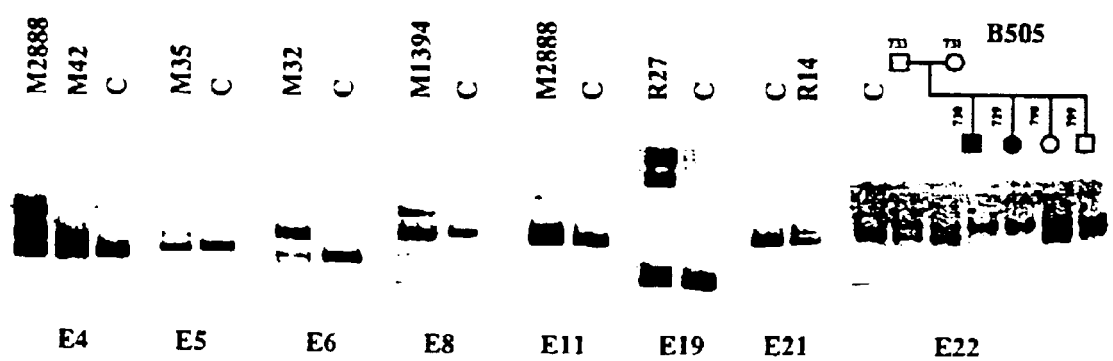

In family R14, exons 13, 21 and 22 showed evidence for sequence variation upon heteroduplex analysis (FIG. 6).

Sequencing of the associated PCR products revealed (i) a polymorphism in exon 13, (ii) a missense mutation (A→G) in exon 21 transforming the Ser$^{744}$ residue to a glycine in the loop of the second EF-hand in domain IV of the protein (FIG. 4), and (iii) a frameshift mutation in exon 22. The exon 21 mutation and the polymorphism in exon 13 form an haplotype which is also encountered in family R17. Subcloning of the PCR products was necessary to identify the exon 22 mutation. Sequencing of several clones revealed a replacement of AG by TCATCT (data not shown). This frameshift is mutation causes premature termination at nucleotide 2400 where an in frame stop codon occurs (FIG. 4).

The affected individuals in family R12 are homozygous for all markers of the LGMD2A interval (Allamand, submitted). Sequencing of the PCR products of exon 13 revealed a G to A transition at base 1715 of the cDNA resulting in a substitution of glutamine for Arg$^{572}$ (FIG. 7) within domain III, a residue which is highly conserved throughout all known calpains. This mutation, detectable by loss of MspI restriction site, is present only in this family and in no other examined LGMD2A families or unrelated controls.

In family R27, heteroduplex analysis followed by sequencing of the PCR products of an affected child revealed a two base pair deletion in exon 19 (FIG. 6 and table 4). One AC out of three is missing at this position of the sequence, producing a stop codon at position 2069 of the cDNA sequence (FIG. 4).

b) Amish families

Figure 7:
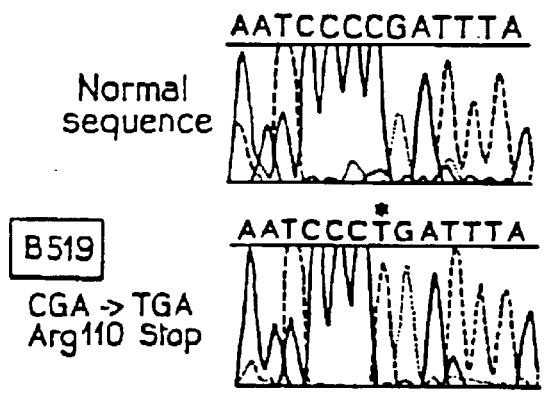
Figure 7:
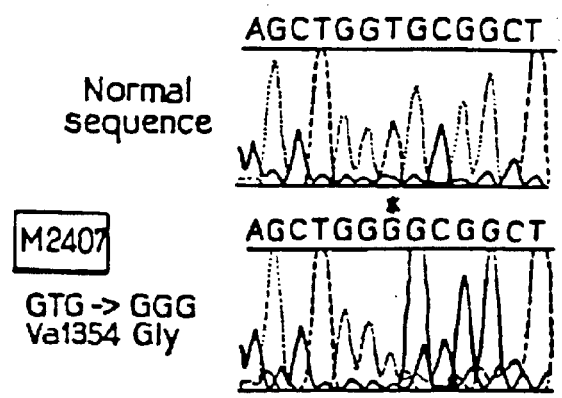
Figure 7:
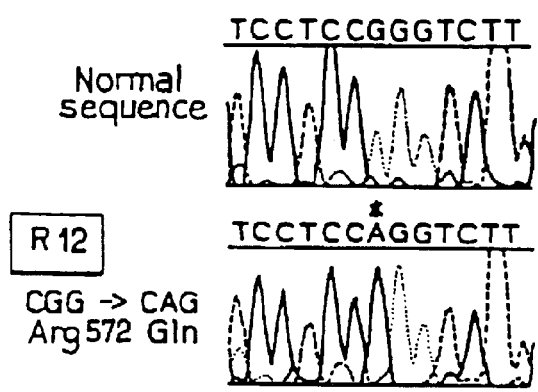
Figure 7:
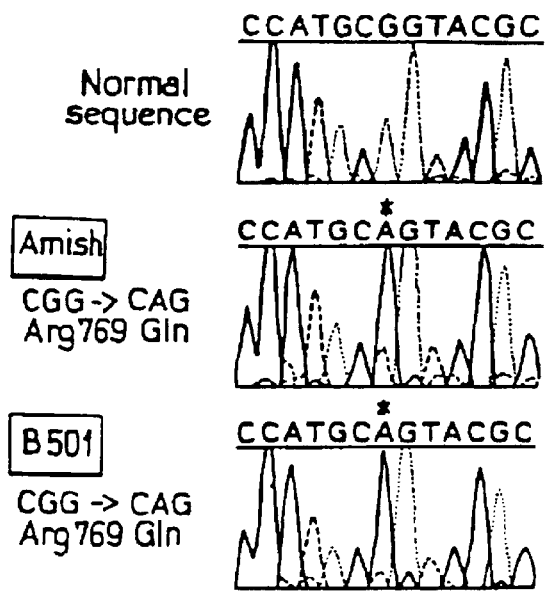

As expected, due to multiple consanguineous links, the examined LGMD2A Northern Indiana Amish patients were homozygous for the haplotype on the chromosome bearing the mutant allele (Allamand et al., 1995). A (G→A) missense mutation was identified at nucleotide 2306 within exon 22 (FIG. 7). The resulting codon change is CGG to GAG, transforming Arg$^{769}$ to glutamine. This residue, which is conserved throughout all members of the calpaïn family in all species, is located in domain IV of the protein within the 3rd EF-hand at the helix-loop junction. This mutation was encountered in a homozygous state in all patients from 12 chromosome 15-linked Amish families, in agreement with the haplotype analysis. We also screened six Southern Indiana Amish LGMD families, for which the chromosome 15 locus was excluded by linkage analyses (Allamand ESHG, submitted, ASHG 94). As expected, this nucleotide change was not present in any of the patients from these families, thus confirming the genetic heterogeneity of this disease in this genetically related isolate.

c) Brazilian families

As a result of consanguineous marriages, two Brazilian families (B501, B519) are homozygous for extended LGMD2A carrier haplotypes (data not shown). Sequencing PCR products from affected individuals of these families demonstrated that family B501 has the same exon 22 mutation found in northern Indiana Amish patients (FIG. 7), but embedded in a completely different haplotype. In family B519, the patients carry a C to T transition in exon 2, replacing Arg$^{328}$ with a TGA stop codon (FIG. 7), thus leading, presumably, to a very truncated protein (FIG. 4).

d) Analysis of other LGMD families

Having validated the role of the candidate gene in the chromosome 15 ascertained families, we next examined by heteroduplex analysis LGMD families for which linkage data were not informative. These included one Brazilian (B505) and 13 metropolitan French pedigrees.

Heteroduplex bands were revealed for exons 1, 3, 4, 5. 6, 8, 11, 22 of one or more patients (FIG. 6). Of all sequence variants, 10 were identified as possible pathogenic mutations; (5 missense, 1 nonsense and 4 frameshift mutations) and 3 as polymorphisms with no change of amino acid of the protein. All causative mutations identified are listed in Table 4 here-above. Identical mutations were uncovered in apparently unrelated families. The mutations shared by families M35 and M37, and M2888 and Ml 1394, respectively, are likely to be the consequence of independent events since they are embedded in different marker haplotypes. In contrast, it is likely that the point mutation in exon 22 of the Amish and in the M32 kindreds corresponds to the same mutational event as both chromosomes share a common four marker haplotype (774G4A1-774G4A10-774G454D-774G4A2) around nCL1 (data not shown), possibly reflecting a common ancestor. The same holds true for the AG to TCATCT substitution mutation encountered in exon 22 in families B505 and R14. The exon 8 (T→G) transversion is present in the two carrier chromosomes of M2407, the only metropolitan family homozygous by haplotype, possibly reflecting an undocumented consanguinity. For some families, no disease-causing mutation has been detected thus far (M40 for example).

In addition to the polymorphism present in exon 13 in families R14 and R17 (position 668) and in the intragenic microsatellites, four additional neutral variations were detected: a (T→C) transition at position 96, abolishing a DdeI restriction site in exon 1 in M31; a (C→T) transition in exon 3 (position 495) in M40 and in M37 forming a haplotype with the exon 5 mutation (in the former family, this polymorphism does not cosegregate with the disease); a (T→C) transition in the paternally derived promotor in M42 at position 428, which was also evidenced in healthy controls; and a variable poly(G) in intron 22 close to the splice site in families R20, R11, R19, M35 and M37. The latter is also present in the members of the CEPH families, but is not useful as a genetic marker as the visualisation and interpretation of mononucleotide repeat alleles is difficult.

In total, sixteen independent mutational events representing fourteen different mutations were identified. All mutations cosegregate with the disease in LGMD2A families. The characterised morbid calpaïn alleles contain nucleotide changes which were not found in alleles from normal individual. The discovery of two nonsense and five frameshift mutations in nCL1 supports the hypothesis that a deficiency of this product causes LGMD2A. All seven mutations result in a premature in-frame stop codon, leading to the production of truncated and presumably inactive proteins (FIG. 4). Evidences for the morbidity of the missense mutations come from (1) the relative high incidence of such mutations among LGMD2A patients; although it is difficult in the absence of functional assays to differentiate between a polymorphism and a morbid mutation, the occurrence of different "missense" mutations in this gene cannot all be accounted for as rare private polymorphisms: (2) the failure to observe these mutations in control chromosomes: and (3) the occurrence of mutations in evolutionarily conserved residues and/or in regions of documented functional importance. Four of seven missense mutations change an amino acid which is conserved in all known members of the calpain family in all species (FIG. 3). Two of the remaining mutations affect less conserved amino acid residues, but are located in important functional domains. The substitution V354G in exon 8 is 4 residues before the asparagine at the active site and S744G in exon 21 is within the loop of the second EF-hand and may impair the calcium-dependent regulation of calpain activity or the interaction with a small subunit (FIG. 4). Several missense mutations change a hydrophobic residue to a polar one, or vice versa (Table 4) possibly disrupting higher order structures.

METHODS

Description of the Patients

The LGMD2A families analysed were from 4 different geographic origins. They included 3 Brazilian families, 13 interrelated nuclear families from the Isle of la Réunion, 10 French metropolitan families and 12 US Amish families. The majority of these families were previously ascertained to belong to the chromosome 15 group by linkage analysis (Beckmann, 1991; Young, Passos-Bueno et al., 1993). However, some families from metropolitan France as well as one Brazilian family, B505, had non significant lodscores for chromosome 15. Genomic DNA was obtained from peripheral blood lymphocytes.

Sequencing of Cosmid c774G4-1F11 and EcoRI Restriction Map of Cosmids.

Cosmid 1 F11 (FIG. 1C) was subcloned following DNA preparation through Qiagen procedure (Qiagen Inc., USA) and partial digestion with either Sau3A, RsaI or AluI. Size-selected restriction fragments were recovered fom low-melting agarose and eventually ligated with M13 or Bluescript (Stratagene, USA) vectors. After electroporation in E.coli, recombinant colonies were picked in 100 µl of LB/ampicillin media. PCR reactions were performed on 1 µl of the culture in 10 mM Tris-HCl, pH 9.0, 50 mM KCl, 1.5 mM MgCl2, 0.1% Triton X-100, 0.01 gelatine, 200 µM of each dNTP, 1 U of Taq Polymerase (Amersham) with 100 ng of each vectors primers. Amplification was initiated by 5 min denaturation at 95° C., followed by 30 cycles of 40 sec denaturation at 92° C. and 30 sec annealing at 50° C. PCR products were purified through Microcon devices (Amicon, USA) and sequenced using the dideoxy chain termination method on an ABI sequencer (Applied Biosystems, Foster City, USA). The sequences were analysed and alignments performed using the XBAP software of the Staden package, version 93.9 (Staden, 1982). Gaps between sequence contigs were filled by walking with internal primers. EcoRI restriction map of cosmids was performed essentially as described in Sambrook et al. (1989).

Northern Blot Analysis

The probes were labelled by random priming with dCTP-($a^{32}P$). Hybridisation was performed to human multiple tissue northern blots as recommended by the manufacturer (Clontech, USA).

Analysis of PCR Products from LGMD2A Families

One hundred ng of human DNA were used per PCR under the buffer and cycle conditions described in Fougerousse (1994) (annealing temperature shown in Table 3). Heteroduplex analysis (Keene et al., 1991) was performed by electrophoresis of ten µl of PCR products on a 1.5 mm-thick Hydrolink MDE gels (Bioprobe) at 500–600 volt for 12–15 h depending of the fragment length. Migration profile was visualised under UV after ethidium bromide staining.

For sequence analysis, the PCR products were subjected to dye-dideoxy sequencing, after purification through microcon devices (Amicon, USA). When necessary, depending on the nature of the mutations (e.g., frameshift mutation or for some heterozygotes), the PCR products were cloned using the TA cloning kit from Invitrogen (UK). One µl of product was ligated to 25 ng of vector at 12° C. overnight. After electroporation into XL1-blue bacteria, several independent clones were analysed by PCR and sequenced as described above.

The invention results from the finding that the nCL1 gene when it is mutated is involved in the etiology of LGMD2A. It is exactly the contrary to what is stated in the litterature, e.g. that the disease is accompanied by the presence of a deregulated calpaïn. Identification of nCL1 as the defective gene in LGMD2A represents the first example of muscular dystrophy caused by mutation affecting a gene which is not a structural component of muscle tissue, in contrast with previously identified muscular dystrophies such as Duchenne and Becker (Bonilla et al., 1988), severe childhood autosomal recessive (Matsumara et al., 1992), Fukuyama (Matsumara et al., 1993) and merosin-deficient congenital muscular dystrophies (Tome et al., 1994).

The understanding of the LGMD2A phenotype needs to take into account the fact that there is no active nCL1 protein in several patients, a loss compatible with the recessive manifestation of this disease. Simple models in which this protease would be involved in the degradation or destabilisation of structural components of the cytoskeleton, extracellular matrix or dystrophin complex can therefore be ruled out. Furthermore, there are no signs of such alterations by immunocytogenetic studies on LGMD2 muscle biopsies (Matsumara et al., 1993; Tomé et al., 1994). Likewise, since LGMD2A myofibers are apparently not different from other dystrophic, ones, it seems unlikely that this calpain plays a role in myoblast fusion, as proposed for ubiquitous calpains (Wang et al., 1989).

All the data disclosed in these examples confirm that the nCL1 gene is a major gene involved in the disease when mutated.

The fact that morbidity results from the loss of an enzymatic activity raises hopes for novel pharmaco-therapeutic prospects. The availability of transgenic models will be an invaluable tool for these investigations.

The invention is also relative to the use of a nucleic acid or a sequence of nucleic acid of the invention, or to the use of a protein coded by the nucleic acid for the manufacturing of a drug in the prevention or treatment of LGMD2.

The finding that a defective calpain underlies the pathogenesis of LGMD2A may prove useful for the identification of the other loci involved in the LGMDs. Other forms of LGMD may indeed be caused by mutations in genes whose products are the CANP substrates or in genes involved in the regulation of nCL1 expression. Techniques such as the two-hybrid selection system (Fields et al., 1989) could lend themselves to the isolation of the natural protein substrate(s) of this calpain, and thus potentially help to identify other LGMD loci.

The invention also relates to the use of all or a part of the peptidic sequence of the enzyme, or of the enzyme, product of nCL1 gene, for the screening of the ligands of this enzyme, which might be also involved in the etiology and the morbidity of LGMD2.

The ligands which might be involved are for example substrate(s), activators or inhibitors of the enzyme.

The nucleic acids of the invention might also be used in a screening method for the determination of the components which may act on the regulation of the gene expression.

A process of screening using either the enzyme or a host recombinant cell, containing the nCL1 gene and expressing the enzyme, is also a part of the invention.

The pharmacological methods, and the use of nucleic acid and peptidic sequences of the invention are very potent applications.

The methods used for such screenings of ligands or regulatory elements are those described for example for the screening of ligands using cloned receptors.

The identification of mutations in the nCL1 gene provides the means for direct prenatal or presymptomatic diagnosis and carrier detection in families in which both mutations have been identified. Gene-based accurate classification of LGMD2A families should prove useful for the differential diagnosis of this disorder.

The invention relates to a method of detection of a predisposition to LGMD2 in a family or a human being, such method comprising the steps of:
  selecting one or more exons or flanking sequences which are sensitive in said family;
  selecting the primers specific for the or these exons or their flanking sequences, a specific example being the PCR primers of Table 3, or an hybrid thereof,
  amplifying the nucleic acid sequence, the substrate for this amplification being the DNA of the human being to be checked for the predisposition, and
  comparing the amplified sequence to the corresponding sequence derived from FIG. 2 or FIG. 8.

Table 2 indicates the sequences of the introns-exons junctions, and primers comprising in their structure these junctions are also included in the invention.

All other primers suitable for such RNA or DNA amplification may be used in the method of the invention.

In the same way, any suitable amplification method : PCR (for Polymerase Chain Reaction®) NASBA® (for Nucleic acid Sequence Based Amplification), or others might be used.

The methods usually used in the detection of one site mutations, like ASO (Allele specific PCR), LCR, or ARMS (Amplification Refactory Mutation System) may be implemented with the specific primers of the invention.

The primers, such as described in Tables 1 and 3, or including junctions of Table 2, or more generally including the flanking sequences of one of the 24 exons are also a part of the invention.

The kit for the detection of a predisposition to LGMD2 by nucleic acid amplification is also within the scope of the invention, such a kit comprises at least PCR primers selected from the group of:
  a) those described in Table 1
  b) those described in Table 3
  c) those including the introns-exons junctions of Table 2.
  d) derived from primers defined in a),b) or c).

The nucleic acid sequence of the invention might be inserted in a viral or a retroviral vector, said vector being able to transfect a packaging cell line.

The packaging transfected cell line, might be used as a drug for gene therapy of LGMD2.

The treatment of LGMD2 disease by gene therapy is implemented by a pharmaceutical composition containing a component selected from the group of:
  a) a nucleic acid sequence according to the invention,
  b) a cell line according to the invention,
  c) an amino acid sequence according to the invention.

REFERENCES

Allamand, V., Broux, O., Richard, I., Fougerousse, F., Chiannilkuchai, Bourg, N., Brenguier, L., Devaud, C., Pasturaud, P., Pereira de Souza, A., Roudaut, C., Tiscfield, J. A, Connealy, P. M., Fardeau, M., Cohen, D., Jackson, C. E. and Beckmann, J. S. (1995). Preferential localization of the limb girdle muscular distrophy type 2A gene in the proximal part of a 1-cM 15q15.1-q15.3 interval. Am. J. Hum. Genet. 56, 1417–1430.

Arikawa, E., Hoffman, E. P., Kaido, M., Nonaka, I., Sugita. H. and Arahata. K. (1991). The frequency of patients with dystrophin abnormalities in a limb-girdle patient population. Neurology 41, 1491–1496.

Bashir, R., Strachan, T., Keers, S., Stephenson, A., Mahjneh, I., Marconi, G., Nashef, L. and Bushby, K. M. D. (1994). A gene for autosomal recessive limb-girdle muscular dystrophy maps to chromosome 2p. Hum. Mol. Genet. 3, 455–457.

Beckmann. J. S., Richard, I., Hillaire, D., Broux, O., Antignac, C., Bois, E., Cann, H., Cottingham, R. W., Jr., Feingold, N., Feingold, J., Kalil, J., Lathrop, G. M., Marcadet, A., Masset, M., Mignard, C., Passos-Bueno, M. R., Pellerain, N., Zatz, M., Dausset, J., Fardeau, M. and Cohen, D. (1991). A gene for limb-girdle muscular dystrophy maps to chromosome 15 by linkage. C. R. Acad. Sci. Paris. III 312, 141–148.

Birnstiel, M. L., Busslinger, M. and Sturb, K. (1985). Transcription termination and 3' processing: The end is in site! Cell 41, 349–359.

Blackwell, T. K. and Weintraub, H. (1990). Differences and similarities in DNA-binding preferences of MyoD and E2A protein complexes revealed by binding site selection. Science 250, 1104–1110.

Bonilla, E., Samitt, C. E., Miranda, A. F., Hays, A P., Salviati, G., DiMauro, S., Kunkel, L. M., Hoffman, E. P. and Rowland, L. P. (1988). Duchenne muscular dystrophy: deficiency of dystrophin at the muscle cell surface. Cell 54, 447–452.

Bucher, P. (1990). Weight matrix descriptions of four eukaryotic RNA polymerase II promoter elements derived from 502 unrelated promoter sequences. J. Mol. Biol 212, 563–578.

Bushby, K. M. D. (1994). Limb-girdle muscular dystrophy. In Diagnostic criteria for neuromuscular disorders. A. E. H. Emery, ed. (Baarn, The Netherlands: ENMC), pp 2531.

Croall, b. E. and Demartino, G. N. (1991). Calcium-activated neutral protease (calpain) system: stucture, function, and regulation. Physiol. Rev. 71, 813–847.

Dynan, W. S. and Tjian, R. (1983). The promoter-specific transcription factor Sp1 binds to upstream sequences in the SV40 early promoter. Cell 35, 79–87.

Emery, A. E. H. (1991). Population frequencies of inherited neuromuscular diseases—a world survey. Neuromuscular Disorders 1, 19–29.

Emori, Y., Ohno, S., Tobita, M. and Suzuki, K (1986). Gene structure of calcium-dependent protease retains the ancestral organization of the calcium-binding protein gene. FEBS lett. 194, 249–252.

Fields, S. and Song. O. (1989). A novel genetic system to detect protein-protein interactions. Nature 340, 245–246.

Fougerousse, F., Broux, O., Richard, I., Allamand V., Pereira de Souza, A., Bourg N., Brenguier L., Devaud C., Pasturaud P., Roudaut C., Chiannilkulchai N., Hillaire D., Bui H., Chumakov I., Weissenbach J., Cherif D., Cohen D. and J. S. Beckmann (1994). Mapping of a chromosome 15 region involved in Limb-Girdle Muscular Dystrophy. Hum.: Mol. Genet. 3, 285–293.

Goll, D. E., Thompson, V. F., Taylor, R. G. and Zalewska, T. (1992). Is Calpain activity regulated by membranes and autolysis or by calcium and calpastatin? BioEssays 14, 549–556.

Gosset, L. A., Kelvin, D. J., Sternberg, E. A and Olson, E. (1989). A new myocyte-specific enhancer-binding factor that recognizes a conserved element associated with multiple muscle-specific genes. Mol. Cell. Biol. 9, 5022–5033.

Hirai, S., Kawasaki, H., Yaniv. M. and Suzuki, K. (1991). Degradation of transcription factors, c-Jun and c-Fos, by calpain. FEBS lett. 1, 57–61.

Imajoh, S., Kawasaki, H. and Suzuki, K. (1986). Limited autolysis of calcium-activated neutral protease (CANP): reduction of the Ca2+ requirement is due to the NH2-terminal processing of the large subunit. J. Biochem. 100, 633–642.

Jackson, C. E. and Carey, J. H. (1961). Progressive muscular dystrophy: autosomal recessive type. Pediatrics 77–84.

Keen, J., Lester D., Inglehearn, C., Curtis, A and Bhattacharya, S. (1991). Rapid detection of single base mismatches as heteroduplexes on Hydrolink gels. Trends Genet. 7, 5.

Kosak, M. (1984). Compilation and analysis of sequences upstream from the translational start site in eukaryotic mRNAs. Nucleic Acids Res. 12, 857–872.

Lovett. M., Kere, J. and Hinton, L. M. (1991). Direct selection: a method for the isolation of cDNAs encoded by large genomic regions. Proc. Natl. Acad. Sci. USA 88, 9628–9632.

Matsumara, K, Tome F. M. S., Collin H., Azibi K., Chaouch M., Kaplan J-K., Fardeau M. and Campbell K., P. (1992). Deficiency of the 50K dystrophin-associated glycoprotein in severe childhood autosomal recessive muscular dystrophy. Nature 359, 320–322.

Matsumura, K, Nonaka, I. and Campbell, K. P. (1993). Abnormal expression of dystrophin-associated proteins in Fukuyama-type congenital muscular dystrophy. Lancet 341, 521–522.

Minty, A. and Kedes. L. (1986). Upstream regions of the human cardiac actin gene that modulate its transcription in muscle cells: presence of an evolutionarily conserved repeated motif. Mol. Cell. Biol. 6, 2125–2136.

Miyamoto, S., Maki, M., Schmitt. M. J., Hatanaka, M. and Verma, I. M. (1994). TNF-a-induced phosphorylation of IKB is a signal for its degradation but not dissociation from NF-KB. Proc. Natl. Acad. Sci. USA in press.

Morton, N. E. and Chung, C. S. (1959). Formal genetics of muscular dystrophy. Am. J. Hum. Genet. 11, 360–379.

Murachi, T. (1989). Intracellular regulatory system involving calpain and calpastatin. Biochemistry Int. 18, 263–294.

Ohno, S., Emori, Y., Imajoh, S., Kawasaki, H., Kisaragi, M. and Suzuki. K. (1984). Evolutionary origin of a calcium-dependent protease by fusion of genes for a thiol protease and a calcium-binding protein? Nature 312, 566–570.

Ohno, S., Minoshima, S., Kudoh, J., Fukuyama, R., Shimizu, Y., Ohmi-Imajoh, S., Shimizu, N., Suzuki, K. (1989). Four genes for the calpain family locate on four different chromosomes. Cytogen. Cell Genet. 51, 1054.

Passos-Bueno, M.-R., Richard, I., Vainzof, M., Fougerousse, F., Weissenbach, J., Broux, O., Cohen. D., Akiyama, J., Marie, S. K. N., Carvalho, A. A., Guilherme, L., Kalil, J., Tsanaclis, A. M., Zatz, M. and Beckmann, J. S. (1993). Evidence of genetic heterogeneity in the autosomal recessive adult forms of limb-girdle muscular dystrophy following linkage analysis with 15 q probes in Brazilian families. J. Med. Genet. 30, 385–387.

Richard, I., Broux, O., Chiannilkulchai, N., Fougerousse, F., Allamand, V., Bourg, N., Brenguier, L., Devaud, C., Pasturaud, P., Roudaut, C., Lorenzo, F., Sebastiani-Kabatchis, C., Schultz, R. A., Polymeropoulos, M. H., Gyapay, G., Auffray, C. and Beckmann. J. (1994). Regional localization of human chromosome 15 loci. Genomics 23. 619–627.

Richard, I., Roudaut, C., Fougerousse, F., Chiannilkuchai, N. and Beckmann, J. S. (1995). An STS map of the limb girdle muscular dystrophy type 2A region. Mammalian Genome 6, 754–756.

Shapiro, M. and Senapathy, P. (1987). RNA splice junctions of different classes of eukaryotes: sequence statistics and functional implications in gene expression. Nucleic Acids Res. 15, 7155–7174.

Sorimachi, H., Imajoh-Ohmi, S., Emori, Y., Kawasaki, H., Ohno, S., Minami, Y. and Suzuki K. (1989). Molecular cloning of a novel mammalian calcium-dependant protease distinct from both m- and mu-type. Specific expression of the mRNA in skeletal muscle. J. Biol. Chem. 264, 20106–20111.

Sorimachi, H., Ishiura, S. and Suzuki, K. (1993a). A novel tissue-specific calpain species expressed predominantly in the stomach comprises two alternative splicing products with and without $Ca^{2+}$-binding domain. J. Biol. Chem. 268, 19476–19482.

Sorimachi, H., Toyama-Sorimachi, N., Saido, T. C., Kawasaki, H., Sugita, H., Miyasaka, M., Arahata, K., Ishiura, S. and Suzuki, K. (1993b). Muscle-specific calpain, p94, is degraded by autolysis immediately after translation, resulting in disappearance from muscle. J. Biol. Chem. 268, 10593–10605.

Staden, R. (1982). An interactive graphic program for comparing and aligning nucleic acid and amino acid sequences. Nucleic Acids Res. 10, 2951–2961.

Suzuki, K. and Ohno, S. (1990). Calcium activated neutral protease. Structure-function relationship and functional implications. Cell Struct. Funct. 15, 1–6.

Tagle, D. A., Swaroop. M. Lovett. M. and Collins, F. S. (1993). Magnetic bead capture of expressed sequences encoded within large genomic segments. Nature 361, 751–753.

Tomé, F. M. S., Evangelista T., Leclerc A., Sunada Y., Manole E., Estournet B., Barois A., Campbell K. P. and Fardeau M. (1994). Congenital muscular dystrophy with merosin deficiency. C. R. Acad. Sci. Paris 317, 351–357.

Uberbacher, E. C. and Mural, R. J. (1991). Locating protein-coding regions in human DNA sequences by a multiple sensor-neural network approach. Proc. Natl. Acad. Sci. USA 88, 11261–11265.

Walton, J. N. and Nattrass, F. J. (1954). On the classification, natural history and traitment of the myopathies. Brain 77, 169–231.

Wang, K. W., Villalobo, A. and Roufogalis, B. D. (1989). Calmodulin-binding proteins as calpain substrates. Biochem. J. 262, 693–706

Young, K., Foroud, T., Williams, P., Jackson, C. E., Beckmann, J. S., Cohen, D., Conneally, P. M., Tischfield. J. and Hodes, M. E. (1992). Confirmation of linkage of limb-girdle muscular dystrophy, type-2, to chromosome 15, Genomics 13, 1370–1371.

What is claimed is:

1. An isolated nucleic acid sequence comprising at least one sequence from the group consisting of SEQ ID NO:1 to SEQ ID NO:5, SEQ ID NO:68 and SEQ ID NO:69.

2. An isolated nucleic acid sequence that is complementary to a nucleic acid sequence according to claim 1.

3. A recombinant vector comprising in its structure a nucleotide sequence according to claim 1, under the control of regulatory elements, and involved in the expression of calpain activity in a LGMD2 disease.

4. An isolated nucleic acid sequence encoding the amino acid sequence of SEQ ID NO:6.

5. An isolated host cell which expresses a calpain enzyme activity, wherein said host cell is transformed or transfected with a nucleic acid sequence comprising the isolated nucleic acid sequence according to claim 1.

6. A method for detecting an LGMD2 disease, the method comprising the steps of:
   selecting nucleotide sequences from one or more exons from an nCL1 gene;
   selecting primers specific for said one or more exons;
   amplifying nucleic acid sequences of said one or more exons with said selected primers;
   comparing the amplified sequence to a corresponding sequence selected from the group consisting of SEQ ID NO:1 to SEQ ID NO:5, SEQ ID NO:68 and SEQ ID NO:69; and
   detecting a mutation in said amplified sequences which is indicative of an LGMD2 disease.

7. The method according to claim 6, wherein the primers are those selected from the group consisting of:
   SEQ ID NO:62 and SEQ ID NO:63.

8. The method according to claim 6, wherein LGMD2 is LGMD2A.

9. A kit for the detection of a predisposition to LGMD2 by nucleic acid amplification wherein said kit comprises primers selected from the group consisting of:
   SEQ ID NO:62 and SEQ ID NO:63.

10. A composition which contains an isolated nucleic acid sequence comprising at least one sequence selected from the group consisting of SEQ ID NO:1 to SEQ ID NO:5, SEQ ID NO:68 and SEQ ID NO:69.

11. A composition which contains an isolated host cell which expresses a calpain activity, wherein said host cell is transformed or transfected with a nucleic acid sequence comprising a nucleic acid sequence comprising at least one sequence selected from the group consisting of SEQ ID NO:1 to SEQ ID NO:5, SEQ ID NO:68 and SEQ ID NO:69.

* * * * *

SEQUENCE LISTING

<160> NUMBER OF SEQ ID NOS: 116

<210> SEQ ID NO 1
<211> LENGTH: 3018
<212> TYPE: DNA
<213> ORGANISM: Homo sapiens
<220> FEATURE:
<221> NAME/KEY: misc_feature
<222> LOCATION: (1)..(3018)
<223> OTHER INFORMATION: /label=figure 8a
<220> FEATURE:
<221> NAME/KEY: misc_feature
<222> LOCATION: (1)..(3018)
<223> OTHER INFORMATION: /label= Figure 8a

<400> SEQUENCE: 1

| | | | | | |
|---|---|---|---|---|---|
| tgataggtgc | ttgtaaactg | tgcttaacga | aaacataccg | tgtgctgtag | ggacttaact | 60 |
| cttgtttata | tcagttagcc | tggtttcgct | aacagtacat | cattttgctt | aaagtcacag | 120 |
| cttacgagaa | cctatcgatg | atgttaagtg | aggattttct | ctgctcaggt | gcactttttt | 180 |
| ttttttttaa | gacggagtct | ctttctgtca | cctgggctgg | agtgcagtgg | cgtgatctgg | 240 |
| gttcactaca | acctctccct | cctgggttca | agcaattctt | ctgtctcagc | ctcccaagta | 300 |
| gctgggatta | caggcacccc | ccgccacacc | cggcttattt | ttgtattttt | agtagagaca | 360 |
| gggtttcact | attgttgtcc | atgctggtct | cgaactcgtg | acctcatgtg | atccacccgc | 420 |
| ctcggcctcc | caaagtgcag | agattagaga | cgtgatccac | atggcccagc | aggaccactt | 480 |
| tttagcagat | tcagtcccag | tgttcatttt | gtggatgggg | agagacaaga | ggtgcaaggt | 540 |
| caagtgtgca | ggtagagaca | gggattttct | caaatgagga | ctctgctgag | tagcattttc | 600 |
| catgcagaca | tttccaatga | gcgctgaccc | aagaacattc | taaaaagata | ccaaatctaa | 660 |
| cattgaataa | tgttctgata | tcctaaaatt | ttaggactaa | aaatcatgtt | ctctaaaatt | 720 |
| cacagaatat | ttttgtagaa | ttcagtacct | cccgttcacc | ctaactagct | tttttgcaat | 780 |
| attgttttcc | attcatttga | tggccagtag | ttgggtggtc | tgtataactg | cctactcaat | 840 |
| aacatgtcag | cagttctcag | cttctttcca | gtgttcacct | tactcagata | ctcccttttc | 900 |
| attttctggc | aacaccagca | cttcatggca | acagaaatgt | ccctagccag | gttctctctc | 960 |
| taccatgcag | tctctcttgc | tctcatactc | acagtgtttc | ttcacatcta | tttttagttt | 1020 |
| tcctggctca | agcatcttca | ggccactgaa | acacaaccct | cactctcttt | ctctctccct | 1080 |
| ctggcatgca | tgctgctggt | aggagacccc | caagtcaaca | ttgcttcaga | aatcctttag | 1140 |
| cactcatttc | tcaggagaac | ttatggcttc | agaatcacag | ctcggttttt | aagatggaca | 1200 |
| taacctgtcc | gaccttctga | tgggcttrca | actttgaact | ggatgtggac | acttttctct | 1260 |
| cagatgacag | aattactcca | acttcccctt | tgcagttgct | tcctttcctt | gaaggtagct | 1320 |
| gtatcttatt | ttcttttaaaa | agcttttrct | tccaaagcca | cttgccatgc | cgaccgtcat | 1380 |
| tagcgcatct | gtggctccaa | ggacagcggc | tgagccccgg | tccccagggc | cagttcctca | 1440 |
| cccggcccag | agcaaggcca | ctgaggctgg | gggtggaaac | ccaagtggca | tctattcagc | 1500 |
| catcatcagc | cgcaattttc | ctattatcgg | agtgaaagag | aagacattcg | agcaacttca | 1560 |
| caagaaatgt | ctagaaaaga | aagttcttta | tgtggaccct | gagttcccac | cggatgagac | 1620 |
| ctctctcttt | tatagccaga | agttccccat | ccagttcgtc | tggaagagac | tccggtgagt | 1680 |
| agcttcctgc | ttgctggctg | ggtttccccc | cacggagga | gtcctctcac | tcagcacctc | 1740 |
| cggcagctca | gctgtgcaca | tgggcactgg | gggaaggatc | ctggcagcag | ctctgctggg | 1800 |

```
ctctgtcttt aagtgtgaag cagggaggag aggaacaggt ctcagatatt tcaccaaatc    1860
tcagcaaaat ccagagggag agcgcaggag gtggggtgat tcttatgctc tggctctttc    1920
tctctgaaaa aaaaaaaaaa atcttgcttt ttataaaagt gggtggaact cagtttaatt    1980
catcctgtaa aataaatat tcctttctca gaacaaattc cagacagccc agatgtacct     2040
gttcgtttta atattattca tcttggtaag attatttcag tttctctggc taaaatcatg    2100
atgttattct tctttaattt accaatggcc attcttctg aaacacagaa accctagaaa     2160
gagaagagtc ataggcaagg aattttttc atgcataaaa tgttggggtt aaagagagag     2220
agacctagca atcgctttgg tccacctacc tcacctcata agtgaggagt caaggcacac    2280
tagagtgaaa tatatctagt gggcacatga cagagcccgg attaaaactt tgttttagga    2340
aactctccca gcctctgggt ttcatttaca gtgatcgcca ggagggaaat cacattcccc    2400
tggctcacct ctctgatcat ccctccagtg tgactcttgt tcttaattcg agaaatattt    2460
attgagcatc tactagtgcc agcactgggc aagcaactgg ggggacagca gtgagtaaga    2520
aagaccaaaa ttccagctgt cttggaacct agggtcctga agggaagatg ggcattgaac    2580
aagagtgaca ttgtcaggag acgatgttct gggtgccaca ggatcatgtg gcaaggagag    2640
ctaacctggt ccagggagac aaaccctctc tgaggaaatg atgacaagct gagacccaat    2700
actattgatt agccatggtt ttctttaacc taaggtgggc caggcatggt ggctcatgcc    2760
tataaaccca gcattttgga aggcccagc tggaggattg cttgagccca agagttagag     2820
accagcctgg gcaacagggt gaaaacctat ctcttttgta ctaaaaattc aaaaaattat    2880
ccaggcatgg tggcacatgc ctgtggtcct agctactcag aggctgaggt gggaagatca    2940
cttgaactcg gggagtttga ggcagcagtg agccgagatc atgccactgc actccaggct    3000
gggtgacagg agtgagac                                                 3018
```

<210> SEQ ID NO 2
<211> LENGTH: 11451
<212> TYPE: DNA
<213> ORGANISM: Homo sapiens
<220> FEATURE:
<221> NAME/KEY: misc_feature
<222> LOCATION: (1)..(11451)
<223> OTHER INFORMATION: /label= Figure 8b

<400> SEQUENCE: 2

```
gatccacccg ccttggcctc ccaaagtgct gagattacag gtgtgagcca ccacgcccag      60
ccgacactgc cctaactctc aagttgcatc cttactcgaa tagtatgaca gtgtgggaag     120
cagcatggga caatgtaaaa aggaggcatg tttctggctt ctgctactta ctagctgtgt     180
gtctttgcac gagtttctta acctctctgg gcctcagttt ccttatctga aaaataacaa     240
tgatagtatt cccttcacag ggccaaatgg aatactatca ggaacactac ataatggaac    300
tcaataaata atagctactg cggccgggcg cggtggctca catctgtaat cccagcactt    360
tgggaggccg aggcgggtgg atcacaaggt caagagatgg agaccatcct ggccaacatg    420
gtgaaaccgt atctctacta aagatacaaa aattagctgg gcatggtggc gcatgcctat    480
agtcccagct actcgagagg ctgaggcagg agaatcactt gaaccccgga ggcagaggtt    540
tcagtgagcc aagattgcac cagtgcactg cagcctggcg acagagtgag actccgtctc    600
aaaaaaatac ctatctatct atctgtctat ctactgttat tcttacctgg tcatttcctt    660
tttgtttcac aggaaatttg cgagaatccc cgatttatca ttgatggagc caacagaact    720
```

| | |
|---|---|
| gacatctgtc aaggagagct aggtaggaaa gtgcctcagg tcagatcctg ccagatgatc | 780 |
| aagggtgat tacaaggtgt gatcccttc caggaggtaa agggacaatc tgtgcttgct | 840 |
| tccagtaact ttttggaaga ttttttataa cagttgcttt atggtcgttt atctacatgc | 900 |
| tggcgattgc ttcatttcct cctacatgcc tctttagcac tctgccatgc atcacagggg | 960 |
| gtatctgcat cctgtggcct cctctccagt atctcaagga cacttacata ccccactcag | 1020 |
| catgacaaaa gccctgcttt tcactgtatc gtctttcttg gaagacagct ctgtgactgt | 1080 |
| gcaccaagca tgcccttgg gcatggagat tctagataca cacacaaaag gcatcgccaa | 1140 |
| ggaaagcact tgtaactgga acccttggtt taaattggcc cagcatagct ccatctttaa | 1200 |
| aagagtcttt ccacaaagat ggcatccgcc atgtggatga gcatccaatt ttctctttga | 1260 |
| ttggttagct tgactgctcc atctgatctt cctctctctc gacctcttgt tcagaaagta | 1320 |
| ttgtctttgg tgtggactat aagcaagctc tgtgaagtaa aattggagag aacaccaaca | 1380 |
| gaaacaattt aaatttgagg aaaagggggc acctaagacc aaaggaattt ggcttatttc | 1440 |
| attccagaag gggaggctga gaataaatca gatgaatatc tgggttcctg cacctgaggg | 1500 |
| aaggcttcct gcagagccct gggcataata atctgggacc ttcaaaccaa taacctcttt | 1560 |
| tccaaggaaa gactggctgc ttccaaggag ggtaggggag agtcgggctg caggcagctc | 1620 |
| tcaagtctcc ccttgcacac tctcaggttg gcattttcac tttaacccat cctcccttaa | 1680 |
| gaaggcagtt ctttgtgacc agggtacacc ccctattata tatatatata cacacacaga | 1740 |
| gagagagaga gagagagaga gagagaaaga gagcaaagtg ttacctccaa ctacatacag | 1800 |
| tactctgtca gaaaagaggt tcagagaata agaaaacgtc ccgagctcat tccgttgcca | 1860 |
| gcaatgtctt actgccccct atagacgggt tccagggcag ctgcctacct ggccttcctt | 1920 |
| ccaatacaaa tcatcttggt ggatggttct ctgaggctca gtcttcgctg aagtcagaag | 1980 |
| aggaattgga ctcacattgc aaaggcacag ggcagggcag atttcctaca ggtgttagga | 2040 |
| agaacaaccc agttatgatc acctactgct ctgtctccat tgaggcctaa aaaggaagtg | 2100 |
| agtttatact gcagttggag gaactgcctg cagccttgag gaaaatgtct agtcacaagg | 2160 |
| gagtaagtta cctgttgatc atattgtcaa ggaattcctg tccaattctc cttccctggg | 2220 |
| ttgacacctc tgtaaggtca gatctggaag taggagagtg ggcaccaagg gagtccccgt | 2280 |
| tcagggaagt ggagtggctg gctgggattg gggcttttc ttcccaggag gagcaggagt | 2340 |
| gctcacgatc tgtgccctgt gtctgcctga aggggactgc tggtttctcg cagccattgc | 2400 |
| ctgcctgacc ctgaaccagc accttctttt ccgagtcata cccatgatc aaagtttcat | 2460 |
| cgaaaactac gcagggatct tccacttcca ggtgaggtaa tgagagtgta gttaagaggg | 2520 |
| ccagcggcag gccacccacc gctggtctcc tggccttgac ttcccagaag ctggaggaaa | 2580 |
| cttcccaccc atctacccgc agcggcaaca gtcggcatgg acccccttaa ggcttcaagc | 2640 |
| ctgggaggaa gcagttgctt atctctggct ccctaatccc tcccccacca ccttccacta | 2700 |
| tgtcccagaa agacaggaag acatcctgtt tactgtgggt ctattttgt ctttgcagct | 2760 |
| gtctggctgc ttttattgcc tgcagcccctt ctcaagtagg tccctaagat attagcactg | 2820 |
| tgacaccaca ggaccttca ggttgtacag gaaccctgt ccagggctcc tgtatacttc | 2880 |
| ttcctctcta aggcatggcg gtaccaaggc tatcactcct ctcttccaag ccctggaaga | 2940 |
| agagtctgct taacctgggg atcaggcttc ttgtttgccc tagaactgaa tctgatggtt | 3000 |
| ctagaatcca tccagctact ggaaattttc tgggtcccag tcaccttggc atagagctgg | 3060 |
| tgctagagca gaaccaaact gaattctacc tgtgagggtc tcgtagcttc cgggatgctg | 3120 |

```
gggagtcagc ctgtctccag cttcaaaggc tccctcatgt cccaggatga cccacattat    3180
cagttcttgc tccccgggtc ttgcacctca gcacggaagg cctcagaaaa ggtctgtctc    3240
caggctcaga ctcccccctcc tgccgccttg ggaacatggc atatttaaag ggtctcagat   3300
ctaaagggcc ttacatacaa atatcagata gatttctgtt ctcatttcaa tgagggagaa    3360
agtgccattg aaaaggagac taaaccacat ttggcccttt tcagttcaaa ctgattcatt    3420
caaaaaagag cgacatccaa acttgaaatg attgaacaat gttcctgcta cagctagaat    3480
agattctggg tcactttgtt cctccgtttc aatccttgtt cttcagtttg gcatcaagaa    3540
atacctaaat cagcacagtg ccttcactgc atagttccca atcctggcca cattgaatca    3600
gctgggggca cctgagagtg ctgacaccca ggccctgccc cagacctgct gagcaggaga    3660
atgaaaatct tacatcctaa gacactcatg gagcacctac tctacccatt actgggctgg    3720
actctgtgga agacatgaag tatatgtaac tcacttccag ctctcaaaaa gcacccagtc    3780
cagttagaga cagatttaca caccccaaac acaaaatagg atgaacaggc acccagatgc    3840
agagtccagg aaatgatgct gctttgggat tcaagaaccc cctgaggaat gtggaggaag    3900
gacacatttc ctaacagtaa tttgagtatg tgactctgtg cgtgacgctt ctgtgcagtt    3960
ctggcgctat ggagagtggg tggacgtggt tatagatgac tgcctgccaa cgtacaacaa    4020
tcaactggtt ttcaccaagt ccaaccaccg caatgagttc tggagtgctc tgctggagaa    4080
ggcttatgct aagtaagcaa cactttagaa tgtgaggtgg ggctagaggt gagaaagtgg    4140
gttgcaaaat ccagccgaga cctcactcac aggaagaggc atgtgcctct atacgtgcat    4200
atgtgtgggc atgcaagtcc aactgtgacc caaagttaga gatcagttcc aggcaacaac    4260
agctctaact aaaaacatta aatttaagag tagaaatgaa gatttgcata gaagaccttt    4320
agctttagct caccatagcg agttctttca ttgcacctcc atggtggcat gcaagtcttg   4380
gggatcagag cattgtccca gggtctcgat tggctcaacc tcatgtgctt atagaagatt   4440
tataaagaca tgttgtctct caacttaaaa gctccacccc agatgataat aatggatttt   4500
caaattttgg aacaaggtca ctctgtaatg caggctggag tgcagtggtg cagtcacgga   4560
tcactgtaga ttgacctcct gggttcaagg tgctcctccc acctcagcct cccaagtagc   4620
tgggactaca tgcgggcatc accatggccc ttttattttt gtattttttt gtagagcggg   4680
gttttcccat gttgacccag actgttctcg aactcttggg ctcatacaat ccaccagcct   4740
tgccctcccg aagcgctggg attgccggtg tgagccacca caccggcagc tgctaatggc   4800
tttaatgcag cccttcctca acgttcagga tgtagtggaa agagctctca ggaagtgggg   4860
atagctgggt ttcaatccca gtgcttctgg ctctctgtgg tcttgggtgg gtcacttagc   4920
ctcttgagct cagtttcttc attatgaaga aagggaatca ttgtttccat cccatgagct   4980
cataggghttta atgtggaatt gatgaaagaa catcacagca tccaagaggt aaagttctgg   5040
tggcagtggt acctgggttt tgttccctgg aactctgtga ccccaaattg gtcttcatcc   5100
tctctctaag gctccatggt tcctacgaag ctctgaaagg tgggaacacc acagaggcca   5160
tggaggactt cacaggaggg gtggcagagt ttttgtgat cagggatgct cctagtgaca    5220
tgtacaagat catgaagaaa gccatcgaga gaggctccct catgggctgc tccattgatg   5280
taagtctggg gtgtgggggca cagggtgggg agctccaagt gtcaggaagc ctttacccca   5340
atgaagggca gcatagagct tttgtgtggg acagagcgaa tgttttgttt gaggaagcag   5400
gaactggctc tcaactttga ggactgggaa tttctcaagg gagaacagtt cttccggatt    5460
```

```
ttcaataaag acactggtca aggacatttc aagccctgga atgtcagtgg aaatcagtcc    5520
agaggcctgt gtcagtggag gcctcccttg ctggtgctcc tcagtctcag cacgctccca    5580
ttaagctggc cacgtacttg gctgtggacc tgagcccacc atttccctaa gaaagcctcc    5640
cagtcactgg gctttcacca cacctccccg cttgagacgt gggctttgtg ttgttacctg    5700
ggagaagcta agcctgcagc acctttcagt gcaaagaaat gctgtgaact gagacaggag    5760
ccaagggtag ggagatggcc gcccatggcc aggcctcctt caggggggcat gccttccctg    5820 agggctgctc agtatattga tatgataatc ttagtggttt ccattgggga ggatggggct    5880
gaagctgaat tcctgcccct tcttctccca acacgcccaa tggacagctt ggaaggtcag    5940
ttagcacaca acaccatgga tgaacttttt ttctgtatca cttttctccg tctttcctcc    6000
attcgtgctc tgttgatctc tcctctctcc ctttgtctgt cccatctctt tctcctctct    6060
ccttcccttt ccacccttct gtgtttgttc tctccctccc ctgtgttgtt ccctacattc    6120
tccatcgggc tcaggatgg cacgaacatg acctatggaa cctctccttc tggtctgaac    6180
atgggggagt tgattgcacg gatggtaagg aatatggata actcactgct ccaggactca    6240
gacctcgacc ccagaggctc agatgaaaga ccgacccggg tgtgtacacc tccgattatc    6300
agaactgacc atccctccaa cccacatgac cccgccctat tagtgtcaga ctcccctcag    6360
cagccagggc cttacccaca cacccccacc tggcacctcc caagggtctg ggttgaaata    6420
acttgctcag ccaaggctcc tgaagagggt gcaagaacca ggattttgga gggaatctct    6480
gctggagttt ctgcatattc catggtccag gcagttcctc tcataacgaa ctatcagaca    6540
gaaatacttg taaagatact tcatttattt tgaaatattt ttcctcttct aatgtattca    6600
tttattcatt caacacttat ttttgagctc ctactatgtt ccaggcactc ctctagcaaa    6660
caaagcaaat tctctcctct ttttcaatat ttgtggaaaa agcaaggtct ccctcttgta    6720
gagtttatat tctagtattt tcataagtta tacctgctca ctggagaata ctgagccata    6780
cagaaaaaca cagaggaaaa tttcacttat atttttcccc atgtaaagat aaccactctt    6840
aacatctagt atatgttctt ccaggatttt tctatgcaca cactgaatct gtattttat    6900 ttttaaaatg ttatcatatt gtatgtacct ctttgcagcc tgcttttttc agttagtttt    6960
tttggttttt tggttttttt ttttttttgg aaaccaagtc ttgctctatt ccctaggctg    7020
gagcacagtt gttgccatct cggctcactg caacctctgc ctccaaagtt aaactaattc    7080
tcctgcctca gcctcccgac atagctggga ttacaggcac acaccaccac acatggctaa    7140
tttttgtatt tttagtaga gacggggttt caccatgttg gctggaatgg tcttgaactc    7200
ctgacctcaa gtgatccacc tgcctcagcc tcccaaagtg ctgggattac aagtgtaagc    7260
caccacaccc ggcctagttt gatattctta atgtgcccaa agtattctcc tgtaacattt    7320
tttaatagct acacaatatt caaacacaca gatatgttat aatttattta cccaatacccc   7380 tattattgga aagttgagtt ctttttttc tttgttttgt tttgttttgc tactattcta    7440
aaatgctata cgaacatcc caatagatac atctttgtat acatccatgg tgacttccat    7500
aggacagatt cccagcagta gaattgctgg gttgaatgat atgcttaggg taatgacaga    7560 agagtcatt caagcagctt cctagggtct tagaacttaa ggattaatga gtcttcccgc    7620
cccctcccag tctattcagc atgatctgga tcatgaggac tgagatctgg aagagactga    7680
gatctgggag aggctgagat accaaaagcc ctggctccac ccatacccct cgccctgaaa    7740
acagctctag gaattccgcg gcctagcaag gctccgggaa gctccttta aagctgtgac    7800 gttagtaggc acatggacca tagagaccta tccagggctc atgggacttt agtgatcctg    7860
```

-continued

```
cccttctccc aaggatcccc catggctgca acttggaaat ttctgcaaat ggaagagcta      7920
ctccttaggc acggtcatgt ctgagcaggg atctcctcgg gctttcttag aattctctcc      7980
ctgggcactg ggactcttga tttcttgaat attatgttcc aggtgggtgt ggaggaggtg      8040
aggggatgta agaaggcta gacttggcca ggcgcagtgg ctcatgcctg taatcccagc       8100
actttgggag gctgaggcgg gtggatcacc tgaggtcagg agttcgagac cagcctggct      8160
aacatggtga accccgttt ctactaaaaa tacaaaaaat tagctgagca tggtggcacg      8220
tgcctgtaat cccagctact cgggaggctg aggcaggagt atcgctggaa cacgggaggc     8280
agagattgca gtgacccgag atcgcgccac tgcactccag cctgggcgac acagcaagac     8340
tctgtctcaa aaaacaaaaa agaaagaaaa aaggaaaag ctaagactta catgtgtcac      8400 ttaaccccctt ttctcaaacc tctttctctt ccaggaatag tcaacccctg gatggcttca    8460
ggggaagggg gatcctgaag cccagggcag cctccaactc taccccttcc tcctttgaag    8520
gatactaagg ggtccagaaa ggaggggcag gacactgtta cccaccccac atcccagcat    8580
ccacattgct ctctgatggt caggacagag ccttctcagg gagaccagcc tgtctggagc     8640
tgtgtctctt ggcactctta aagggccact gaaggtccgt tcgtggtcgt gaggcacact    8700
ttcagggagc agagtggtct gtgtcttcac agagcccgga aaatgaacta gtatgaactt    8760
tgcctccaag cagcagaact tctgttcccc cgcccctaat gggttctctg gttactgctc    8820
tacagacaat cattccggtt cagtatgaga caagaatggc ctgcgggctg gtcagaggtc    8880
acgcctactc tgtcacgggg ctggatgagg taagcctggt ggggcttggt ggggcaaggg    8940
caccctcctg ggttaacctc atgaagtcag gacttagctg ttggggcccc tgccctgtct    9000
gcagagcttg cctccaatca ggacattcag ttcaaggtcc aagccacgcc tgggagcaga    9060
ggggcctgtg aaactggtag aggtggatcc tgccacagtt ggtgcacagt ttatctttgc    9120
ttttcgtgct aaagatggca attttttccaa catttccaat gaacaaattg aaatatcact   9180
taactttgct tttacaaagt tggtttcatg tgttcttgag cttcctgttc tctcgtgttc     9240
agatagctac agttgtctct gggtagccac ggggactggt tccagaagcc caacagtaa    9300 caaaatctgc agatgctcaa gtcccttctg taaaatggag tagtatttgc atataaccta    9360
tgcacatcct cccatatact ttaagtcatc tctggattac ttacgatacc taacacaatg    9420
gaaatgctat gtaaatagtt attgcactgc attgggtttt tttggtatta ttttctgttg    9480
ttgtattatt attttttctt tttttgaata ttttgatcc acaattggtt atatgccaaa     9540
gccatggata cgagaggctg actgttctgt tttgctcctt ctgggacttc tgggttttcc    9600
tggaccatgt ctgagacagg aacgttgtaa gacctgttgc acacagttgg gcaggttgtg    9660
ccctgtacag agggatgggc tgagagggc agttgcctgc atcacccatt gcagcagact    9720
ggagggagtc tgcttgtttg tagttcctca gtcagcaggg gccttttgtc tttccttcct    9780
ttcctttttt tttttttttg agacggagtc tcactctgtt gcccaggctg gagtgtagtg    9840
gcacagtctc ggctcactgc aatgtccgcc tcctggattc aagcgatttt cctgcctcag    9900
cctcctgagt agctgggatt acaggcgcgt gtcaccatgc ccagctaatt tttgtatttt    9960
tagtagagat gggggtttct ccatgttgat caggctggtc tcgaactcct gacctcgtga    10020
tccgcccacc tcggcctctc aaagtgctgg gattacaggc gtgagccacc acgcctggcc    10080
agcaggggcc ttttttctaa tttatatgaa gacacctaat ttatatgtgt tagcaaagcc     10140
ctcctgttta tgcctcacct cctcccccga agctcatacg gcaggatgtt cctgagaaaa    10200
```

-continued

```
ttgcctctta gaagatagag aggagatgcc aagcctaagt taggcagact caggaggata    10260
ggtctgaccc acccctgcc attccccagc acacttgtga ttaatctcct tggccagagc     10320
caggcagaac accctcgcgt aagagatttg ccccccagcc ccgtcccagc cctcagctag    10380
acagaagatt ccctttccag agaggctgca gagcatgaga gctctttctg tgtgcttaag    10440
gtcccgttca aaggtgagaa agtgaagctg gtgcggctgc ggaatccgtg gggccaggtg    10500
gagtggaacg gttcttggag tgataggtag gtgagggac cccacgggat tggcggtggc     10560
ggggaacagg gtccgggaca aggctgtgtt gggaactgag ccatgagagt attgaagatg    10620
cttggtataa aatcaccctc aaaaccaatg atccgcagag aagaggggca caggtgttgg    10680
ctccagggaa gggccaggag tggaagcggg gtgctgggga cccagagagg ttgctgacaa    10740
ccattggctg gaaaggaagg attccagaaa gcgtggggaa ggtccaggca ggaaaagcgt    10800
atgaatgcag ggttctgggc tagagaagtg acttcccttc ttggggtctt gtgttgcctt    10860
tcctgtgaaa tgggaacagt attattagca cttaccttgt gggctgatat tgaggagtaa    10920
ctgggacttg ttttttgggca agtgctgagc cattgctaag attcccctta cccgtgcttg    10980
tcccttgtat taaggcacaa gggcccttttg aaaagaattt tacctgctttt atcaattgaa    11040 agggattaag accttgggg ccaacccaaa ataaacatgc gaacttatta tttataggct       11100
ccatgcacac ttcgtaaaac ctccatggtc ctactggttc ctgattacct ccactcaatg    11160
agaggcaatt cattactgaa tgagccataa gcgcctctta tttcgagagg gggatggcag    11220
gactcagtcg aggagaagga ccgcacccag gcagcctggg cccctcggct cctgtactta    11280
tttactgctg ggtacttcct agcccagcat gtaattactg gttcgttcag tcattcgttt    11340
agtaaatgtt tcttgggcac ctactacata ggaggcacag gtcaaggcac tgggatatt    11400 ctttctaccc accccctccc ttgatacact gtgattaggg actgaccgat c            11451
```

<210> SEQ ID NO 3
<211> LENGTH: 1834
<212> TYPE: DNA
<213> ORGANISM: Homo sapiens
<220> FEATURE:
<221> NAME/KEY: misc_feature
<222> LOCATION: (1)..(1834)
<223> OTHER INFORMATION: /label= Figure 8c

<400> SEQUENCE: 3

```
attttttttt ttttttttga gacggagtct cactctgcca cccaggctgg agtgcaatgg     60
cgcgatcttg gctcactgca acctccgcct cccgggttca agtgattctt ctgccttagc    120
ctcctgagta gctgagacta taggtgcccg ccaccacgcc cagctaattt ttgtattttt    180
attaggacgg ggtttcacca tattggccag gctggtctcg aaatcctgac cttgtgatcc    240
gcccacctcg gcctcccaaa gtgctgggat tacaggtgtg agccattgcg agcagcccag    300
aactcaattc ttaaccttta aagtatgatg agaagaagga tcaagccctc accagcccat    360
ttaaggagtt taggctcagt cttgaggatg tgagaagtca ttgctattgg gtttcacact    420
gaggttaaca ggtgaagtca gcattttggt agttcacagc agctgcaact cttttgtattt    480 ctctgatacc tcctgtccca acctacatca ggccttccct tcttcctgct tccttaattc    540
ctccattttc ccaccagatg gaaggactgg agctttgtgg acaaagatga gaaggcccgt    600
ctgcagcacc aggtcactga ggatggagag ttctggtgag tccagaaccc aggaagaccc    660
agaagggtaa gggtgtgggaa gagagggaa atctcagacc tcagtcccca gctaaggtta    720
tcagattcca gcccttggga gatcttggct gtgttctcct ccagcccaag gcccagcaag    780
```

```
gatgaggttc tgagaggagc cttccaggcc acagggacaa tgagcccagg accaggccaa      840
catgacatgg ctcttgcctc ctgtgtgccc ctccgccaca cactctattc cagccacagg      900
caccctggcc ttagcacaat tcttttctga gcctaggaag ctccacttac cctgatcttc      960
caacgtcaac ctcaccctct ctcaggttgt ttctattcag gcttcaagtc tcagcttaag     1020
gagaattttc aagtctcagc ttaaggagag cccctaagt tccccgagga ctgggattaa     1080
tttatgatgc tcatcaccct taaaattgtt tgcttaagcc gggcgcggtg gctcacgcct     1140
gtaatcccag cactttggga ggccgaggtg aacggatcac gaggtcagga gatcgagaac     1200
atcttggcta acacggtgaa accctgtctg tactaaaaat acaaaaaaa agtagccggg     1260 cgtggcagcg tgcgcctgta gtcctagctg ctggggaggc tgaggcagga gaatcacttg     1320
aacctgggag gcagaggtta cagtgagccc agattgcgcc actgcactcc agcctgggcg     1380
acaagagaga ctctgtcttg aaaaaaaaa aaaaatgtg gtcttagttt aatgtcaagg     1440
gaaaggtttt gggtgttttt attactttat tttttattta aaactataa tagagacggg     1500 cctcgctata tttctcgggc tggtctcaaa ctccctgggct caagcggtcc tcccaccttg     1560
gcctcccaaa atgctggcat gtgggcctgg tcaacatatg ggaccccaac tctacaaaaa     1620
attttaaaat tagccagatg tggtggcgtg tgcctgtagt cccagctact gggaggctg      1680 aagcaggggg tcacttgagc ccaggaggtt gaggctgcag tgaactatga ttgtcgttca     1740
cttttcttct gaacgtgaga ttaagtgtag tcagcaattt ggcttaggat tatttattca     1800 gaattttaa ccgtcacgtt gcggcaaacc aggt                                  1834
```

<210> SEQ ID NO 4
<211> LENGTH: 14664
<212> TYPE: DNA
<213> ORGANISM: Homo sapiens
<220> FEATURE:
<221> NAME/KEY: misc_feature
<222> LOCATION: (1)..(14664)
<223> OTHER INFORMATION: /label= Figure 8d

<400> SEQUENCE: 4

```
aggaggtgga ggttgcagtg agccaagatc atgccactgc actctagcct gggcaacaga       60
gcgagactct gtctcaaaaa atacacacac acacacacac acacacacac acacacacac      120
acacacatat atatacacac atatatatac acacacatat acacacacac acgtctgtat      180
atatatgtgt gtgtgtatat atacacacac acactattct atatattctt gtagagctat      240
gtgtgtctcc tgtgctattg agcatgagcc cttttttttt tttttttttt ttgagacaga      300
gtctcacttt gtcgcccagg ctggcataca atggcgcaat atcggctcac tgcaacctcc      360
gcctcctggg ttcaagtgat tctcctgcct cagcctccca gtaactagg attacaagtg      420 cccgccataa tgctcagcta attttttgtat tttcagtaga gatggggttt caccatgttg      480
gccaagctgg tctcaaactc ctagcctcag gtgatccacc tgcctcagcc tcccaaagtg      540
ctgggattac aggcatgagc cacagcaccc tggtgagcac tagagcttat tcttctatc      600 taactgtatt tttgtatcca ttagccaccc tcttttcatc ctcccctctc cttcccttcc      660
cagcctctgg taaccactgt ctgctctcta cttccatgac atatgctttg ttttagctct      720
cacatatgag tgagagcatg cgacatttat ctttctggcc ctggcacatt tttgaatcat      780
tgttagaaaa gatgatggtt tggagtagat acatcagaag tgcagcgtt tgccctaaaa      840 aggaaagaca ggctcctctg ggaccctgac caagttcctg tgaactattt tattattgtg      900
```

-continued

```
ctgtgttagt cctggggtct tccgttccca gccctcctca cctgctccca tatggctctc    960
tctcttcttc caacctctca ggatgtccta tgaggatttc atctaccatt tcacaaagtt   1020
ggagatctgc aacctcacgg ccgatgctct gcagtctgac aagcttcaga cctggacagt   1080
gtctgtgaac gagggccgct gggtacgggg ttgctctgcc ggaggctgcc gcaacttccc   1140
aggtgggaga tgctcttgat gggggaggg tctaagccga aaagttcca ggcagaagaa     1200
gcctaactag tgcttattaa gtctctctgt tccagacgtc cactatctta ttaaaccttc   1260
cctgttttac tgagaaggaa accaccatgc tgagaagttt gcaataggga gctgggtagc   1320
aactttggaa gcaggaactt gtgggaacaa tgcagatgct gcttggactt acgatgaggt   1380
tatgtccaga taagcccatc catcttttga aaatacccta agtgaaaagt gcatccaata   1440
tgcctaaccc cccaaacctc atagcttacc ctggcctacc ctcaaacatt gctcggaacc   1500
cttgacctta agcctaaagt tgggccaaat catctaactc caaagcctat tttacaaaga   1560
aagttgttgt aatatctcca tgtaacttac ttaatacttg tacctaaaaa gtgaaaaaca   1620
agaatggttg tacgggtact cgaaatccag tttctactga atgtgcatct ctttcacatt   1680
gtaaagttaa aaaattgtag ccgaaccatc ctaagtcagg gactgtgagt actgtgtcag   1740
taacagtaag ggcactattg gagaaccaag ttagcagctg ctgcaatagt tcaagtcaga   1800
gatgatgaaa acctagacca agtcagtagc agcagagatg gaggggagac agcagattta   1860
gggagagcat attgggtgat gtagggaagg aagaagaatg atgtcaagat tcccagttgg   1920
ggacctgaca acattgcaac ataagacaca caagaagatc gggtgggtgg ctcatgccta   1980
taatcccagc actttgggag gcagagccag gaggatcact tgagcccagg agttcaagac   2040
cagcacaggc aacatagtga cacctcatcg ttacccaaaa taaaaaaaaa aatgaggtgg   2100
gaggattgct tgagctcggg aggttgaggc tacaataaac tgtgatcatg ccactgcact   2160
cctgcctggg tgacagagtg agaccctgcc tcaaaaaaaa aagacacaca agagaaaaat   2220
atcagcgtgt tgtttgtttt tggtggagtt aattgtgggg ttctagggaa aggaatttag   2280
cttgggacat ggaaagtttg aggttcctgt agagtgtccc agtgaagatt tgtaatagag   2340
catcggatgc gcatattaga tggcacttgg tgatatgata agaactcaaa aaatatttga   2400
ggaataaagg aaagaagagg ccagacgtgg tggcttatgc ctgtaatccc agcactttgg   2460
gaggctgagg caggcggatc acttgtggtc aggagttcga gaccagcttg gctaacatgg   2520
tgaaacccca tctctactaa agatacaaaa attaaccggg gatgatggtg ggtgcctgta   2580
atcccagcta cttgggaggc tcagtcagaa gaatcgcttg aacccaggag gcggaggctg   2640
cagtgagccg agatcgcgcc actgcactct agcctgggca acagagccag actccgtctc   2700
aaaaaaaaaa aagtgagaga gattgaggct gggatatatg gctcaggcat catgcgcgtg   2760
taggggggcag ttaaaaagca gaagtaagaa agattgccta gggaggcagg aagggtgagg   2820
tgagaggaga agaggcccag gaccagattc tagtcaccaa cagcgtttaa ggggcaggta   2880
aggaaaacaa aaccatcagc aaagactgag aatgaaagcc cagagaggaa ggaaaagcca   2940
cacatacaat cagtacagct ccatctgaat aaaggtagcg cccccccccc cccaaatcat   3000
tagagaaatg cctgattcgg tttttctgtgg attttttccta agaacctaga tgtgggaat    3060
agaaataaat ggttccctct gtctcatccc ctccctgccc tctgagagga agctgtgatt   3120
gcgtgctccc tttctggggg tgcagatact ttctggacca accctcagta ccgtccgaag   3180
ctcctggagg aggacgatga ccctgatgac tcggaggtga tttgcagctt cctggtggcc   3240
ctgatgcaga agaaccggcg gaaggaccgg aagctagggg ccagtctctt caccattgcc   3300
```

-continued

```
ttcgccatct acgaggtgtg tagtcctgat tggctccagc ccaggaaaca tactttccca    3360
gagaggacgc ttccaggggc ttctagaggg gccctctgct tcctcaatac cagtgaccca    3420
cagagctcct ggtatcagga ccacttgtgt ttgtaacaag caaaaaatac cagggggggc    3480
attagagagg cagtggagcg ggcctggcag aacaggtgcc tgggggtcag gcttccgcat    3540
gcgggctgca gttgctggca ttgccttccg caggctcctc atcctcattc acatctgaag    3600
catcttcctt tctgtttctt ctcaaggttc ccaaagaggt atagcagcag cagcggccag    3660
cagttgtgtg cagcactacc caggggggcc cgagtctgtc tgtggctcgt cgagaagctt    3720
cctggtgggg tttgtgggca ggacttgtga taggagaggg ccttgcctgt tgttatttcc    3780
cacttgcaga gcaggttgcc tcagggcatt gcatgaccca tgactaccac ccccaggatg    3840
tgcactttct ccctcgcacc agacactgca cgtcacacac atgcctttgc acactcaccc    3900
tcctccacgc ttacagccac acacacagtc acacagacgc gttctgaggg tggctgcccg    3960
cttgggatgg aggaatcact tccctcagaa cccagccaag tcctctaggc ctccttgggg    4020
gtccttccag cctgagggc ttcggagctg aggacagctg ttctggtaag tgtccctgag    4080
tgtggggatg acacatttcc attcactctg aatcacaaca gaaaagggaa gaggaattga    4140
ggtagggagc ctatttaacc cttgggagtc gggaagtagg gaggttgaaa ctgtgacatg    4200
ggtgaccagg gagttgggaa gggacccttg gaggtggctg tggcaggaca ggacgttcct    4260
cccgaggggc tcatgtgccc tgggctctcc ccatctctca gatgcacggg aacaagcagc    4320
acctgcagaa ggacttcttc ctgtacaacg cctccaaggc caggagcaaa acctacatca    4380
acatgcggga ggtgtcccag cgcttccgcc tgcctcccag cgagtacgtc atcgtgccct    4440
ccacctacga gccccaccag gagggggaat tcatcctccg ggtcttctct gaaaagagga    4500
acctctctga gtgagtgctg gcccagcttt cccacgtgtt tctaaaagct cacatggccc    4560
actccagagg ttgaaggcat gaggcagcta gacacgtctc ctccagggtc cttctgctgc    4620
tcctgagcca ctggccacat taccccccatt cattcattca tccattctgt gatatttatt    4680
gagcacctac tatgttccag gcactgtcct aggcactaag gatagagtag tgaagtaaac    4740
agaaagaaat ccctgccttc atggagctta atattctaac atgagacaat aatggatagg    4800
aaaaacatat gtagcatgtt agatttggag aggtgatatg gagcaaaaat aaagtaggga    4860
agagggatag gaggtgttgg ggatgcttga aattttaggt tagcatggcc aggaaagcca    4920
catcctgtcc ctggccacca cagatgagct catagcccct gccactctga tctctgtcct    4980
tggaagatgc accaggtcca tgggtaggtg gctgggtcat gcctttgggg ggctctgagc    5040
aatactaaca agaacctgcg tgcctgggct tggctgtcgg ggatggtgct gacatggggc    5100
tggttcctgg ggttggggtg ttccaggggt tctctagagg ctggttctgg cttggctgcc    5160
aggaagccgt gcaccagagc aaaccgtcca cgggcctcct gcttgcttct ggtgacactg    5220
agaccccaca tgtctgtatt cctcacaggg aagttgaaaa taccatctcc gtggatcggc    5280
cagtggtgag tggtttagat cttctgtgcg aaaagtccag agggtcccct tccctgacca    5340 tgcagggac agatggtgca ggggagaatg ggcactggca gagggaatgg gagtctgggc    5400
tgtgctgagc agtccctcct tggcactgca aatcctactt tggcatggcc agaagtaatc    5460
ggccttaagc accgggggcc attgaggcag ttcagggggct gggaaatatg gaagagggtc    5520
ctggaaagga gaagcaattt gaacaatcgg agggaacaag gccacaggaa gggatgacaa    5580
gagccgcagc gaacactgga ttctgagact ggataacatt ggatttcaca catagagaaa    5640
```

-continued

```
agaaagtaag ctggtgccgg acctggtgtt gacacttgga tcctccactt accagcgggg   5700
tgacctggac aatttctgta atccctctca ctcagtttcc tactcagtaa aacgggatg    5760 ataatgtgcc ttgcaaggct tttgtgaggc ttcatcaatg aggtgatgta tgtgaagtgt   5820
ctggcacagc atgggcactc aaacagaggt gcttttcac  actttacacc ttacaaggta   5880
cttttcacat gtgtcatcgc gatacttgca aggttgctga gaggtagatg gggttataat   5940
ccctggtgtt caagaaagga agcagaggct caatggggtt gaatgacttc tctgagttca   6000
cagagctcag taagtggcag ggtttggaac tcacattcag actctctgac tccagactta   6060 ggttttccg  cacctccacg ctgaggccag ccccaggcag tgagaagccc aaagtccgaa   6120
gcacagagtg ctgtgtgttg ggctctgtgt gttgaggagt cttgtgactg ccttggggct   6180
ttgggctgta gtcagctgac agtccttttgt gctctgtggg gatgacgtag ccaatggga   6240 ggacaaatgc ccctctgaac tgtcttctgg gcagtgacag tcatggtcat aatcctgacc   6300
ctgagccagt gccaggtctc caagtgcctt ctgaatgacc acaggcgatt ggttttagtg   6360
gtaggtgcgt ggggatctgt tctggtcatc tggatgctgg tcatcgggtg cagtattgat   6420
caggacctgc aaacccaaaa gcttatggga gctggcacgt cacgtgagta gagcaggcag   6480
gtgcagggtt tttgatgtcc ctgcactgac acagttgtct gcagttctcc aatttgacat   6540
ttgggctcca gtgtcgaggg tcaaacaagg aattttgggg cgtgggccaa atctgggaag   6600
acacagggag cagggccctt tggctcaagc tgatagttgc cgcagggatt accaggccca   6660
gggcagcctg ccacaagctg gggcttttac caaagaaaat ctccctatgt taaatgcttg   6720
ctcaaaaatt tttaaaaaat attctgtaag tcaaaatcca ttgttaggtc agtttgagag   6780
agccatgttt ttggtgtttt agtaaccaat ttcatttttt tattatttat ttatttgttt   6840 attttgaga  cggagtttca ctcttgtcac ccaggctgga gtgcaatggc atgatctcag   6900
ctcactgcaa cctccgcctc ccgggttcaa gcaattctcc tgcctcagcc tcctgagtag   6960
ctgagattac aggtgcccac catcacgcct ggataatttt tgtatttttt agtcgagatg   7020
gggtttcacc atgttggcca ggatagtcct gaactactga cctcagataa tccgcccacc   7080
tcagcctccc aaagtgctgg gattacaggc atgagccagc acgcccggcc accaatttca   7140 tttttttaaaa aaggaagaaa gaaaaccttaa gccagaagat cttttttcctt gccatatgca   7200 gtaagagtag attataaaaa caaagtcaga gcagtcactg gtgtctgggc atggaggaga   7260
aagaagaatt ctcttctccc ttcaccctcc atgcccctttt ttggctccat gtgattcaga   7320
tttctggacc ctggagcccc accccaagct aaagaccagg atacagggaa gccacaacca   7380
ctggcggttc tgagaactta cttttcactt attctgcatt tactgtttcc ttttcttatg   7440
cagaaaaaga aaaaaaccaa ggtaggtgtg tgggtagaga gcatgaagtg tgtgtactca   7500
tgcatatgta tgtgcatgca tgtgaagtgt gcatgtgtga gctcatatgc atccatgcac   7560
cagacttgcc tcttcctccc cctccttcct gagcttctgc tggggccgag cgtgcagtaa   7620
tgacaactac gatttgctgg gggaaggcta cgtgccaagc actcttttag gtgctttcca   7680
tgattaattc cttcctcaca acagccctat gagattagta ctataactat ccccattttc   7740
agagggagaa aagtacaga  cttgactaac ttgcccaagg ccacacagcc agagagggc    7800 agagccagta cttagagcca ggcagtctgg gtccagagtc cgtgtcctga accacaagag   7860
gccatcatac gccatcagat ttggtgctag catttctggt ggtgcctggt ggtgatggat   7920
ccatcacagg ggtcctccag gtactggtgc tgcccagac  cagagctgac actcctcagg   7980
cactaccaca ttccaggcac tgtgcttggg gtcagtccct ctctttttt  tcccccccaa   8040
```

-continued

```
ttataacagt atctacaaag taggtgctgt tattttttccc ctttcacagg tgagatagac   8100
tcaaagaagt gaacttgccc aaggaacaga actaatgagt ggggaaaatg gaactggaaa   8160
ccatgtctgt ttactccaaa acctgtgttt cttgccctct ttctctgatg ccagccccct   8220
acacttcaag gcctgtgttg tccagaccca cactcgggcc tgccagtgtg tgcctggcag   8280
ggatgctcca tggccacacc atatccatcc tacacatccc ccctcagact gtgacctcca   8340
tttgctctgg gatccccaca agcttcagct gcttgagcaa gacactgctt agaaggcaga   8400
gcaagccaag gcctctgggg cctgctggga gccaaagctg gggagccgtt ccacgggtc    8460
tatctgcttg agctgtccta gatgagcagc atggaagggc agtggtgcat gagtccaggc   8520
gggctgcttt tctgctccga gaggctctgc ctgcccagtt gttctctgca ttgcagcctc   8580
aatccccaca gccttgcctt cccccggctt tccctacagg tgcaccgcat ccacagtgtt   8640
ggcaccatgc agcagccgct ctccgtcctt ttcatatcct tgtcacttgc acgagcatgt   8700
cttgaaaata tcccttgttt gtgtagcatc ttaaatgttt ttgcagtatg attttgcatt   8760
cagtatctca tttgatcccc acaagagccc tatgaggagg gaaagcagat tttaccatta   8820
aaggatgagt aaactgaggc cagagaggat atttttggtt ttttttgaga cagtctcact   8880
ctgtcaccca gcctggagtg cagtggcttg atcttggctc actgcaagct ccacctccca   8940
tgttcacacc attttcctgc ctcagcctcc caagtagctg ggactacagg cacccaccac   9000
cacacccagc taattttttt gtatctttag tagagatggg gtttcaccca gttagccagg   9060
atggtcttga tctcctgacc ttgtgatctg cctgcttcgg cctcctaaag tgctgggatt   9120
acaggcgtga accccctgc ccggccagag aggatatttc ttaatgaggg gcagggctgg   9180
gattccagcc cagtgttctg atggctcacc cactgaccat tccactaatc cgtgtccttt   9240
ttcaatctaa actttcaggg ttgtagaggt tcctttgagg tgcctcagta cttccatggt   9300
gatgtggggt ctgagggcca agagctctgt tctcattaat cagagaagct tgtgttttta   9360
aaaacaccat gtttactgca ggaaatttaa ttggacagtg tttccatctg gaaaaaaaaa   9420
agtctacaaa atacttgaca atcactgcac tagatcatgc tgcttttagc attcttagca   9480
tttcacgtgc tgagctctca atactctacc atgaggaggg atggagtggg tatgaaaaga   9540
taaagaactg aagtcacacg gcttgtcagt ggcagagata gagcttgaac cgaggttgaa   9600
gagctcccgc ctattccttt cctcttctca ctggataaag ctgctccaag agaggtgctg   9660
cctcagtgtg cctgttcaga ctgtaatcct cccttccttc ctgcctcctc cctcctctct   9720
ccagcccatc atcttcgttt cggacagagc aaacagcaac aaggagctgg gtgtggacca   9780
ggagtcagag gagggcaaag gcaaacaag ccctgataag caaaagcagt ccccacaggt    9840
gtctggcat gtggcatggg tggggtggcc agcacgctac aggggcttcc tatgcgcttg    9900
ggatacacag gggctggagg cttcccagga gtttgtcttg aacatctgga ggtttgaatt   9960
tgtcccactg acctttttctt tcagcaagtt cccctgaaat ttgggctgct gcttgggtga  10020
atatcccagg atgggggttc cattctagga gtggactggc aggctgagcc tcccatggag  10080
ctgatccagc caggatacag agaaggggag gcaaaggctg agacagaacc agcttgagag  10140
cggaggcgca actcttgtct cctggtggcc ttgagcattt cacaataggg ggataaagga  10200
taggagcaga aaagtgggc tgacttcaga aatgggtcc tctagagctc acgggagggt    10260
gttagattgg agtgggagct tagtggaggt gagccttaga ggcaaaagtc tccagaccaa  10320
tccaggcccc ctcttctatc cggggccccc tcttctatcc agggccctc ttctgtctgg   10380
```

```
gagcccctct tctatctggg gcctcatgca gtggggccta ggggaggttc tctgaggact   10440
tggccttgat gacagggtgg ctggaggaat cagaacggtc agaccttctt tgacctgcgg   10500
gcacctttag ttggaatgct caggcctggg atggtggagg gggctcttgc aggtggggac   10560
tggggtggcg gggaggaggc tgtatggccg ccatatctcc tttggctggg ggcgtcaggg   10620
ctggagaggt gtgaagagtc cctgaggcct cgatgcatct cactccagct caccaggtct   10680
gcatttgccc gtccccagct cctgctgcca ccccggccg ttttaggcac ttggctccct    10740
tggcccagag gagcttgcct cacaggcctg tgcacctctg accctgtga accagttttc    10800 ctttgtgcct ccacagccac agcctggcaa ctctgatcag gaaagtgagg aacagcaaca   10860
attccggaac attttcaagc agatagcagg agatgtgagt acctccaagc ccaggacgcc   10920
cacaggtgct tccttctctc ctggattaac tgctcagatt accaattatt tcattattgt   10980
ttggtagagg tcactttgga cttcggtgga gccaggggat gtgtgcgtag cacacaaatc   11040
cacaagccct tgagttttgg actgccacgt ctgctggggg gctcagaggc cttttttgctc  11100 tgagctgccc acggtggtcc tgatagctga ggtgcagtat ctggccccct gtcttcctca   11160
gaaaagcccc agcttcccat gacataatag caccgacagg gattttacaa acacagccag   11220
gtggaatttg ttttgcaaag tgtccgcgcc aggagctgct gtactcctga accatgaccc   11280
tcctctccct tcctcctcag gacatggaga tctgtgcaga tgagctcaag aaggtcctta   11340
acacagtcgt gaacaaacgt gagttgctca aaccaaatgg gggtggggtg ggtggggagt   11400
cccgttgtct caaagcagct cctcactctt tccatcccc ccagacaagg acctgaagac    11460
acacgggttc acactggagt cctgccgtag catgattgcg ctcatggatg tatccttcct   11520 gccgccctt cccgaccctc tgtcatcagc ccacggggc caaggcaaca tacagggtgc     11580
ccagtcaggc aaagggccct aatttgtgcc cagggaaact taaggagacc ctgattcaga   11640
acatcttgga tactcgtctg aaaggggttg ttagaggcgg aagggagga tgttgggttg    11700 taactgccct aaccctgtg cttctctcag gcctgggatc ctgcccaagc aaaagtggtc     11760
cttaggagag cggctcctgg gttacagagt aggcgcaatc tctgactggt ggtgagtgg    11820 aggggagggt taaatagtac aacagggcag tgggtaggac agcccggagt ctcctagacc   11880
ctccctccaa atccagggg atttgctgt gtgctgtgta gccctgacct ccctcctcca     11940
gacagatggc tctggaaagc tcaacctgca ggagttccac cacctctgga caagattaa    12000 ggcctggcag gtgggaagag aaaatgaagc gtgggagtca agaatggggt tgatttggag   12060
attcagtgtg tgacctccat cctcaaattt tctattgcca gaaaattttc aaacactatg   12120
acacagacca gtccggcacc atcaacagct acgagatgcg aaatgcagtc aacgacgcag   12180
gtgctgagaa ggaaggggtg tcaggatgt ggacccgaga cggtgggagc aggaatggga    12240 gggactagc tactagggcc ccactagaga aggagaggga aagggcttct cactttccct    12300
tcccaggtca cagagtgtcc gagaggcagg gaaatagaa acaggccca aggcctccag     12360 ctccacgtcc acctctaaca tggtcccctc cacaggattc cacctcaaca accagctcta   12420
tgacatcatt accatgcggt acgcagacaa acacatgaac atcgactttg acagtttcat   12480
ctgctgcttc gttaggctgg agggcatgtt cagtaagtgg gagaggggggg ctgccctctg   12540 ctctcttgca ggggcagttg tggcaacagg catctcacct gataatctcc agtctgctcc   12600
atccaggctg aacaagggcc aatgacctct ttaggcccag aatgggatgg caaagggagg   12660
gttactggtg attctctgcc tgcacatctt tgtgctgatg agggacagca ctgggcacac   12720
ggtcctctga ggggaagtta cagtagtaga ggcggagtgc gcctgtaact ggcctctggc    12780
```

-continued

```
ctgtgcattc tttcacagga gcttctcatg catttgacaa ggatggagat ggtatcatca    12840
agctcaacgt tctggaggta agcataggc acagcacatt cccctacac attaaaactc      12900 aaggtggagg ggtcaacggg gcggactgga cccagggtgt gctcctcatt tccacacagt    12960
ggtggaggga agggatagga acagaacatg gagggaggct cagcaggctc ccaggacaca    13020
tgcacttgag gccaaaaagg acctctgctc ccccagtcac ttgatgcggg aaaacatgca    13080
ccttcttagg gaagatctag gagaaaggaa acagtaagcc actgcttctt ggaaaatctt    13140 ctggggtct gacctgctgg gactgttccc tttcctcttg ccccgtaaga ttcctagggc       13200
gggggggggg ggggtcact cttttctgat ctacattctg atcttgggac ttctttcagt      13260
ggctgcagct caccatgtat gcctgaacca ggctggcctc atccaaagcc atgcaggatc    13320
actcaggatt tcagtttcac cctctatttc caaagccatt tacctcaaag gacccagcag    13380
ctacacccct acaggcttcc aggcacctca tcagtcatgt tcctcctcca ttttaccccc    13440
tacccatcct tgatcggtca tgcctagcct gacccttag taaagcaatg aggtaggaag      13500
aacaaaccct tgtcccttg ccatgtggag gaaagtgcct gcctctggtc cgagccgcct       13560
cggttctgaa gcgagtgctc ctgcttacct tgctctaggc tgtctgcaga agcacctgcc    13620
ggtggcactc agcacctcct tgtgctagag ccctccatca ccttcacgct gtcccaccat    13680
gggccaggaa ccaaaccagc actgggttct actgctgtgg ggtaaactaa ctcagtggaa    13740
tagggctggt tactttgggc tgtccaactc ataagtttgg ctgcattttg aaaaaagctg    13800
atctaaataa aggcatgtgt atggctggtc cccttgtgtt ttgttgtctc acatttagat    13860
atcagccatg catgactgaa tggcttccaa tcatatactc acctatcacc tacaagagaa    13920
caatgaaaaa cacacacaaa aacaaaatct tgaattttgt aatcatgcct attgctattt    13980
cttgagcata agaatggctc agatactttc caagacataa aaggaaggca gaggaatagt    14040
tgttgctgta aaagacatca agaataaatg gggtcatgta caacgggagg ggccggttac    14100
ctgaataatg gagtggagat tgagctatcc tagctcctct gctcactaac tgacctgtcg    14160
catgaccgtg gacaaaaccc tgaacgcagc tgtttgtttg ctaaacttct ctggaccatg    14220
gcctgcggca tatctatagg catcctgtgt tttccaccca gtttccttct tcctcgctaa    14280
gccaacgtgg aaagggctgg ccgtgaatat gcagacaagg taacgaaagt aaaccgtcaa    14340
ttagtaaaag tacttcattt tcctcttgta tttgcttcat tcttgcttca caaagttacg    14400
aagtccacag ctttatacca aaatgtaaga aggctatttg cttataaaca ttttgagtca    14460
ggtgtcatct gatttcattc ttctaatcca tattcaatat taaaaaatca gaaaccaagg    14520
gtgctggagc agctctaggg catatatttc tcttaaatag gagaaagatt ttcaacagct    14580
tttcctcctt gaccccctcc tttcccaatt tatttgggtc actaccttga atttagagtg    14640
aatctgggaa atgtagtcac cagg                                            14664
```

<210> SEQ ID NO 5
<211> LENGTH: 5149
<212> TYPE: DNA
<213> ORGANISM: Homo sapiens
<220> FEATURE:
<221> NAME/KEY: misc_feature
<222> LOCATION: (1)..(5149)
<223> OTHER INFORMATION: /label= Figure 2
<220> FEATURE:
<221> NAME/KEY: misc_feature
<222> LOCATION: (1303)..(3764)
<223> OTHER INFORMATION: /note= CDS
<220> FEATURE:

```
<221> NAME/KEY: misc_feature
<222> LOCATION: (1631)
<223> OTHER INFORMATION: /note= CGA -> TGA; nCL1 mutation in one LGMD2A
      family
<220> FEATURE:
<221> NAME/KEY: misc_feature
<222> LOCATION: (1848)
<223> OTHER INFORMATION: /note= CTG -> CAG; nCL1 mutation in one LGMD2A
      family
<220> FEATURE:
<221> NAME/KEY: misc_feature
<222> LOCATION: (1853)
<223> OTHER INFORMATION: /note= CAA -> CA; nCL1 mutation in one LGMD2A
      family
<220> FEATURE:
<221> NAME/KEY: misc_feature
<222> LOCATION: (2004)
<223> OTHER INFORMATION: /note= GGG -> GAG; nCL1 mutation in one LGMD2A
      family
<220> FEATURE:
<221> NAME/KEY: misc_feature
<222> LOCATION: (2248)
<223> OTHER INFORMATION: /note= CGG ->CG; nCL1 mutation in one LGMD2A
      family
<220> FEATURE:
<221> NAME/KEY: misc_feature
<222> LOCATION: (2364)
<223> OTHER INFORMATION: /note=GTG -> GGG; nCL1 mutation in one LGMD2A
      family
<220> FEATURE:
<221> NAME/KEY: misc_feature
<222> LOCATION: (2382)
<223> OTHER INFORMATION: /note= TGG -> TAG; nCL1 mutation in one LGMD2A
      family
<220> FEATURE:
<221> NAME/KEY: misc_feature
<222> LOCATION: (2771)
<223> OTHER INFORMATION: /note= CGG -> TGG; nCL1 mutation in one LGMD2A
      family
<220> FEATURE:
<221> NAME/KEY: misc_feature
<222> LOCATION: (3018)
<223> OTHER INFORMATION: /note= GGG -> CAG; nCL1 mutation in one LGMD2A
      family
<220> FEATURE:
<221> NAME/KEY: misc_feature
<222> LOCATION: (3372)..(3373)
<223> OTHER INFORMATION: /note= deletion AC; nCL1 mutation in one LGMD2A
      family
<220> FEATURE:
<221> NAME/KEY: misc_feature
<222> LOCATION: (3533)
<223> OTHER INFORMATION: /note= AGC -> GGC; nCL1 mutation in one LGMD2A
      family
<220> FEATURE:
<221> NAME/KEY: misc_feature
<222> LOCATION: (3609)
<223> OTHER INFORMATION: /note= CGG -> CAG; nCL1 mutation in one LGMD2A
      family
<220> FEATURE:
<221> NAME/KEY: misc_feature
<222> LOCATION: (3616)..(3619)
<223> OTHER INFORMATION: /note= deletion AGAC; nCL1 mutation in one
      LGMD2A family
<220> FEATURE:
<221> NAME/KEY: misc_feature
<222> LOCATION: (3665)..(3666)
<223> OTHER INFORMATION: /note= AG -> TCATCT; nCL1 mutation in one LGMD2A
      family

<400> SEQUENCE: 5
atatcagtta gcctggtttc actatacagt acatcatttt gcttaaagtc acagcttacg      60
agaacctatc gatgatgtta agtgaggatt ttctctgctc aggtgcactt ttttttttt     120 ttaagacgga gtctctttct gtcacctggg ctggagtgca gtggcgtgat ctggttcac     180 tacaacctct ccctcctggg ttcaagcaat tcttctgtct cagcctccca agtagctggg    240
```

-continued

```
attacaggca ccccccgcca cacccggctt attttttgtat ttttagtaga gacagggttt    300
cactattgtt gtccatgctg gtctcgaact cgtgacctca tgtgatccac ccgcctcggc    360
ctcccaaagt gcagagatta gagacgtgat ccacatggcc cagcaggacc acttttttagc   420
agattcagtc ccagtgttca ttttgtggat ggggagagac aagaggtggc aaggtcaagt    480
gtgcaggtag agacagggat tttctcaaat gaggactctg ctgagtagca ttttccatgc    540
agacatttcc aatgagcgct gacccaagaa cattctaaaa aagataccaa atctaacatt    600
gaataatgtt ctgatatcct aaaattttag gactaaaaat catgttctct aaaattcaca    660
gaatattttt gtagaattca gtacctcccg ttcaccctaa ctagctttttt tgcaatattg    720
ttttccattc atttgatggc cagtagttgg gtggtctgta taactgccta ctcaataaca    780
tgtcagcagt tctcagcttc tttccagtgt tcaccttact cagatactcc cttttcattt    840
tctggcaaca ccagcacttc atggcaacag aaatgtccct agccaggttc tctctctacc    900
atgcagtctc tcttgctctc atactcacag tgtttcttca catctatttt tagttttcct    960
ggctcaagca tcttcaggcc actgaaaaca aaccctcact ctctttctct ctccctctgg   1020
catgcatgct gctggtagga gaccccaag tcaacattgc ttcagaaatc ctttagcact    1080
catttctcag gagaacttat ggcttcgaaa tcacagctcg gtttttaaga tggacataac   1140
ctgtccgacc ttctgatggg ctttcaactt tgaactggat gtggacactt ttctctcaga   1200
tgacagaatt actccaactt cccctttgca gttgcttcct ttccttgaag gtagctgtat   1260
cttatttttct ttaaaaagct ttttcttcca aagcccacttg ccatgccgac cgtcattagc  1320
gcatctgtgg ctccaaggac agcggctgag ccccggtccc cagggccagt tcctcacccg   1380
gcccagagca aggccactga ggctgggggt ggaaacccaa gtggcatcta ttcagccatc   1440
atcagccgca attttcctat tatcggagtg aaagagaaga cattcgagca acttcacaag   1500
aaatgtctag aaaagaaagt tctttatgtg gaccctgagt tcccaccgga tgagacctct   1560
ctctttttata gccagaagtt ccccatccag ttcgtctgga agagacctcc ggaaatttgc   1620
gagaatcccc gatttatcat tgatggagcc aacagaactg acatctgtca aggagagcta   1680
ggggactgct ggtttctcgc agccattgcc tgcctgaccc tgaaccagca ccttcttttc   1740
cgagtcatac cccatgatca aagtttcatc gaaaactacg cagggatctt ccacttccag   1800
ttctggcgct atggagagtg ggtggacgtg gttatagatg actgcctgcc aacgtacaac   1860
aatcaactgg ttttcaccaa gtccaaccac cgcaatgagt tctggagtgc tctgctggag   1920
aaggcttatg ctaagctcca tggttcctac gaagctctga aggtgggaa caccacagag    1980
gccatggagg acttcacagg agggtggca gagttttttg agatcaggga tgctcctagt   2040
gacatgtaca agatcatgaa gaaagccatc gagagaggct ccctcatggg ctgctccatt   2100
gatgatggca cgaacatgac ctatggaacc tctccttctg gtctgaacat ggggagttg    2160
attgcacgga tggtaaggaa tatggataac tcactgctcc aggactcaga cctcgaccc    2220
agaggctcag atgaaagacc gacccggaca atcattccgg ttcagtatga acaagaatg    2280
gcctgcgggc tggtcagagg tcacgcctac tctgtcacgg ggctggatga ggtcccgttc   2340
aaaggtgaga aagtgaagct ggtgcggctg cggaatccgt ggggccaggt ggagtggaac   2400
ggttcttgga gtgatagatg gaaggactgg agctttgtgg acaaagatga aaggcccgt    2460
ctgcagcacc aggtcactga ggatggagag ttctggatgt cctatgagga tttcatctac   2520
catttcacaa agttggagat ctgcaacctc acggccgatg ctctgcagtc tgacaagctt   2580
```

```
cagacctgga cagtgtctgt gaacgagggc cgctgggtac ggggttgctc tgccggaggc    2640
tgccgcaact tcccagatac tttctggacc aaccctcagt accgtctgaa gctcctggag    2700
gaggacgatg accctgatga ctcggaggtg atttgcagct tcctggtggc cctgatgcag    2760
aagaaccggc ggaaggaccg gaagctaggg gccagtctct tcaccattgg cttcgccatc    2820
tacgaggttc ccaaagagat gcacgggaac aagcagcacc tgcagaagga cttcttcctg    2880
tacaacgcct ccaaggccag gagcaaaacc tacatcaaca tgcgggaggt gtcccagcgc    2940
ttccgcctgc ctcccagcga gtacgtcatc gtgccctcca cctacgagcc ccaccaggag    3000
ggggaattca tcctccgggt cttctctgaa agaggaacc tctctgagga agttgaaaat    3060
accatctccg tggatcggcc agtgaaaaag aaaaaaacca agcccatcat cttcgtttcg    3120
gacagagcaa acagcaacaa ggagctgggt gtggaccagg agtcagagga gggcaaaggc    3180
aaaacaagcc ctgataagca aaagcagtcc ccacagccac agcctggcag ctctgatcag    3240
gaaagtgagg aacagcaaca attccggaac attttcaagc agatagcagg agatgacatg    3300
gagatctgtg cagatgagct caagaaggtc cttaacacag tcgtgaacaa acacaaggac    3360
ctgaagacac acgggttcac actggagtcc tgccgtagca tgattgcgct catggataca    3420
gatggctctg gaaagctcaa cctgcaggag ttccaccacc tctggaacaa gattaaggcc    3480
tggcagaaaa ttttcaaaca ctatgacaca gaccagtccg gcaccatcaa cagctacgag    3540
atgcgaaatg cagtcaacga cgcaggattc cacctcaaca accagctcta tgacatcatt    3600
accatgcggt acgcagacaa acacatgaac atcgactttg acagtttcat ctgctgcttc    3660
gttaggctgg agggcatgtt cagagctttt catgcatttg acaaggatgg agatggtatc    3720
atcaagctca acgttctgga gtggctgcag ctcaccatgt atgcctgaac caggctggcc    3780
tcatccaaag ccatgcagga tcactcagga tttcagtttc accctctatt tccaaagcca    3840
tttacctcaa aggacccagc agctacaccc tacaggctt ccaggcacct catcagtcat    3900
gttcctcctc catttacc cctacccatc cttgatcggt catgcctagc ctgacccttt    3960
agtaaagcaa tgaggtagga agaacaaacc cttgtccctt tgccatgtgg aggaaagtgc    4020
ctgcctctgg tccgagccgc ctcggttctg aagcgagtgc tcctgcttac cttgctctag    4080
gctgtctgca gaagcacctg ccggtggcac tcagcacctc cttgtgctag agccctccat    4140
caccttcacg ctgtcccacc atgggccagg aaccaaacca gcactgggtt ctactgctgt    4200
ggggtaaact aactcagtgg aatagggctg gttactttgg gctgtccaac tcataagttt    4260
ggctgcattt tgaaaaagc tgatctaaat aaaggcatgt gtatggctgg tccccttgtg    4320
ttttgttgtc tcacatttag atatcagcca tgcatgactg aatggcttcc aatcatatac    4380
tcacctatca cctacaagag aacaatgaaa aacacacaca aaaacaaaat cttgaatttt    4440
gtaatcatgc ctattgctat ttcttgagca taagaatggc tcagatactt tccaagacat    4500
aaaaggaagg cagaggaata gttgttgctg taaaagacat caagaataaa tgggtcatgt    4560
acaacgggag gggccggtta cctgaataat ggagtggaga ttgagctatc ctagctcctc    4620
tgctcactaa ctgacctgtc gcatgaccgt ggacaaaacc ctgaacgcag ctgtttgttt    4680
gctaaacttc tctggaccat ggcctgcggc atatctatag gcatcctgtg ttttccaccc    4740
agtttccttc ttcctcgcta agccaacgtg gaaagggctg gccgtgaata tgcagacaag    4800
gtaacgaaag taaaccgtca attagtaaaa gtacttcatt ttcctcttgt atttgcttca    4860
tatcttgctt cacaaagtta cgaagttcac agctttatac caaaatgtaa gaaggctatt    4920
tgcttataaa cattttttgca gtcaggtgtc atctgatttc attcttctaa tccatattca    4980
```

-continued

```
atattanaaa aatcagaaac caagggtgct ggagcagctc tagggcatat atttctctta    5040
aataggagaa agattttcaa cagcttttcc tccttgaccc cctcctttcc caatttattt    5100
gggtcactac cttgaattta gagtgaatct gggaaatgta gtcaccagg                5149
```

```
<210> SEQ ID NO 6
<211> LENGTH: 821
<212> TYPE: PRT
<213> ORGANISM: Homo sapiens
<220> FEATURE:
<221> NAME/KEY: DOMAIN
<222> LOCATION: (1)..(821)
<223> OTHER INFORMATION: /label= "Figure 2"
<220> FEATURE:
<221> NAME/KEY: DOMAIN
<222> LOCATION: (1)..(61)
<223> OTHER INFORMATION: /label= ALU
      /note= "FIGURE 3-HUMAN"
<220> FEATURE:
<221> NAME/KEY: DOMAIN
<222> LOCATION: (268)..(309)
<223> OTHER INFORMATION: /label= ALU
      /note= "FIGURE 3-HUMAN"
<220> FEATURE:
<221> NAME/KEY: DOMAIN
<222> LOCATION: (310)..(328)
<223> OTHER INFORMATION: /label= ALU
      /note= "FIGURE 3-HUMAN"
<220> FEATURE:
<221> NAME/KEY: DOMAIN
<222> LOCATION: (1)..(821)
<223> OTHER INFORMATION: /label= "Figure 2"
<220> FEATURE:
<221> NAME/KEY: DOMAIN
<222> LOCATION: (619)..(653)
<223> OTHER INFORMATION: /label= ALU
      /note= "FIGURE 3-HUMAN"

<400> SEQUENCE: 6

Met Pro Thr Val Ile Ser Ala Ser Val Ala Pro Arg Thr Ala Ala Glu
  1               5                  10                  15

Pro Arg Ser Pro Gly Pro Val Pro His Pro Ala Gln Ser Lys Ala Thr
             20                  25                  30

Glu Ala Gly Gly Gly Asn Pro Ser Gly Ile Tyr Ser Ala Ile Ile Ser
         35                  40                  45

Arg Asn Phe Pro Ile Ile Gly Val Lys Glu Lys Thr Phe Glu Gln Leu
     50                  55                  60

His Lys Lys Cys Leu Glu Lys Lys Val Leu Tyr Val Asp Pro Glu Phe
 65                  70                  75                  80

Pro Pro Asp Glu Thr Ser Leu Phe Tyr Ser Gln Lys Phe Pro Ile Gln
                 85                  90                  95

Phe Val Trp Lys Arg Pro Pro Glu Ile Cys Glu Asn Pro Arg Phe Ile
            100                 105                 110

Ile Asp Gly Ala Asn Arg Thr Asp Ile Cys Gln Gly Glu Leu Gly Asp
        115                 120                 125

Cys Trp Phe Leu Ala Ala Ile Ala Cys Leu Thr Leu Asn Gln His Leu
    130                 135                 140

Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
                165                 170                 175

Val Ile Asp Asp Cys Leu Pro Thr Tyr Asn Asn Gln Leu Val Phe Thr
            180                 185                 190
```

-continued

```
Lys Ser Asn His Arg Asn Glu Phe Trp Ser Ala Leu Leu Glu Lys Ala
        195                 200                 205

Tyr Ala Lys Leu His Gly Ser Tyr Glu Ala Leu Lys Gly Gly Asn Thr
    210                 215                 220

Thr Glu Ala Met Glu Asp Phe Thr Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
            260                 265                 270

Thr Tyr Gly Thr Ser Pro Ser Gly Leu Asn Met Gly Glu Leu Ile Ala
        275                 280                 285

Arg Met Val Arg Asn Met Asp Asn Ser Leu Leu Gln Asp Ser Asp Leu
    290                 295                 300

Asp Pro Arg Gly Ser Asp Glu Arg Pro Thr Arg Thr Ile Ile Pro Val
305                 310                 315                 320

Gln Tyr Glu Thr Arg Met Ala Cys Gly Leu Val Arg Gly His Ala Tyr
                325                 330                 335

Ser Val Thr Gly Leu Asp Glu Val Pro Phe Lys Gly Glu Lys Val Lys
            340                 345                 350

Leu Val Arg Leu Arg Asn Pro Trp Gly Gln Val Glu Trp Asn Gly Ser
        355                 360                 365

Trp Ser Asp Arg Trp Lys Asp Trp Ser Phe Val Asp Lys Asp Glu Lys
    370                 375                 380

Ala Arg Leu Gln His Gln Val Thr Glu Asp Gly Glu Phe Trp Met Ser
385                 390                 395                 400

Tyr Glu Asp Phe Ile Tyr His Phe Thr Lys Leu Glu Ile Cys Asn Leu
                405                 410                 415

Thr Ala Asp Ala Leu Gln Ser Asp Lys Leu Gln Thr Trp Thr Val Ser
            420                 425                 430

Val Asn Glu Gly Arg Trp Val Arg Gly Cys Ser Ala Gly Gly Cys Arg
        435                 440                 445

Asn Phe Pro Asp Thr Phe Trp Thr Asn Pro Gln Tyr Arg Leu Lys Leu
    450                 455                 460

Leu Glu Glu Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Ser Leu Phe Thr Ile Gly Phe Ala Ile Tyr Glu Val Pro Lys Glu
            500                 505                 510

Met His Gly Asn Lys Gln His Leu Gln Lys Asp Phe Phe Leu Tyr Asn
        515                 520                 525

Ala Ser Lys Ala Arg Ser Lys Thr Tyr Ile Asn Met Arg Glu Val Ser
    530                 535                 540

Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                565                 570                 575

Lys Arg Asn Leu Ser Glu Glu Val Glu Asn Thr Ile Ser Val Asp Arg
            580                 585                 590

Pro Val Lys Lys Lys Thr Lys Pro Ile Ile Phe Val Ser Asp Arg
        595                 600                 605

Ala Asn Ser Asn Lys Glu Leu Gly Val Asp Gln Glu Ser Glu Glu Gly
```

-continued

```
            610                 615                 620
Lys Gly Lys Thr Ser Pro Asp Lys Gln Lys Gln Ser Pro Gln Pro Gln
625                 630                 635                 640

Pro Gly Ser Ser Asp Gln Glu Ser Glu Glu Gln Gln Gln Phe Arg Asn
                645                 650                 655

Ile Phe Lys Gln Ile Ala Gly Asp Asp Met Glu Ile Cys Ala Asp Glu
                660                 665                 670

Leu Lys Lys Val Leu Asn Thr Val Asn Lys His Lys Asp Leu Lys
                675                 680                 685

Thr His Gly Phe Thr Leu Glu Ser Cys Arg Ser Met Ile Ala Leu Met
            690                 695                 700

Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
                725                 730                 735

Asp Gln Ser Gly Thr Ile Asn Ser Tyr Glu Met Arg Asn Ala Val Asn
                740                 745                 750

Asp Ala Gly Phe His Leu Asn Asn Gln Leu Tyr Asp Ile Ile Thr Met
                755                 760                 765

Arg Tyr Ala Asp Lys His Met Asn Ile Asp Phe Asp Ser Phe Ile Cys
770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
            820

<210> SEQ ID NO 7
<211> LENGTH: 821
<212> TYPE: PRT
<213> ORGANISM: Homo sapiens
<220> FEATURE:
<221> NAME/KEY: DOMAIN
<222> LOCATION: (1)..(61)
<223> OTHER INFORMATION: /label= ALU
<220> FEATURE:
<221> NAME/KEY: DOMAIN
<222> LOCATION: (268)..(309)
<223> OTHER INFORMATION: /label= ALU
      /note= "FIGURE 3 - RAT"
<220> FEATURE:
<221> NAME/KEY: DOMAIN
<222> LOCATION: (310)..(328)
<223> OTHER INFORMATION: /label= ALU
      /note= "FIGURE 3 - RAT"
<220> FEATURE:
<221> NAME/KEY: DOMAIN
<222> LOCATION: (578)..(618)
<223> OTHER INFORMATION: /label= ALU
      /note= "FIGURE 3 - RAT"
<220> FEATURE:
<221> NAME/KEY: DOMAIN
<222> LOCATION: (619)..(653)
<223> OTHER INFORMATION: /label= ALU
      /note= "FIGURE 3 - RAT"

<400> SEQUENCE: 7

Met Pro Thr Val Ile Ser Pro Thr Val Ala Pro Arg Thr Gly Ala Glu
1               5                   10                  15

Pro Arg Ser Pro Gly Pro Val Pro His Pro Ala Gln Gly Lys Thr Thr
                20                  25                  30
```

-continued

```
Glu Ala Gly Gly Gly His Pro Gly Ile Tyr Ser Ala Ile Ile Ser
         35                  40                  45
Arg Asn Phe Pro Ile Ile Gly Val Lys Glu Lys Thr Phe Glu Gln Leu
         50                  55                  60
His Lys Lys Cys Leu Glu Lys Lys Val Leu Tyr Leu Asp Pro Glu Phe
 65                  70                  75                  80
Pro Pro Asp Glu Thr Ser Leu Phe Tyr Ser Gln Lys Phe Pro Ile Gln
                 85                  90                  95
Phe Val Trp Lys Arg Pro Pro Glu Ile Cys Glu Asn Pro Arg Phe Ile
                100                 105                 110
Ile Gly Gly Ala Asn Arg Thr Asp Ile Cys Gln Gly Asp Leu Gly Asp
             115                 120                 125
Cys Trp Leu Leu Ala Ala Ile Ala Cys Leu Thr Leu Asn Glu Arg Leu
         130                 135                 140
Leu Phe Arg Val Ile Pro His Asp Gln Ser Phe Thr Glu Asn Tyr Ala
145                 150                 155                 160
Gly Ile Phe His Phe Gln Phe Trp Arg Tyr Gly Asp Trp Val Asp Val
                 165                 170                 175
Val Ile Asp Asp Cys Leu Pro Thr Tyr Asn Asn Gln Leu Val Phe Thr
             180                 185                 190
Lys Ser Asn His Arg Asn Glu Phe Trp Ser Ala Leu Leu Glu Lys Ala
         195                 200                 205
Tyr Ala Lys Leu His Gly Ser Tyr Glu Ala Leu Lys Gly Gly Asn Thr
         210                 215                 220
Thr Glu Ala Met Glu Asp Phe Thr Gly Gly Val Thr Glu Phe Phe Glu
225                 230                 235                 240
Ile Lys Asp Ala Pro Ser Asp Met Tyr Lys Ile Met Arg Lys Ala Ile
                 245                 250                 255
Glu Arg Gly Ser Leu Met Gly Cys Ser Ile Asp Asp Gly Thr Asn Met
             260                 265                 270
Thr Tyr Gly Thr Ser Pro Ser Gly Leu Asn Met Gly Glu Leu Ile Ala
         275                 280                 285
Arg Met Val Arg Asn Met Asp Asn Ser Leu Leu Arg Asp Ser Asp Leu
         290                 295                 300
Asp Pro Arg Ala Ser Asp Asp Arg Pro Ser Arg Thr Ile Val Pro Val
305                 310                 315                 320
Gln Tyr Glu Thr Arg Met Ala Cys Gly Leu Val Arg Gly His Ala Tyr
                 325                 330                 335
Ser Val Thr Gly Leu Glu Glu Ala Leu Phe Lys Gly Glu Lys Val Lys
             340                 345                 350
Leu Val Arg Leu Arg Asn Pro Trp Gly Gln Val Glu Trp Asn Gly Ser
         355                 360                 365
Trp Ser Asp Gly Trp Lys Asp Trp Ser Phe Val Asp Lys Asp Glu Lys
         370                 375                 380
Ala Arg Leu Gln His Gln Val Thr Glu Asp Gly Glu Phe Trp Met Ser
385                 390                 395                 400
Tyr Asp Asp Phe Val Tyr His Phe Thr Lys Leu Glu Ile Cys Asn Leu
                 405                 410                 415
Thr Ala Asp Ala Leu Glu Ser Asp Lys Leu Gln Thr Trp Thr Val Ser
             420                 425                 430
Val Asn Glu Gly Arg Trp Val Arg Gly Cys Ser Ala Gly Gly Cys Arg
         435                 440                 445
Asn Phe Pro Asp Thr Phe Trp Thr Asn Pro Gln Tyr Arg Leu Lys Leu
```

```
                450                 455                 460
Leu Glu Glu Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Asn Leu Phe Thr Ile Gly Phe Ala Ile Tyr Glu Val Pro Lys Glu
                500                 505                 510

Met His Gly Asn Lys Gln His Leu Gln Lys Asp Phe Phe Leu Tyr Asn
                515                 520                 525

Ala Ser Lys Ala Arg Ser Lys Thr Tyr Ile Asn Met Arg Glu Val Ser
530                 535                 540

Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                565                 570                 575

Lys Arg Asn Leu Ser Glu Glu Ala Glu Asn Thr Ile Ser Val Asp Arg
                580                 585                 590

Pro Val Lys Lys Lys Asn Lys Pro Ile Ile Phe Val Ser Asp Arg
                595                 600                 605

Ala Asn Ser Asn Lys Glu Leu Gly Val Asp Gln Glu Ala Glu Glu Gly
                610                 615                 620

Lys Asp Lys Thr Gly Pro Asp Lys Gln Gly Glu Ser Pro Gln Pro Arg
625                 630                 635                 640

Pro Gly His Thr Asp Gln Glu Ser Glu Gln Gln Phe Arg Asn
                645                 650                 655

Ile Phe Arg Gln Ile Ala Gly Asp Asp Met Glu Ile Cys Ala Asp Glu
                660                 665                 670

Leu Lys Asn Val Leu Asn Thr Val Asn Lys His Lys Asp Leu Lys
                675                 680                 685

Thr Gln Gly Phe Thr Leu Glu Ser Cys Arg Ser Met Ile Ala Leu Met
                690                 695                 700

Asp Thr Asp Gly Ser Gly Arg Leu Asn Leu Gln Glu Phe His His Leu
705                 710                 715                 720

Trp Lys Lys Ile Lys Ala Trp Gln Lys Ile Phe Lys His Tyr Asp Thr
                725                 730                 735

Asp His Ser Gly Thr Ile Asn Ser Tyr Glu Met Arg Asn Ala Val Asn
                740                 745                 750

Asp Ala Gly Phe His Leu Asn Ser Gln Leu Tyr Asp Ile Ile Thr Met
                755                 760                 765

Arg Tyr Ala Asp Lys His Met Asn Ile Asp Phe Asp Ser Phe Ile Cys
770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
                820

<210> SEQ ID NO 8
<211> LENGTH: 821
<212> TYPE: PRT
<213> ORGANISM: Homo sapiens
<220> FEATURE:
<221> NAME/KEY: DOMAIN
<222> LOCATION: (1)..(61)
```

```
<223> OTHER INFORMATION: /label= ALU
      /note= "FIGURE 3 -PIG"
<220> FEATURE:
<221> NAME/KEY: DOMAIN
<222> LOCATION: (268)..(309)
<223> OTHER INFORMATION: /label= ALU
      /note= "FIGURE 3 -PIG"
<220> FEATURE:
<221> NAME/KEY: DOMAIN
<222> LOCATION: (310)..(328)
<223> OTHER INFORMATION: /label= ALU
      /note= "FIGURE 3 -PIG"
<220> FEATURE:
<221> NAME/KEY: DOMAIN
<222> LOCATION: (578)..(618)
<223> OTHER INFORMATION: /label= ALU
      /note= "FIGURE 3 -PIG"
<220> FEATURE:
<221> NAME/KEY: DOMAIN
<222> LOCATION: (619)..(653)
<223> OTHER INFORMATION: /label= ALU
      /note= "FIGURE 3 -PIG"

<400> SEQUENCE: 8

Met Pro Thr Val Ile Ser Ala Ser Val Ala Pro Arg Thr Ala Ala Glu
 1               5                  10                  15

Pro Arg Ser Pro Gly Pro Val Pro His Pro Ala Gln Ser Lys Ala Thr
            20                  25                  30

Glu Ala Gly Gly Gly Asn Pro Ser Gly Ile Tyr Ser Ala Ile Ile Ser
        35                  40                  45

Arg Asn Phe Pro Ile Ile Gly Val Lys Glu Lys Thr Phe Glu Gln Leu
    50                  55                  60

His Lys Lys Cys Leu Glu Lys Lys Val Leu Tyr Val Asp Pro Glu Phe
65                  70                  75                  80

Pro Pro Asp Glu Thr Ser Leu Phe Tyr Ser Gln Lys Phe Pro Ile Gln
                85                  90                  95

Phe Val Trp Lys Arg Pro Pro Glu Ile Cys Glu Asn Pro Arg Phe Ile
            100                 105                 110

Ile Asp Gly Ala Asn Arg Thr Asp Ile Cys Gln Gly Glu Leu Gly Asp
        115                 120                 125

Cys Trp Phe Leu Ala Ala Ile Ala Cys Leu Thr Leu Asn Gln His Leu
    130                 135                 140

Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
                165                 170                 175

Val Ile Asp Asp Cys Leu Pro Thr Tyr Asn Asn Gln Leu Val Phe Thr
            180                 185                 190

Lys Ser Asn His Arg Asn Glu Phe Trp Ser Ala Leu Leu Glu Lys Ala
        195                 200                 205

Tyr Ala Lys Leu His Gly Ser Tyr Glu Ala Leu Lys Gly Gly Asn Thr
    210                 215                 220

Thr Glu Ala Met Glu Asp Phe Thr Gly Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
            260                 265                 270

Thr Tyr Gly Thr Ser Pro Ser Gly Leu Asn Met Gly Asp Leu Ile Ala
        275                 280                 285
```

-continued

```
Arg Met Val Arg Asn Met Glu Asn Ser Arg Leu Arg Asp Ser Ile Leu
    290                 295                 300
Asp Pro Glu Val Ser Asp Asp Arg Pro Thr Arg Thr Ile Val Pro Val
305                 310                 315                 320
Gln Phe Glu Thr Arg Met Ala Cys Gly Leu Val Arg Gly His Ala Tyr
                    325                 330                 335
Ser Val Thr Gly Leu Glu Glu Ala Leu Phe Lys Gly Glu Lys Val Lys
            340                 345                 350
Leu Val Arg Leu Arg Asn Pro Trp Gly Gln Val Glu Trp Asn Gly Ser
        355                 360                 365
Trp Ser Asp Ser Trp Lys Asp Trp Ser Phe Val Asp Lys Asp Glu Lys
370                 375                 380
Ala Arg Leu Gln His Gln Val Thr Glu Asp Gly Glu Phe Trp Met Ser
385                 390                 395                 400
Tyr Asp Asp Phe Ile Tyr His Phe Thr Lys Leu Glu Ile Cys Asn Leu
                    405                 410                 415
Thr Ala Asp Ala Leu Glu Ser Asp Lys Leu Gln Thr Trp Thr Val Ser
                420                 425                 430
Val Asn Glu Gly Arg Trp Val Arg Gly Cys Ser Ala Gly Thr Gly Arg
            435                 440                 445
Asn Phe Pro Asp Thr Phe Trp Thr Asn Pro Gln Tyr Arg Leu Lys Leu
        450                 455                 460
Leu Glu Glu Asp Asp Asp Pro Asp Asp Ser Glu Val Ile Cys Ser Phe
465                 470                 475                 480
Leu Val Ala Leu Met Gln Arg Asn Arg Arg Lys Asp Arg Lys Leu Gly
                    485                 490                 495
Ala Asn Leu Phe Thr Ile Gly Phe Ala Ile Tyr Glu Val Pro Lys Glu
                500                 505                 510
Met His Gly Asn Lys Gln His Leu Gln Lys Asp Phe Phe Leu Tyr Asn
            515                 520                 525
Ala Ser Lys Ala Arg Ser Arg Thr Tyr Ile Asn Met Arg Glu Val Ser
        530                 535                 540
Glu Arg Phe Arg Leu Pro Pro Ser Glu Tyr Val Ile Val Pro Ser Thr
545                 550                 555                 560
Tyr Glu Pro His Gln Glu Gly Glu Phe Met Leu Arg Val Phe Ser Glu
                    565                 570                 575
Lys Arg Lys Leu Ser Glu Glu Val Glu Asn Thr Ile Ser Val Asp Arg
                580                 585                 590
Pro Val Arg Lys Lys Thr Lys Pro Ile Ile Phe Val Ser Asp Arg
            595                 600                 605
Ala Asn Ser Asn Lys Glu Leu Gly Val Asp Gln Glu Ser Glu Glu Gly
        610                 615                 620
Gln Asp Lys Thr Ser Pro Asp Lys Gln Glu Lys Ser Pro Lys Pro Glu
625                 630                 635                 640
Pro Ser Asn Thr Asp Gln Glu Ser Glu Glu Gln Gln Phe Arg Asn
                    645                 650                 655
Ile Phe Lys Gln Ile Ala Gly Asp Asp Met Glu Ile Cys Ala Asp Glu
                660                 665                 670
Leu Lys Lys Val Leu Asn Thr Val Val Asn Lys His Lys Asp Leu Lys
            675                 680                 685
Thr His Gly Phe Thr Leu Glu Ser Cys Arg Ser Met Ile Ala Leu Met
        690                 695                 700
Asp Thr Asp Gly Ser Gly Lys Leu Asn Leu Gln Glu Phe His His Leu
```

-continued

```
                705                 710                 715                 720
Trp Asn Lys Ile Lys Ala Trp Gln Lys Ile Phe Lys His Tyr Asp Thr
                725                 730                 735
Asp Gln Ser Gly Thr Ile Asn Ser Tyr Glu Met Arg Asn Ala Val Asn
            740                 745                 750
Asp Ala Gly Phe His Leu Asn Asn Gln Leu Tyr Asp Ile Ile Thr Met
            755                 760                 765
Arg Tyr Ala Asp Lys His Met Asn Ile Asp Phe Asp Ser Phe Ile Cys
        770                 775                 780
Cys Phe Val Arg Leu Glu Gly Met Phe Arg Ala Phe His Ala Phe Asp
785                 790                 795                 800
Lys Asp Gly Asp Gly Ile Ile Lys Leu Asn Val Leu Glu Trp Leu Gln
            805                 810                 815
Leu Thr Met Tyr Ala
            820

<210> SEQ ID NO 9
<211> LENGTH: 821
<212> TYPE: PRT
<213> ORGANISM: Homo sapiens
<220> FEATURE:
<221> NAME/KEY: DOMAIN
<222> LOCATION: (1)..(61)
<223> OTHER INFORMATION: /label= ALU
      /note= "FIGURE 3 -COW"
<220> FEATURE:
<221> NAME/KEY: DOMAIN
<222> LOCATION: (268)..(309)
<223> OTHER INFORMATION: /label= ALU
      /note= "FIGURE 3 -COW"
<220> FEATURE:
<221> NAME/KEY: DOMAIN
<222> LOCATION: (310)..(328)
<223> OTHER INFORMATION: /label= ALU
      /note= "FIGURE 3 -COW"
<220> FEATURE:
<221> NAME/KEY: DOMAIN
<222> LOCATION: (578)..(618)
<223> OTHER INFORMATION: /label= ALU
      /note= "FIGURE 3 -COW"
<220> FEATURE:
<221> NAME/KEY: DOMAIN
<222> LOCATION: (619)..(653)
<223> OTHER INFORMATION: /label= ALU
      /note= "FIGURE 3 -COW"

<400> SEQUENCE: 9

Met Pro Thr Val Ile Ser Ala Ser Val Ala Pro Arg Thr Ala Ala Glu
  1               5                  10                  15
Pro Arg Ser Pro Gly Pro Val Pro His Pro Ala Gln Ser Lys Ala Thr
                20                  25                  30
Glu Ala Gly Gly Gly Asn Pro Ser Gly Ile Tyr Ser Ala Ile Ile Ser
            35                  40                  45
Arg Asn Phe Pro Ile Ile Gly Val Lys Glu Lys Thr Phe Glu Gln Leu
    50                  55                  60
His Lys Lys Cys Leu Glu Lys Lys Val Leu Tyr Val Asp Pro Glu Phe
65                  70                  75                  80
Pro Pro Asp Glu Thr Ser Leu Phe Tyr Ser Gln Lys Phe Pro Ile Gln
                85                  90                  95
Phe Val Trp Lys Arg Pro Pro Glu Ile Cys Glu Asn Pro Arg Phe Ile
                100                 105                 110
Ile Asp Gly Ala Asn Arg Thr Asp Ile Cys Gln Gly Glu Leu Gly Asp
            115                 120                 125
```

-continued

Cys Trp Phe Leu Ala Ala Ile Ala Cys Leu Thr Leu Asn Gln His Leu
    130                 135                 140

Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
                165                 170                 175

Val Ile Asp Asp Cys Leu Pro Thr Tyr Asn Asn Gln Leu Val Phe Thr
            180                 185                 190

Lys Ser Asn His Arg Asn Glu Phe Trp Ser Ala Leu Leu Glu Lys Ala
        195                 200                 205

Tyr Ala Lys Leu His Gly Ser Tyr Glu Ala Leu Lys Gly Asn Thr
    210                 215                 220

Thr Glu Ala Met Glu Asp Phe Thr Gly Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
            260                 265                 270

Thr Tyr Gly Thr Ser Pro Ser Gly Leu Asn Met Gly Glu Leu Ile Glu
        275                 280                 285

Arg Met Val Arg Asn Met Asp Asn Ser Arg Leu Arg Asp Ser Ile Leu
    290                 295                 300

Asp Pro Glu Val Ser Asp Asp Arg Pro Thr Arg Met Ile Val Pro Val
305                 310                 315                 320

Gln Phe Glu Thr Arg Met Ala Cys Gly Leu Val Arg Gly His Ala Tyr
                325                 330                 335

Ser Val Thr Gly Leu Glu Glu Ala Leu Tyr Lys Gly Glu Lys Val Lys
            340                 345                 350

Leu Val Arg Leu Arg Asn Pro Trp Gly Gln Val Glu Trp Asn Gly Ser
        355                 360                 365

Trp Ser Asp Ser Trp Lys Asp Trp Ser Tyr Val Asp Lys Asp Glu Lys
    370                 375                 380

Ala Arg Leu Gln His Gln Val Thr Glu Asp Gly Glu Phe Trp Met Ser
385                 390                 395                 400

Tyr Glu Asp Phe Ile Tyr His Phe Thr Lys Leu Glu Ile Cys Asn Leu
                405                 410                 415

Thr Ala Asp Ala Leu Gln Ser Asp Lys Leu Gln Thr Trp Thr Val Ser
            420                 425                 430

Val Asn Glu Gly Arg Trp Val Arg Gly Cys Ser Ala Gly Gly Cys Arg
        435                 440                 445

Asn Phe Pro Asp Thr Phe Trp Thr Asn Pro Gln Tyr Arg Leu Lys Leu
    450                 455                 460

Leu Glu Glu Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Ser Leu Phe Thr Ile Gly Phe Ala Ile Tyr Glu Val Pro Lys Glu
            500                 505                 510

Met His Gly Asn Lys Gln His Leu Gln Lys Asp Phe Phe Leu Tyr Asn
        515                 520                 525

Ala Ser Lys Ala Arg Ser Lys Thr Tyr Ile Asn Met Arg Glu Val Ser
    530                 535                 540

-continued

```
Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                565                 570                 575

Lys Arg Asn Leu Ser Glu Val Glu Asn Thr Ile Ser Val Asp Arg
            580                 585                 590

Pro Val Lys Lys Lys Thr Lys Pro Ile Ile Phe Val Ser Asp Arg
        595                 600                 605

Ala Asn Ser Asn Lys Glu Leu Gly Val Asp Gln Glu Ser Glu Glu Gly
    610                 615                 620

Lys Gly Lys Thr Ser Pro Asp Lys Gln Lys Gln Ser Pro Gln Pro Gln
625                 630                 635                 640

Pro Gly Ser Ser Asp Gln Glu Ser Glu Gln Gln Gln Phe Arg Asn
                645                 650                 655

Ile Phe Lys Gln Ile Ala Gly Asp Asp Met Glu Ile Cys Ala Asp Glu
                660                 665                 670

Leu Lys Lys Val Leu Asn Thr Val Asn Lys His Lys Asp Leu Lys
            675                 680                 685

Thr His Gly Phe Thr Leu Glu Ser Cys Arg Ser Met Ile Ala Leu Met
690                 695                 700

Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
                725                 730                 735

Asp Gln Ser Gly Thr Ile Asn Ser Tyr Glu Met Arg Asn Ala Val Asn
                740                 745                 750

Asp Ala Gly Phe His Leu Asn Asn Gln Leu Tyr Asp Ile Ile Thr Met
            755                 760                 765

Arg Tyr Ala Asp Lys His Met Asn Ile Asp Phe Asp Ser Phe Ile Cys
770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
            820
```

<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 1

<400> SEQUENCE: 10
atggagccaa cagaactgac                    20

<210> SEQ ID NO 11
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 1

<400> SEQUENCE: 11

```
gtatgactcg gaaaagaagg t                                               21

<210> SEQ ID NO 12
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 1

<400> SEQUENCE: 12
taagcaaaag cagtccccac                                                 20

<210> SEQ ID NO 13
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 1

<400> SEQUENCE: 13
ttgctgttcc tcactttcct g                                               21

<210> SEQ ID NO 14
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 1

<400> SEQUENCE: 14
gtttcatctg ctgcttcgtt                                                 20

<210> SEQ ID NO 15
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 1

<400> SEQUENCE: 15
ctggttcagg catacatggt                                                 20

<210> SEQ ID NO 16
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 1

<400> SEQUENCE: 16
ttctttatgt ggaccctgag tt                                              22

<210> SEQ ID NO 17
<211> LENGTH: 19
<212> TYPE: DNA
<213> ORGANISM: Homo sapiens
<220> FEATURE:
```

```
<221> NAME/KEY: misc_feature
<222> LOCATION: (1)..(19)
<223> OTHER INFORMATION: /label= Table 1

<400> SEQUENCE: 17
acgaactgga tgggaact                                                    19

<210> SEQ ID NO 18
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 18
ttcagtacct cccgttcacc                                                  20

<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 19
gatgcttgag ccaggaaaac                                                  20

<210> SEQ ID NO 20
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 3

<400> SEQUENCE: 20
ctttccttga aggtagctgt at                                               22

<210> SEQ ID NO 21
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 21
gaggtgctga gtgagaggac                                                  20

<210> SEQ ID NO 22
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 3

<400> SEQUENCE: 22
actccgtctc aaaaaaatac ct                                               22
```

```
<210> SEQ ID NO 23
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 23 attgtcccctt tacctcctgg                                              20

<210> SEQ ID NO 24
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 24
tggaagtagg agagtgggca                                               20

<210> SEQ ID NO 25
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 25
gggtagatgg gtgggaagtt                                               20

<210> SEQ ID NO 26
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 26
gaggaatgtg gaggaaggac                                               20

<210> SEQ ID NO 27
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 27
ttcctgtgag tgaggtctcg                                               20

<210> SEQ ID NO 28
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3
```

-continued

```
<400> SEQUENCE: 28
ggaactctgt gaccccaaat                                              20

<210> SEQ ID NO 29
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 29
tcctcaaaca aaacattcgc                                              20

<210> SEQ ID NO 30
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 30
gttccctaca ttctccatcg                                              20

<210> SEQ ID NO 31
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 3

<400> SEQUENCE: 31
gttatttcaa cccagaccct t                                            21

<210> SEQ ID NO 32
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 3

<400> SEQUENCE: 32
aatgggttct ctggttactg c                                            21

<210> SEQ ID NO 33
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 3

<400> SEQUENCE: 33
agcacgaaaa gcaaagataa a                                            21

<210> SEQ ID NO 34
<211> LENGTH: 20
<212> TYPE: DNA
<213> ORGANISM: Homo sapiens
```

```
<220> FEATURE:
<221> NAME/KEY: misc_feature
<222> LOCATION: (1)..(20)
<223> OTHER INFORMATION: /label= Table 3

<400> SEQUENCE: 34
gtaagagatt tgcccccag                                          20

<210> SEQ ID NO 35
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 35
tctgcggatc attggttttg                                         20

<210> SEQ ID NO 36
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 36
ccttcccttc ttcctgcttc                                         20

<210> SEQ ID NO 37
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 37
ctctcttccc caccctctacc                                        20

<210> SEQ ID NO 38
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 38
cctcctcacc tgctcccata                                         20

<210> SEQ ID NO 39
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 39
tttttcggct tagaccctcc                                         20
```

```
<210> SEQ ID NO 40
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 3

<400> SEQUENCE: 40
tgtggggaat agaaataaat gg                                          22

<210> SEQ ID NO 41
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 3

<400> SEQUENCE: 41
ccaggagctc tgtgggtca                                              19

<210> SEQ ID NO 42
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 3

<400> SEQUENCE: 42
ggctcctcat cctcattcac a                                           21

<210> SEQ ID NO 43
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 43
gtggaggagg gtgagtgtgc                                             20

<210> SEQ ID NO 44
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 44
tgtggcagga caggacgttc                                             20

<210> SEQ ID NO 45
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3
```

```
<400> SEQUENCE: 45
ttcaacctct ggagtgggcc                                              20

<210> SEQ ID NO 46
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 46
caccagagca aaccgtccac                                              20

<210> SEQ ID NO 47
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 47
acagcccaga ctcccattcc                                              20

<210> SEQ ID NO 48
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 48
ttctcttctc ccttcaccct                                              20

<210> SEQ ID NO 49
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 3

<400> SEQUENCE: 49
acacacttca tgctctctac cc                                           22

<210> SEQ ID NO 50
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 50
ccgcctattc ctttcctctt                                              20

<210> SEQ ID NO 51
<211> LENGTH: 20
<212> TYPE: DNA
```

```
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 51
gacaaactcc tgggaagcct                                                 20

<210> SEQ ID NO 52
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 52
acctctgacc cctgtgaacc                                                 20

<210> SEQ ID NO 53
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 53
tgtggatttg tgtgctacgc                                                 20

<210> SEQ ID NO 54
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: /label= Table 3

<400> SEQUENCE: 54
cataaatagc accgacaggg a                                               21

<210> SEQ ID NO 55
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 55
gggatggaga agagtgagga                                                 20

<210> SEQ ID NO 56
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 56
tcctcactct tctccatccc                                                 20
```

```
<210> SEQ ID NO 57
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 3

<400> SEQUENCE: 57
accctgtatg ttgccttgg                                                19

<210> SEQ ID NO 58
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 58
ggggattttg ctgtgtgctg                                               20

<210> SEQ ID NO 59
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 59
attcctgctc ccaccgtctc                                               20

<210> SEQ ID NO 60
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 60
cacagagtgt ccgagaggca                                               20

<210> SEQ ID NO 61
<211> LENGTH: 22
<212> TYPE: DNA
<213> ORGANISM: Homo sapiens
<220> FEATURE:
<221> NAME/KEY: misc_feature
<222> LOCATION: (1)..(22)
<223> OTHER INFORMATION: /label= Table 3

<400> SEQUENCE: 61
ggagattatc aggtgagatg cc                                            22

<210> SEQ ID NO 62
<211> LENGTH: 21
<212> TYPE: DNA
<213> ORGANISM: Homo sapiens
<220> FEATURE:
<221> NAME/KEY: misc_feature
<222> LOCATION: (1)..(21)
```

<223> OTHER INFORMATION: /label= Table 3

<400> SEQUENCE: 62
cagagtgtcc gagaggcagg g                                              21

<210> SEQ ID NO 63
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 63
cgttgacccc tccaccttga                                                20

<210> SEQ ID NO 64
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 64
gggaaaacat gcaccttctt                                                20

<210> SEQ ID NO 65
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 65 taggggtaa aatggaggag                                                 20

<210> SEQ ID NO 66
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: /label= Table 3

<400> SEQUENCE: 66
actaactcag tggaataggg                                                20

<210> SEQ ID NO 67
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 3

<400> SEQUENCE: 67
ggagctagga tagctcaat                                                 19

<210> SEQ ID NO 68
<211> LENGTH: 1302

```
<212> TYPE: DNA
<213> ORGANISM: Homo sapiens
<220> FEATURE:
<221> NAME/KEY: misc_feature
<222> LOCATION: (1)..(1302)
<223> OTHER INFORMATION: /note= Flanking 5' genomic region of the
      sequence of the human nCL1 cDNA described in Figure 2a
<220> FEATURE:
<221> NAME/KEY: misc_feature
<222> LOCATION: (-477)..(-472)
<223> OTHER INFORMATION: /note= Putative Sp1 in Figure 2a
<220> FEATURE:
<221> NAME/KEY: misc_feature
<222> LOCATION: (-364)..(-343)
<223> OTHER INFORMATION: /note= MEF2 binding sites in Figure 2a
<220> FEATURE:
<221> NAME/KEY: misc_feature
<222> LOCATION: (-685)..(-672)
<223> OTHER INFORMATION: /note= CArG box in Figure 2a

<400> SEQUENCE: 68
```

| | | | |
|---|---|---|---|
| atatcagtta gcctggtttc actatacagt acatcatttt gcttaaagtc acagcttacg | 60 |
| agaacctatc gatgatgtta agtgaggatt ttctctgctc aggtgcactt tttttttttt | 120 |
| ttaagacgga gtctctttct gtcacctggg ctggagtgca gtggcgtgat ctgggttcac | 180 |
| tacaacctct ccctcctggg ttcaagcaat tcttctgtct cagcctccca gtagctggg | 240 |
| attacaggca ccccccgcca cacccggctt attttgtat ttttagtaga cagggttt | 300 |
| cactattgtt gtccatgctg gtctcgaact cgtgacctca tgtgatccac ccgcctcggc | 360 |
| ctcccaaagt gcagagatta gagacgtgat ccacatggcc cagcaggacc acttttagc | 420 |
| agattcagtc ccagtgttca ttttgtggat ggggagagac aagaggtggc aaggtcaagt | 480 |
| gtgcaggtag agacagggat tttctcaaat gaggactctg ctgagtagca ttttccatgc | 540 |
| agacatttcc aatgagcgct gacccaagaa cattctaaaa aagataccaa atctaacatt | 600 |
| gaataatgtt ctgatatcct aaaattttag gactaaaaat catgttctct aaaattcaca | 660 |
| gaatattttt gtagaattca gtacctcccg ttcaccctaa ctagcttttt tgcaatattg | 720 |
| ttttccattc atttgatggc cagtagttgg gtggtctgta taactgccta ctcaataaca | 780 |
| tgtcagcagt tctcagcttc tttccagtgt tcaccttact cagatactcc cttttcattt | 840 |
| tctggcaaca ccagcacttc atggcaacag aaatgtccct agccaggttc tctctctacc | 900 |
| atgcagtctc tcttgctctc atactcacag tgtttcttca catctatttt tagttttcct | 960 |
| ggctcaagca tcttcaggcc actgaaacac aaccctcact ctctttctct ctccctctgg | 1020 |
| catgcatgct gctggtagga gacccccaag tcaacattgc ttcagaaatc ctttagcact | 1080 |
| catttctcag gagaacttat ggcttcagaa tcacagctcg gttttaaga tggacataac | 1140 |
| ctgtccgacc ttctgatggg ctttcaactt tgaactggat gtggacactt ttctctcaga | 1200 |
| tgacagaatt actccaactt cccctttgca gttgcttcct ttccttgaag gtagctgtat | 1260 |
| cttattttct ttaaaaagct ttttcttcca aagccacttg cc | 1302 |

```
<210> SEQ ID NO 69
<211> LENGTH: 1381
<212> TYPE: DNA
<213> ORGANISM: Homo sapiens
<220> FEATURE:
<221> NAME/KEY: misc_feature
<222> LOCATION: (1)..(1381)
<223> OTHER INFORMATION: /note= Flanking 3' genomic region of the
      sequence of the human nCL1 cDNA described in Figure 2c

<400> SEQUENCE: 69
```

```
                              ac caggctggcc    12
tcatccaaag ccatgcagga tcactcagga tttcagtttc accctctatt tccaaagcca    72
tttacctcaa aggacccagc agctacaccc ctacaggctt ccaggcacct catcagtcat   132
gttcctcctc cattttaccc cctacccatc cttgatcggt catgcctagc ctgacccttt   192
agtaaagcaa tgaggtagga agaacaaacc cttgtccctt tgccatgtgg aggaaagtgc   252
ctgcctctgg tccgagccgc ctcggttctg aagcgagtgc tcctgcttac cttgctctag   312
gctgtctgca gaagcacctg ccggtggcac tcagcacctc cttgtgctag agccctccat   372
cacccttcacg ctgtcccacc atgggccagg aaccaaacca gcactgggtt ctactgctgt   432
ggggtaaaact aactcagtgg aatagggctg gttactttgg gctgtccaac tcataagttt   492
ggctgcattt tgaaaaaagc tgatctaaat aaaggcatgt gtatggctgg tccccttgtg   552
ttttgttgtc tcacatttag atatcagcca tgcatgactg aatggcttcc aatcatatac   612
tcacctatca cctacaagag aacaatgaaa acacacaca aaaacaaaat cttgaatttt   672
gtaatcatgc ctattgctat ttcttgagca taagaatggc tcagatactt tccaagacat   732
aaaaggaagg cagaggaata gttgttgctg taaaagacat caagaataaa tgggtcatgt   792
acaacgggag gggccggtta cctgaataat ggagtggaga ttgagctatc ctagctcctc   852
tgctcactaa ctgacctgtc gcatgaccgt ggacaaaacc ctgaacgcag ctgtttgttt   912
gctaaacttc tctggaccat ggcctgcggc atatctatag gcatcctgtg ttttccaccc   972
agtttccttc ttcctcgcta agccaacgtg aaagggctg gccgtgaata tgcagacaag  1032
gtaacgaaag taaaccgtca attagtaaaa gtacttcatt ttcctcttgt atttgcttca  1092
tatcttgctt cacaaagtta cgaagttcac agctttatac caaaatgtaa gaaggctatt  1152
tgcttataaa cattttttgca gtcaggtgtc atctgatttc attcttctaa tccatattca  1212
atattanaaa aatcagaaac caaggggtgct ggagcagctc tagggcatat atttctctta  1272
aataggagaa agattttcaa cagcttttcc tccttgaccc cctcctttcc caatttattt  1332
gggtcactac cttgaattta gagtgaatct gggaaatgta gtcaccagg          1381
```

<210> SEQ ID NO 70
<211> LENGTH: 2466
<212> TYPE: DNA
<213> ORGANISM: Homo sapiens
<220> FEATURE:
<221> NAME/KEY: misc_feature
<222> LOCATION: (1)..(2466)
<223> OTHER INFORMATION: /note= Sequence of the human nCL1 cDNA
      described in Figure 2b

<400> SEQUENCE: 70

```
                              atgccgac cgtcattagc    18
gcatctgtgg ctccaaggac agcggctgag ccccggtccc cagggccagt tcctcacccg    78
gcccagagca aggccactga ggctgggggt ggaaacccaa gtggcatcta ttcagccatc   138
atcagccgca attttcctat tatcggagtg aagagaaga cattcgagca acttcacaag   198
aaatgtctag aaaagaaagt tctttatgtg gaccctgagt tcccaccgga tgagacctct   258
ctcttttata gccagaagtt ccccatccag ttcgtctgga agagacctcc ggaaatttgc   318
gagaatcccc gatttatcat tgatggagcc aacagaactg acatctgtca aggagagcta   378
ggggactgct ggtttctcgc agccattgcc tgcctgaccc tgaaccagca ccttctttc   438
cgagtcatac cccatgatca aagtttcatc gaaaactacg cagggatctt ccacttccag   498
```

-continued

```
ttctggcgct atggagagtg ggtggacgtg gttatagatg actgcctgcc aacgtacaac    558
aatcaactgg ttttcaccaa gtccaaccac cgcaatgagt tctggagtgc tctgctggag    618
aaggcttatg ctaagctcca tggttcctac gaagctctga aggtgggaa caccacagag    678
gccatggagg acttcacagg agggtggca gagttttttg agatcaggga tgctcctagt    738
gacatgtaca agatcatgaa gaaagccatc gagagaggct ccctcatggg ctgctccatt    798
gatgatggca cgaacatgac ctatggaacc tctccttctg gtctgaacat ggggagttg    858
attgcacgga tggtaaggaa tatggataac tcactgctcc aggactcaga cctcgacccc    918
agaggctcag atgaaagacc gacccggaca atcattccgg ttcagtatga caagaatg    978
gcctgcgggc tggtcagagg tcacgcctac tctgtcacgg gctggatga ggtcccgttc    1038
aaaggtgaga aagtgaagct ggtgcggctg cggaatccgt ggggccaggt ggagtggaac    1098
ggttcttgga gtgatagatg aaggactgg agctttgtgg acaaagatga aaggcccgt    1158
ctgcagcacc aggtcactga ggatggagag ttctggatgt cctatgagga tttcatctac    1218
catttcacaa agttggagat ctgcaacctc acggccgatg ctctgcagtc tgacaagctt    1278
cagacctgga cagtgtctgt gaacgagggc cgctgggtac ggggttgctc tgccggaggc    1338
tgccgcaact tcccagatac tttctggacc aaccctcagt accgtctgaa gctcctggag    1398
gaggacgatg accctgatga ctcggaggtg atttgcagct tcctggtggc cctgatgcag    1458
aagaaccggc ggaaggaccg gaagctaggg gccagtctct tcaccattgg cttcgccatc    1518
tacgaggttc ccaaagagat gcacgggaac aagcagcacc tgcagaagga cttcttcctg    1578
tacaacgcct ccaaggccag gagcaaaacc tacatcaaca tgcgggaggt gtcccagcgc    1638
ttccgcctgc ctcccagcga gtacgtcatc gtgccctcca cctacgagcc ccaccaggag    1698
ggggaattca tcctccgggt cttctctgaa aagaggaacc tctctgagga agttgaaaat    1758
accatctccg tggatcggcc agtgaaaaag aaaaaaacca agcccatcat cttcgtttcg    1818
gacagagcaa acagcaacaa ggagctgggt gtggaccagg agtcagagga gggcaaaggc    1878
aaaacaagcc ctgataagca aaagcagtcc ccacagccac agcctggcag ctctgatcag    1938
gaaagtgagg aacagcaaca attccggaac attttcaagc agatagcagg agatgacatg    1998
gagatctgtg cagatgagct caagaaggtc cttaacacag tcgtgaacaa acacaaggac    2058
ctgaagacac acgggttcac actggagtcc tgccgtagca tgattgcgct catggataca    2118
gatggctctg gaaagctcaa cctgcaggag ttccaccacc tctggaacaa gattaaggcc    2178
tggcagaaaa ttttcaaaca ctatgacaca gaccagtccg gcaccatcaa cagctacgag    2238
atgcgaaatg cagtcaacga cgcaggattc cacctcaaca accagctcta tgacatcatt    2298
accatgcggt acgcagacaa acacatgaac atcgactttg acagtttcat ctgctgcttc    2358
gttaggctgg agggcatgtt cagagctttt catgcatttg acaaggatgg agatggtatc    2418
atcaagctca acgttctgga gtggctgcag ctcaccatgt atgcctga              2466
```

<210> SEQ ID NO 71  
<211> LENGTH: 11  
<212> TYPE: DNA  
<213> ORGANISM: Homo sapiens  
<220> FEATURE:  
<221> NAME/KEY: misc_feature  
<222> LOCATION: (1)..(11)  
<223> OTHER INFORMATION: /label= Table 2

<400> SEQUENCE: 71
ctccggtgag t                                                          11

```
<210> SEQ ID NO 72
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 72
gctaggtagg a                                                          11

<210> SEQ ID NO 73
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 73
tccaggtgag g                                                          11

<210> SEQ ID NO 74
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 74
gctaagtaag c                                                          11

<210> SEQ ID NO 75
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 75
ttgatgtaag t                                                          11

<210> SEQ ID NO 76
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 76
cccgggtgtg t                                                          11

<210> SEQ ID NO 77
<211> LENGTH: 11
<212> TYPE: DNA
<213> ORGANISM: Homo sapiens
<220> FEATURE:
<221> NAME/KEY: misc_feature
<222> LOCATION: (1)..(11)
```

```
<223> OTHER INFORMATION: /label= Table 2

<400> SEQUENCE: 77
atgaggtaag c                                                        11

<210> SEQ ID NO 78
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 78
gataggtagg t                                                        11

<210> SEQ ID NO 79
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 79
ttctggtgag t                                                        11

<210> SEQ ID NO 80
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 80
cccaggtggg a                                                        11

<210> SEQ ID NO 81
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 81
acgaggtgtg t                                                        11

<210> SEQ ID NO 82
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 82
aagaggtata g                                                        11

<210> SEQ ID NO 83
<211> LENGTH: 11
```

-continued

```
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 83
tctgagtgag t                                                         11

<210> SEQ ID NO 84
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 84
cagtggtgag t                                                         11

<210> SEQ ID NO 85
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 85
ccaaggtagg t                                                         11

<210> SEQ ID NO 86
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 86
cacaggtgtc t                                                         11

<210> SEQ ID NO 87
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 87
gagatgtgag t                                                         11

<210> SEQ ID NO 88
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 88
```

```
caaacgtgag t                                                          11

<210> SEQ ID NO 89
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 89
tggatgtatc c                                                          11

<210> SEQ ID NO 90
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 90
ggcaggtggg a                                                          11

<210> SEQ ID NO 91
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 91
cgcaggtgct g                                                          11

<210> SEQ ID NO 92
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 92
tttttgtttc acaggaaat                                                  19

<210> SEQ ID NO 93
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 93
gtgtctgcct gcagggac                                                   19

<210> SEQ ID NO 94
<211> LENGTH: 19
<212> TYPE: DNA
<213> ORGANISM: Homo sapiens
<220> FEATURE:
<221> NAME/KEY: misc_feature
```

```
<222> LOCATION: (1)..(19)
<223> OTHER INFORMATION: /label= Table 2

<400> SEQUENCE: 94
acgcttctgt gcagttctg                                              19

<210> SEQ ID NO 95
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 95
atcctctctc taaggctcc                                              19

<210> SEQ ID NO 96
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 96
ccatcgggcc tcaggatgg                                              19

<210> SEQ ID NO 97
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 97
ttactgctct acagacaat                                              19

<210> SEQ ID NO 98
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 98
tctgtgtgct taaggtccc                                              19

<210> SEQ ID NO 99
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 99
cattttccca ccagatgga                                              19

<210> SEQ ID NO 100
```

```
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 100
ttccaacctc tcaggatgt                                                19

<210> SEQ ID NO 101
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 101
ttctgggggt gcagatact                                                19

<210> SEQ ID NO 102
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 102
tgtttcttct caaggttcc                                                19

<210> SEQ ID NO 103
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 103
tccccatctc tcagatgca                                                19

<210> SEQ ID NO 104
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 104
tgtattcctc acagggaag                                                19

<210> SEQ ID NO 105
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 105
```
cttttcttat gcagaaaaa                                          19

<210> SEQ ID NO 106
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 106
cctcctctct ccagcccat                                          19

<210> SEQ ID NO 107
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 107
ttgtgcctcc acagccaca                                          19

<210> SEQ ID NO 108
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 108
cccttcctcc tcaggacat                                          19

<210> SEQ ID NO 109
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 109
ctccatcccc ccagacaag                                          19

<210> SEQ ID NO 110
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 110
cctccctcct ccagacaga                                          19

<210> SEQ ID NO 111
<211> LENGTH: 19
<212> TYPE: DNA
<213> ORGANISM: Homo sapiens
<220> FEATURE:

-continued

<221> NAME/KEY: misc_feature
<222> LOCATION: (1)..(19)
<223> OTHER INFORMATION: /label= Table 2

<400> SEQUENCE: 111 tttctattg ccagaaata                                              19

<210> SEQ ID NO 112
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 112
ggtcccctcc acaggattc                                             19

<210> SEQ ID NO 113
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 113
gttcagtaag t                                                     11

<210> SEQ ID NO 114
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: /label= Table 2

<400> SEQUENCE: 114
tggaggtaaa g                                                     11

<210> SEQ ID NO 115
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 115
gcattctttc acaggagct                                             19

<210> SEQ ID NO 116
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: /label= Table 2

<400> SEQUENCE: 116
gggacttctt tcagtggct                                             19